(12) United States Patent
Krimsky et al.

(10) Patent No.: US 11,938,317 B2
(45) Date of Patent: Mar. 26, 2024

(54) OPTIMIZATION OF ENERGY DELIVERY FOR VARIOUS APPLICATIONS

(71) Applicant: Galvanize Therapeutics, Inc., San Carlos, CA (US)

(72) Inventors: William Sanford Krimsky, Forest Hill, MD (US); Paul Brian Friedrichs, Belmont, CA (US); Roman Turovskiy, San Francisco, CA (US); Robert E. Neal, II, Palo Alto, CA (US); Jonathan Reuben Waldstreicher, West Orange, NJ (US); Kevin James Taylor, San Mateo, CA (US)

(73) Assignee: Galvanize Therapeutics, Inc., Redwood City, CA (US)

( * ) Notice: Subject to any disclaimer, the term of this patent is extended or adjusted under 35 U.S.C. 154(b) by 0 days.

(21) Appl. No.: 18/077,097

(22) Filed: Dec. 7, 2022

(65) Prior Publication Data

US 2023/0149706 A1    May 18, 2023

Related U.S. Application Data

(63) Continuation of application No. 16/914,200, filed on Jun. 26, 2020, now Pat. No. 11,547,851, which is a
(Continued)

(51) Int. Cl.
*A61N 1/05* (2006.01)
*A61N 1/20* (2006.01)
*A61N 1/37* (2006.01)

(52) U.S. Cl.
CPC ........... *A61N 1/0565* (2013.01); *A61N 1/205* (2013.01); *A61N 1/37* (2013.01)

(58) Field of Classification Search
CPC ........ A61N 1/0565; A61N 1/205; A61N 1/37; A61N 1/3625; A61N 1/365;
(Continued)

(56) References Cited

U.S. PATENT DOCUMENTS 5,386,837 A    2/1995    Sterzer
5,906,609 A    5/1999    Assa et al.
(Continued)

FOREIGN PATENT DOCUMENTS

CN    1867299 A    11/2006
CN    101426551 A    5/2009
(Continued)

OTHER PUBLICATIONS

A. Valipour et Al. Bronchial Rheoplasty Treatment for Chronic Bronchitis Using the Rheox System, 2020 American Thoracic Society, Abstract, Aug. 5, 2020.
(Continued)

*Primary Examiner* — Carl H Layno
*Assistant Examiner* — Anh-Khoa N Dinh
(74) *Attorney, Agent, or Firm* — Wilson Sonsini Goodrich & Rosati

(57) ABSTRACT

Energy is transmitted to a body lumen or passageway in the form of pulsed electric fields (PEFs) and in a manner which provides focal therapy. In some embodiments, PEFs are delivered through independent electrically active electrodes of an energy delivery body, typically in a monopolar fashion. Such delivery concentrates the electrical energy over a smaller surface area, resulting in stronger effects than delivery through an electrode extending circumferentially around the lumen or passageway. It also forces the electrical energy to be delivered in a staged regional approach, mitigating the effect of preferential current pathways through the surrounding tissue. Focal delivery of PEFs can provide increased
(Continued)

tissue lethality by employing precise timing and sequencing of energy delivery to the electrodes.

23 Claims, 22 Drawing Sheets

Related U.S. Application Data continuation of application No. PCT/US2018/067504, filed on Dec. 26, 2018.

(60) Provisional application No. 62/693,622, filed on Jul. 3, 2018, provisional application No. 62/610,430, filed on Dec. 26, 2017.

(58) Field of Classification Search
CPC ...... A61B 2018/124; A61B 2018/1467; A61B 2018/1475; A61B 18/1492; A61B 2018/00267; A61B 2018/00351; A61B 2018/00541; A61B 2018/00577; A61F 2/2427; A61F 2/2442; A61F 2/2454; A61F 2/2457; A61F 2/2466; A61F 2220/0008; A61F 2220/0016; A61F 2250/0097; A61M 2039/0646; A61M 39/06; A61M 5/14; A61M 2205/054

See application file for complete search history.

(56) References Cited

U.S. PATENT DOCUMENTS

| | | | |
|---|---|---|---|
| 6,038,478 A | 3/2000 | Yuen et al. |
| 6,107,699 A | 8/2000 | Swanson |
| 6,233,482 B1 | 5/2001 | Hofmann et al. |
| 6,248,056 B1 | 6/2001 | Persson |
| 6,326,177 B1 | 12/2001 | Schoenbach et al. |
| 6,366,808 B1 | 4/2002 | Schroeppel et al. |
| 6,569,149 B2 | 5/2003 | Dev et al. |
| 6,733,485 B1 | 5/2004 | Whitehurst et al. |
| 6,738,663 B2 | 5/2004 | Schroeppel et al. |
| 6,994,706 B2 | 2/2006 | Chornenky et al. |
| 7,130,697 B2 | 10/2006 | Chornenky et al. |
| 7,395,112 B2 | 7/2008 | Keisari et al. |
| 7,412,284 B2 | 8/2008 | Hofmann |
| 7,412,285 B2 | 8/2008 | Schroeppel et al. |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,713,740 B2 | 5/2010 | Jaroszeski et al. |
| 7,742,811 B2 | 6/2010 | Schroeppel et al. |
| 7,765,010 B2 | 7/2010 | Chornenky et al. |
| 7,805,201 B2 | 9/2010 | Palti |
| RE42,016 E | 12/2010 | Chornenky et al. |
| 7,879,610 B1 | 2/2011 | Heller et al. |
| 7,917,227 B2 | 3/2011 | Palti |
| 8,014,854 B2 | 9/2011 | Schroeppel et al. |
| 8,019,414 B2 | 9/2011 | Palti |
| 8,024,048 B2 | 9/2011 | Schroeppel et al. |
| 8,026,223 B1 | 9/2011 | Heller et al. |
| 8,105,324 B2 | 1/2012 | Palanker et al. |
| 8,109,926 B2 | 2/2012 | Azure |
| 8,114,070 B2 | 2/2012 | Rubinsky et al. |
| 8,231,603 B2 | 7/2012 | Hobbs et al. |
| 8,244,345 B2 | 8/2012 | Palti |
| 8,298,222 B2 | 10/2012 | Rubinsky et al. |
| 8,406,870 B2 | 3/2013 | Palti |
| 8,465,484 B2 | 6/2013 | Davalos et al. |
| 8,500,713 B2 | 8/2013 | Ferek-Petric |
| 8,512,334 B2 | 8/2013 | Nuccitelli et al. |
| 8,600,494 B2 | 12/2013 | Schroeppel et al. |
| 8,634,929 B2 | 1/2014 | Chornenky et al. |
| 8,802,643 B1 | 8/2014 | Heller et al. |
| 8,814,860 B2 | 8/2014 | Davalos et al. |
| 8,927,518 B1 | 1/2015 | Heller et al. |
| 8,992,517 B2 | 3/2015 | Davalos et al. |
| 9,037,230 B2 | 5/2015 | Goldfarb et al. |
| 9,101,764 B2 | 8/2015 | Nuccitelli et al. |
| 9,125,666 B2 | 9/2015 | Steinke et al. |
| 9,168,373 B2 | 10/2015 | Nuccitelli et al. |
| 9,211,155 B2 | 12/2015 | Fruland et al. |
| 9,242,041 B2 | 1/2016 | Kosik et al. |
| 9,610,364 B1 | 4/2017 | Heller et al. |
| 9,629,912 B2 | 4/2017 | Soikum et al. |
| 9,655,669 B2 | 5/2017 | Palti et al. |
| 9,656,066 B2 | 5/2017 | Nuccitelli et al. |
| 9,724,155 B2 | 8/2017 | Nuccitelli et al. |
| 9,833,617 B2 | 12/2017 | Travers et al. |
| 9,943,684 B2 | 4/2018 | Nuccitelli et al. |
| 10,143,512 B2 | 12/2018 | Rubinsky et al. |
| 10,143,759 B1 | 12/2018 | Heller et al. |
| 10,154,869 B2 | 12/2018 | Onik et al. |
| 10,154,874 B2 | 12/2018 | Davalos et al. |
| 10,292,755 B2 | 5/2019 | Arena et al. |
| 10,391,125 B2 | 8/2019 | Nuccitelli et al. |
| 10,426,847 B2 | 10/2019 | Pierce et al. |
| 10,448,989 B2 | 10/2019 | Arena et al. |
| 10,471,254 B2 | 11/2019 | Sano et al. |
| 10,702,337 B2 | 7/2020 | Waldstreicher et al. |
| 10,939,958 B2 | 3/2021 | Waldstreicher et al. |
| 11,324,543 B2 | 5/2022 | Waldstreicher et al. |
| 11,369,433 B2 | 6/2022 | Waldstreicher et al. |
| 11,471,208 B2 | 10/2022 | Waldstreicher et al. |
| 11,547,851 B2 | 1/2023 | Krimsky et al. |
| 2001/0008016 A1 | 7/2001 | Kotani et al. |
| 2001/0020166 A1 | 9/2001 | Daly et al. |
| 2002/0010491 A1 | 1/2002 | Schoenbach et al. |
| 2002/0022839 A1 | 2/2002 | Stewart et al. |
| 2002/0103483 A1 | 8/2002 | Edwards |
| 2002/0115991 A1 | 8/2002 | Edwards |
| 2002/0198567 A1 | 12/2002 | Keisari et al. |
| 2003/0170898 A1 | 9/2003 | Gundersen et al. |
| 2003/0199050 A1 | 10/2003 | Mangano et al. |
| 2004/0044338 A1 | 3/2004 | Lennox et al. |
| 2005/0096647 A1 | 5/2005 | Steinke et al. |
| 2005/0171574 A1 | 8/2005 | Rubinsky et al. |
| 2005/0222646 A1 | 10/2005 | Kroll et al. |
| 2006/0264752 A1 | 11/2006 | Rubinsky et al. |
| 2006/0269531 A1 | 11/2006 | Beebe et al. |
| 2006/0293731 A1 | 12/2006 | Rubinsky et al. |
| 2007/0021803 A1 | 1/2007 | Deem et al. |
| 2007/0025919 A1 | 2/2007 | Deem et al. |
| 2007/0129720 A1 | 6/2007 | Demarais et al. |
| 2007/0191904 A1 | 8/2007 | Libbus et al. |
| 2008/0015571 A1 | 1/2008 | Rubinsky et al. |
| 2008/0161801 A1* | 7/2008 | Steinke ............ A61B 18/1815 606/41 |
| 2008/0306570 A1 | 12/2008 | Rezai et al. |
| 2008/0319372 A1 | 12/2008 | Palti et al. |
| 2009/0247933 A1 | 10/2009 | Maor et al. |
| 2009/0281477 A1 | 11/2009 | Mikus et al. |
| 2009/0292342 A1 | 11/2009 | Rubinsky et al. |
| 2009/0306644 A1 | 12/2009 | Mayse et al. |
| 2010/0179530 A1 | 7/2010 | Long et al. |
| 2010/0228248 A1 | 9/2010 | Griffin |
| 2010/0240995 A1 | 9/2010 | Nuccitelli et al. |
| 2010/0256630 A1 | 10/2010 | Hamilton, Jr. et al. |
| 2011/0118732 A1 | 5/2011 | Rubinsky et al. |
| 2011/0152855 A1 | 6/2011 | Mayse et al. |
| 2011/0202052 A1 | 8/2011 | Gelbart et al. |
| 2011/0288545 A1 | 11/2011 | Beebe et al. |
| 2012/0143120 A1 | 6/2012 | Goldfarb et al. |
| 2012/0150172 A1 | 6/2012 | Ortiz et al. |
| 2012/0220998 A1 | 8/2012 | Long et al. |
| 2012/0220999 A1 | 8/2012 | Long |
| 2012/0226271 A1 | 9/2012 | Callas et al. |
| 2012/0315704 A1 | 12/2012 | Beebe et al. |
| 2012/0330306 A1 | 12/2012 | Long et al. |
| 2014/0039491 A1 | 2/2014 | Bakos et al. |
| 2014/0058294 A1 | 2/2014 | Gross et al. |
| 2014/0081263 A1 | 3/2014 | Mesallum |
| 2014/0107478 A1 | 4/2014 | Seward et al. |
| 2015/0045788 A1 | 2/2015 | Litscher et al. |

(56) References Cited

U.S. PATENT DOCUMENTS

| | | |
|---|---|---|
| 2015/0119879 A1 | 4/2015 | Jameson et al. |
| 2015/0182282 A1 | 7/2015 | Zemel et al. |
| 2015/0201996 A1 | 7/2015 | Rubinsky et al. |
| 2015/0289923 A1 | 10/2015 | Davalos et al. |
| 2015/0342669 A1 | 12/2015 | Flanagan et al. |
| 2016/0000499 A1 | 1/2016 | Lennox et al. |
| 2016/0128767 A1 | 5/2016 | Azamian et al. |
| 2016/0199131 A1 | 7/2016 | Allison et al. |
| 2016/0206370 A1 | 7/2016 | Fruland et al. |
| 2016/0361109 A1 | 12/2016 | Weaver et al. |
| 2016/0367310 A1 | 12/2016 | Onik et al. |
| 2017/0049513 A1 | 2/2017 | Cosman, Jr. et al. |
| 2017/0065343 A1 | 3/2017 | Mickelsen |
| 2017/0087224 A1 | 3/2017 | Quake |
| 2017/0105793 A1 | 4/2017 | Cao et al. |
| 2017/0119465 A1 | 5/2017 | Long et al. |
| 2017/0135723 A1 | 5/2017 | Zarembinski |
| 2017/0215939 A1 | 8/2017 | Palti et al. |
| 2017/0216585 A1 | 8/2017 | Goldfarb et al. |
| 2017/0266283 A1 | 9/2017 | Soikum et al. |
| 2017/0281934 A1 | 10/2017 | Giladi et al. |
| 2017/0304002 A1 | 10/2017 | Beebe et al. |
| 2017/0319843 A1 | 11/2017 | Beebe et al. |
| 2018/0000895 A1 | 1/2018 | Pierce et al. |
| 2018/0028267 A1 | 2/2018 | Onik et al. |
| 2018/0071014 A1 | 3/2018 | Neal et al. |
| 2018/0085575 A1 | 3/2018 | Travers et al. |
| 2018/0104486 A1 | 4/2018 | Yoon et al. |
| 2018/0110557 A1 | 4/2018 | Muratori et al. |
| 2018/0110978 A1 | 4/2018 | Beebe et al. |
| 2018/0132922 A1 | 5/2018 | Neal, II |
| 2018/0154142 A1 | 6/2018 | Guo et al. |
| 2018/0193082 A1 | 7/2018 | Rubinsky et al. |
| 2018/0193088 A1 | 7/2018 | Sutton et al. |
| 2018/0200510 A1 | 7/2018 | Nuccitelli et al. |
| 2018/0221078 A1 | 8/2018 | Howard et al. |
| 2018/0263685 A1 | 9/2018 | Onik et al. |
| 2018/0289954 A1 | 10/2018 | Hebb et al. |
| 2018/0344378 A1 | 12/2018 | Wolf et al. |
| 2019/0046791 A1 | 2/2019 | Ebbers et al. |
| 2019/0099214 A1 | 4/2019 | Rubinsky et al. |
| 2019/0105408 A1 | 4/2019 | Heller et al. |
| 2019/0117963 A1 | 4/2019 | Travers et al. |
| 2019/0117969 A1 | 4/2019 | Schmidt et al. |
| 2019/0160283 A1 | 5/2019 | Nuccitelli et al. |
| 2019/0223938 A1 | 7/2019 | Arena et al. |
| 2019/0223943 A1 | 7/2019 | Forsyth et al. |
| 2019/0232048 A1 | 8/2019 | Latouche et al. |
| 2019/0239949 A1 | 8/2019 | Nuccitelli et al. |
| 2019/0254735 A1 | 8/2019 | Stewart et al. |
| 2019/0269912 A1 | 9/2019 | Viswanathan et al. |
| 2019/0282294 A1 | 9/2019 | Davalos et al. |
| 2019/0299019 A1 | 10/2019 | Chornenky et al. |
| 2019/0307781 A1 | 10/2019 | Krex et al. |
| 2019/0328445 A1 | 10/2019 | Sano et al. |
| 2019/0350971 A1 | 11/2019 | Nuccitelli et al. |
| 2019/0351224 A1 | 11/2019 | Sano et al. |
| 2020/0000938 A1 | 1/2020 | Pierce et al. |
| 2020/0009377 A1 | 1/2020 | Chang et al. |
| 2020/0016067 A1 | 1/2020 | Gotlib et al. |
| 2020/0038093 A1 | 2/2020 | Onik |
| 2020/0046423 A1 | 2/2020 | Viswanathan et al. |
| 2020/0046967 A1 | 2/2020 | Ivey et al. |
| 2020/0275973 A1 | 9/2020 | O'Brien et al. |
| 2021/0023362 A1 | 1/2021 | Lorenzo et al. |
| 2021/0146126 A1 | 5/2021 | Waldstreicher et al. |
| 2021/0236815 A1 | 8/2021 | Waldstreicher et al. |
| 2021/0236816 A1 | 8/2021 | Waldstreicher et al. |
| 2021/0393327 A1 | 12/2021 | Eyster et al. |
| 2022/0104875 A1 | 4/2022 | Gleiman et al. |
| 2022/0387095 A1 | 12/2022 | Neal et al. |
| 2023/0082389 A1 | 3/2023 | Waldstreicher et al. |
| 2023/0172650 A1 | 6/2023 | Castellvi et al. |

FOREIGN PATENT DOCUMENTS

| | | |
|---|---|---|
| CN | 101553180 A | 10/2009 |
| CN | 102014779 A | 4/2011 |
| CN | 103027745 A | 4/2013 |
| CN | 103252016 A | 8/2013 |
| CN | 103281978 A | 9/2013 |
| CN | 103781433 A | 5/2014 |
| CN | 103796603 A | 5/2014 |
| CN | 104602754 A | 5/2015 |
| CN | 104703557 A | 6/2015 |
| CN | 107194119 A | 9/2017 |
| CN | 107205772 A | 9/2017 |
| CN | 108024803 A | 5/2018 |
| CN | 109788979 A | 5/2019 |
| EP | 0935482 B1 | 5/2005 |
| EP | 1991303 A2 | 11/2008 |
| EP | 1648555 B1 | 9/2015 |
| EP | 2736432 B1 | 3/2016 |
| EP | 2661236 B1 | 8/2016 |
| EP | 3003470 B1 | 8/2017 |
| EP | 3290082 A2 | 3/2018 |
| EP | 2994045 B1 | 5/2019 |
| EP | 3569144 A1 | 11/2019 |
| JP | 2003529401 A | 10/2003 |
| JP | 2007504910 A | 3/2007 |
| JP | 2010509032 A | 3/2010 |
| JP | 2012515018 A | 7/2012 |
| JP | 2017518805 A | 7/2017 |
| WO | WO-9814238 A1 | 4/1998 |
| WO | WO-9906101 A1 | 2/1999 |
| WO | WO-0110319 A1 | 2/2001 |
| WO | WO-02098501 A2 | 12/2002 |
| WO | WO-03047684 A2 | 6/2003 |
| WO | WO-2004037341 A2 | 5/2004 |
| WO | WO-2004110371 A2 | 12/2004 |
| WO | WO-2005044371 A1 | 5/2005 |
| WO | WO-2005065284 A2 | 7/2005 |
| WO | WO-2005115535 A2 | 12/2005 |
| WO | WO-2005032646 A3 | 4/2006 |
| WO | WO-2006036706 A1 | 4/2006 |
| WO | WO-2006085150 A2 | 8/2006 |
| WO | WO-2006116608 A2 | 11/2006 |
| WO | WO-2006131816 A2 | 12/2006 |
| WO | WO-2007001747 A2 | 1/2007 |
| WO | WO-2007001751 A1 | 1/2007 |
| WO | WO-2007039799 A3 | 7/2007 |
| WO | WO-2007100727 A2 | 9/2007 |
| WO | WO-2007103070 A2 | 9/2007 |
| WO | WO-2008034100 A2 | 3/2008 |
| WO | WO-2008087489 A2 | 7/2008 |
| WO | WO-2009137800 A2 | 11/2009 |
| WO | WO-2010022275 A1 | 2/2010 |
| WO | WO-2010093692 A2 | 8/2010 |
| WO | WO-2010107947 A1 | 9/2010 |
| WO | WO-2010118387 A1 | 10/2010 |
| WO | WO-2010151277 A1 | 12/2010 |
| WO | WO-2011135294 A1 | 11/2011 |
| WO | WO-2012088149 A2 | 6/2012 |
| WO | WO-2014181167 A1 | 11/2014 |
| WO | WO-2014197240 A2 | 12/2014 |
| WO | WO-2014204978 A1 | 12/2014 |
| WO | WO-2015085162 A1 | 6/2015 |
| WO | WO-2015175570 A1 | 11/2015 |
| WO | WO-2016014264 A1 | 1/2016 |
| WO | WO-2016036891 A1 | 3/2016 |
| WO | WO-2016098781 A1 | 6/2016 |
| WO | WO-2016112359 A1 | 7/2016 |
| WO | WO-2016123608 A2 | 8/2016 |
| WO | WO-2016126778 A1 | 8/2016 |
| WO | WO-2016149575 A1 | 9/2016 |
| WO | WO-2016164473 A1 | 9/2016 |
| WO | WO-2016178697 A1 | 11/2016 |
| WO | WO-2016179712 A1 | 11/2016 |
| WO | WO-2016201264 A1 | 12/2016 |
| WO | WO-2017120169 A1 | 7/2017 |
| WO | WO-2017173089 A1 | 10/2017 |
| WO | WO-2017175116 A1 | 10/2017 |
| WO | WO-2018005511 A1 | 1/2018 |

(56) References Cited

FOREIGN PATENT DOCUMENTS

| | | |
|---|---|---|
| WO | WO-2018010659 A1 | 1/2018 |
| WO | WO-2018065806 A1 | 4/2018 |
| WO | WO-2018067999 A1 | 4/2018 |
| WO | WO-2018075946 A1 | 4/2018 |
| WO | WO-2018106672 A1 | 6/2018 |
| WO | WO-2019032474 A1 | 2/2019 |
| WO | WO-2019084011 A1 | 5/2019 |
| WO | WO-2019095604 A1 | 5/2019 |
| WO | WO-2019100016 A1 | 5/2019 |
| WO | WO-2019108540 A1 | 6/2019 |
| WO | WO-2019133606 A1 | 7/2019 |
| WO | WO-2019133608 A1 | 7/2019 |
| WO | WO-2019178500 A1 | 9/2019 |
| WO | WO-2019197973 A1 | 10/2019 |
| WO | WO-2020010188 A1 | 1/2020 |
| WO | WO-2020018662 A1 | 1/2020 |
| WO | WO-2020215007 A1 | 10/2020 |
| WO | WO-2021011733 | 1/2021 |
| WO | WO-2021127558 A1 | 6/2021 |
| WO | WO-2021207385 A1 | 10/2021 |
| WO | WO-2022031797 A1 | 2/2022 |
| WO | WO-2022204479 A1 | 9/2022 |
| WO | WO-2022260723 A1 | 12/2022 |

OTHER PUBLICATIONS

A. Valipour, et Al. First-in-Human Results of Bronchial Rheoplasty: An Endobronchial Treatment for Chronic Bronchitis (CB), Epidemiology and Therapy, Mini Symposium, May 22, 2019, Abstract.

Appelbaum et al., US Findings after Irreversible Electroporation Ablation: Radiologic-Pathologic Correlation, Radiology: vol. 262: No. 1—Jan. 2012.

Arschang Valipour et al. Bronchial Rheoplasty for Treatment of Chronic Bronchitis, American Journal of Respritory and Critical Care Medicine, vol. 202, No. 5, Sep. 1, 2020, pp. 681-689.

Arschang Valipour et al. Bronchial Rheoplasty for Treatment of Chronic Bronchitis. Twelve-Month Results from a Multicenter Clinical Trial, American Journal of Respiratory and Critical Care Medicine, vol. 202, Issue 5, 2019.

Arschang Valipour, et Al. Late Breaking Abstract—Bronchial Rheoplasty for Treatment of Chronic Bronchitis: 6 Month Results from a Prospective Multi-Center Study, Abstract, European Respiratory Journal 2019, pp. 1-5.

Charalambous et al., The Efficacy and Safety of the Open Approach Irreversible Electroporation in the Treatment of Pancreatic Cancer: A Systematic Review, European Journal of Surgical Oncology; vol. 46, No. 9, Sep. 2020.

Davalos et al., Implications and Considerations of Thermal Effects When Applying Irreversible ElectroporationTissue AblationTherapy, Prostate;vol. 75, No. 10; pp. 1114-1118, Jul. 1, 2015.

Edd et al., In Vivo Results of a New Focal Tissue Ablation Technique: Irreversible Electroporation, IEEE Transactions on Biomedical Engineering, vol. 53, No. 5; pp. 1409-1415; Jun. 2006.

EP18836576.1 Search Report dated Jun. 8, 2021.

EP20792123.0 Extended and Supplementary European Search Report dated Dec. 21, 2022.

Frandsen et al., Calcium electroporation Q4 in three cell lines; a comparison of bleomycin 2 and calcium, calcium compounds, and pulsing conditions, Biochimica et Biophysica Acta, vol. 1840, No. 3; pp. 1204-1208, Mar. 2014.

International Preliminary Report on Patentability for PCT/US2018/067501 dated Jun. 30, 2020.

International Search Report and Written Opinion for PCT/US2018/067504 dated Jun. 30, 2020.

International Search Report and Written Opinion for PCT/US2020/028844 dated Sep. 4, 2020.

Kundalia et al., Margin Accentuation for resectable Pancreatic cancer using Irreversible Electroporation e Results from the MACPIE-I study, European Journal of Surgical Oncology, vol. 47, No. 10: pp. 2571-2578; Oct. 2021.

Lu, et al., "Sequence-Modified Antibiotic Resistance Genes Provide Sustained Plasmid-Mediated Transgene Expression in Mammals" (2017) Molecular Therapy, vol. 25, No. 5, pp. 1187-1198.

Maor et al., Irreversible Electroporation Attenuates Neointimal Formation After Angioplasty, IEEE Transactions on Biomedical Engineering, vol. 55, No. 9, Sep. 2008.

Maor et al., The Effect of Irreversible Electroporation on Blood Vessels, Technology in Cancer Research and Treatment, vol. 6, No. 4, Aug. 2007.

Pallav L Shah, et al. *Epithelial Resurfacing: The Bronchial Skin Peel, American Thoracic Society*, May 22, 2020, pp. 1-8.

PCT/US2018/067501 International Search Report and Written Opinion dated Mar. 13, 2019.

PCT/US2021/026221 International Search Report and Written Opinion dated Jul. 21, 2021.

PCT/US2022/015217 International Search Report and Written Opinion dated May 6, 2022.

PCT/US2022/021888 International Search Report and Written Opinion dated Jun. 16, 2022.

Reddy et al., Pulsed Field Ablation of Paroxysmal Atrial Fibrillation, JACC Clin Electrophysiology vol. 7 No. 5, pp. 614-627, May 2021.

Rubinsky et al., "Irreversible Electroporation: a New Ablation Modality—Clinical Implications," Tech. Cancer Res. Treatment 6:1-12 (2007).

S. Fernandez-Bussy, et Al. Histopathologic Results Post Bronchial Rheoplasty , Epidemiology and Therapy, Mini Symposium, May 22, 2019, Abstract.

Timmer et al., Irreversible Electroporation for Locally Advanced Pancreatic Cancer, Techniques in Vascular and Interventional Radiology vol. 23, Issue 2, Jun. 2020.

U.S. Appl. No. 16/914,072 Notice of Allowance dated Jun. 20, 2022.

U.S. Appl. No. 17/214,688 Notice of Allowance dated Feb. 4, 2022.

U.S. Appl. No. 17/214,688 Notice of Allowance dated Mar. 2, 2022.

U.S. Appl. No. 16/914,200 Notice of Allowance dated Sep. 8, 2022.

U.S. Appl. No. 16/914,200 Office Action dated May 4, 2022.

U.S. Appl. No. 16/914,200 Office Action dated Oct. 22, 2021.

U.S. Appl. No. 17/214,688 Office Action dated Sep. 7, 2021.

U.S. Appl. No. 17/502,640 Office Action dated Apr. 28, 2023.

U.S. Appl. No. 17/502,640 Office Action dated Jul. 13, 2022.

U.S. Appl. No. 17/502,640 Office Action dated Mar. 14, 2022.

U.S. Appl. No. 17/214,688 Office Action dated May 25, 2021.

U.S. Appl. No. 16/914,072 Office Action dated Nov. 26, 2021.

V. Kim et Al. Bronchial Rheoplasty Increases Distal Airway Volume in Chronic Bronchitis, European Respiratory Journal 2019, vol. 54, Suppl. 63, PA2040 Abstract.

Valipour, A., Ing, A., Williamson, J., et al. Late Breaking Abstract—First-in-Human Results of Bronchial Rheoplasty: An Endobronchial Treatment for Chronic Bronchitis (CB). European Respiratory Journal 2018 52: Suppl. 62, OA2162.

Verma et al., Primer on Pulsed Electrical Field Ablation: Understanding the Benefits and Limitations, Circulation: Arrhythmia and Electrophysiology, vol. 14, No. 9, Sep. 20, 2021.

Xie et al., Ablation of Myocardial Tissue With Nanosecond Pulsed Electric Fields, PLOS ONE, vol. 10, No. 12, Dec. 14, 2015.

Yavin et al., Pulsed Field Ablation Using a Lattice Electrode for Focal Energy Delivery, Circulation: Arrhythmia and Electrophysiology, vol. 13, No. 6, May 6, 2020.

U.S. Appl. No. 17/502,640 Office Action dated Nov. 27, 2023.

* cited by examiner

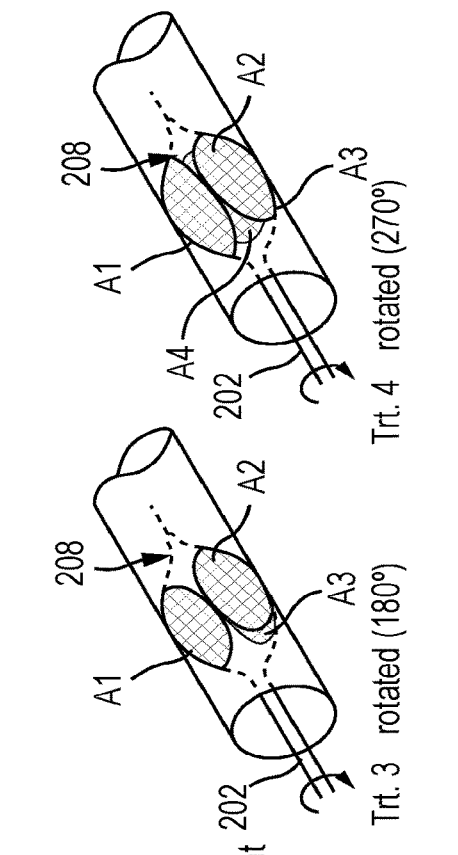
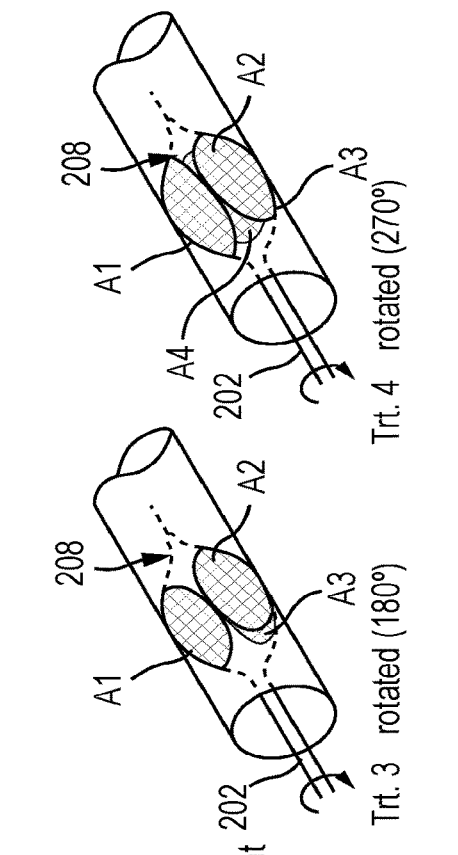
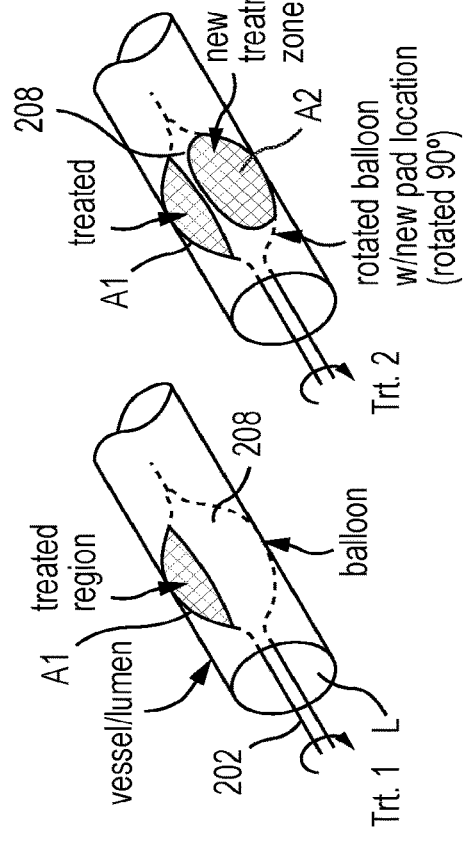
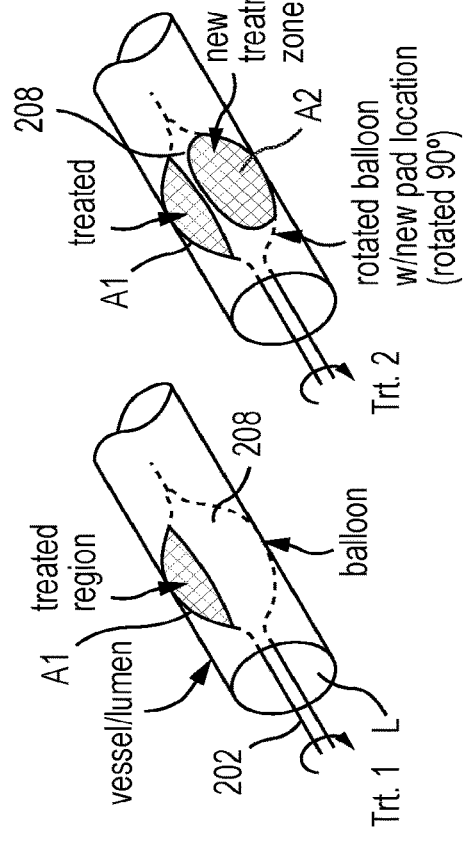
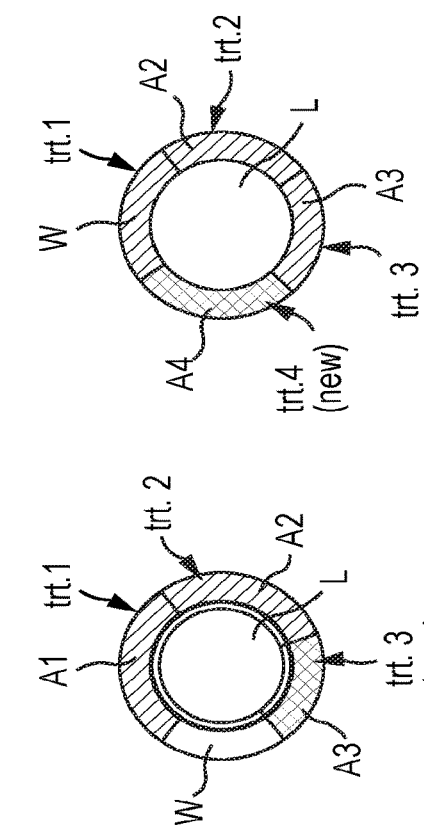
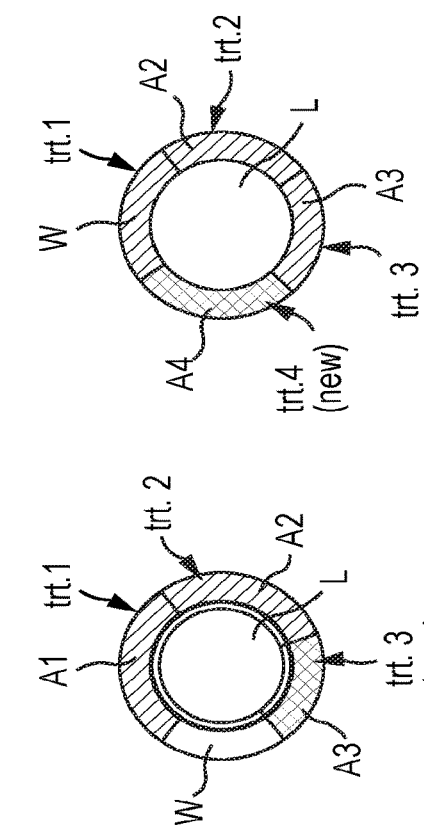
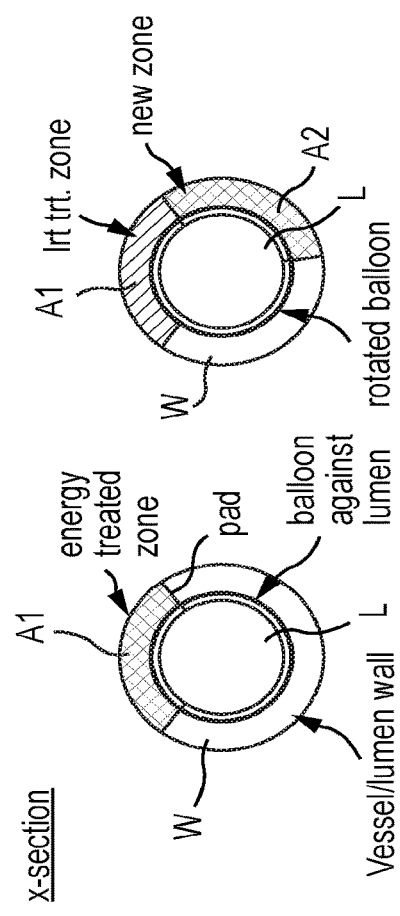
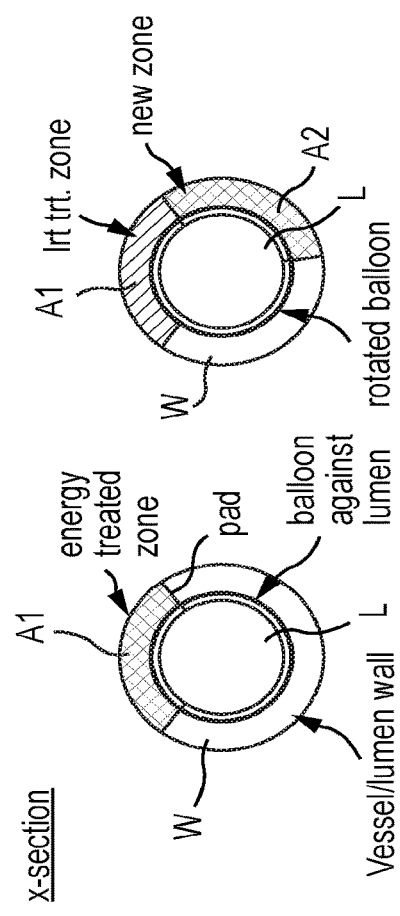

Results:
Electrical Field Distrubtion

Circumferential Contact

Paddle Contact

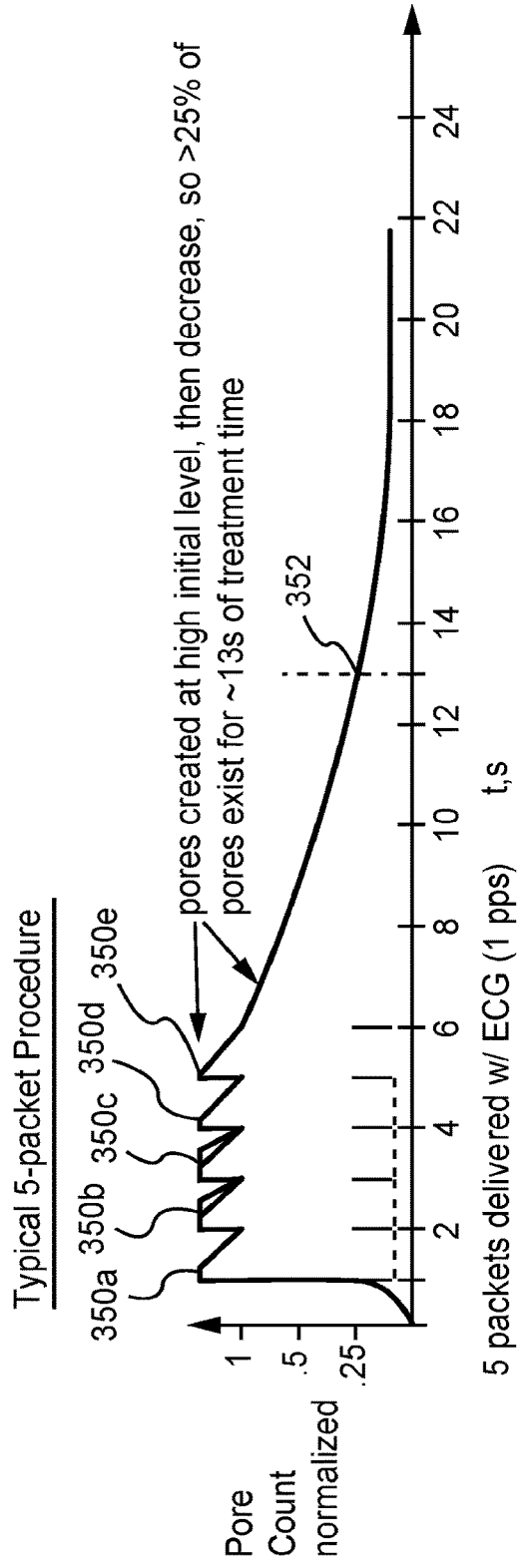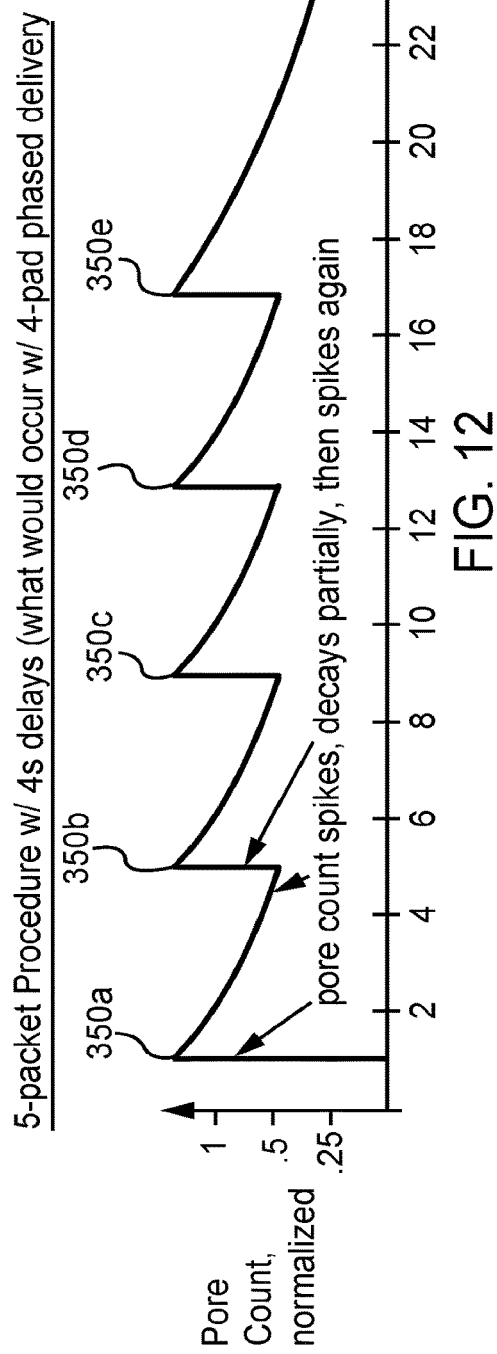
FIG. 11
FIG. 12

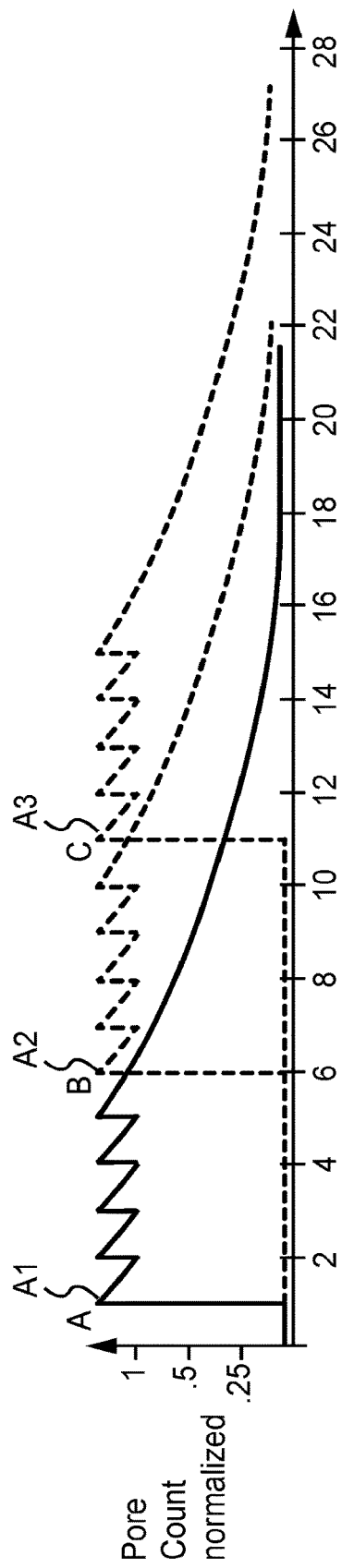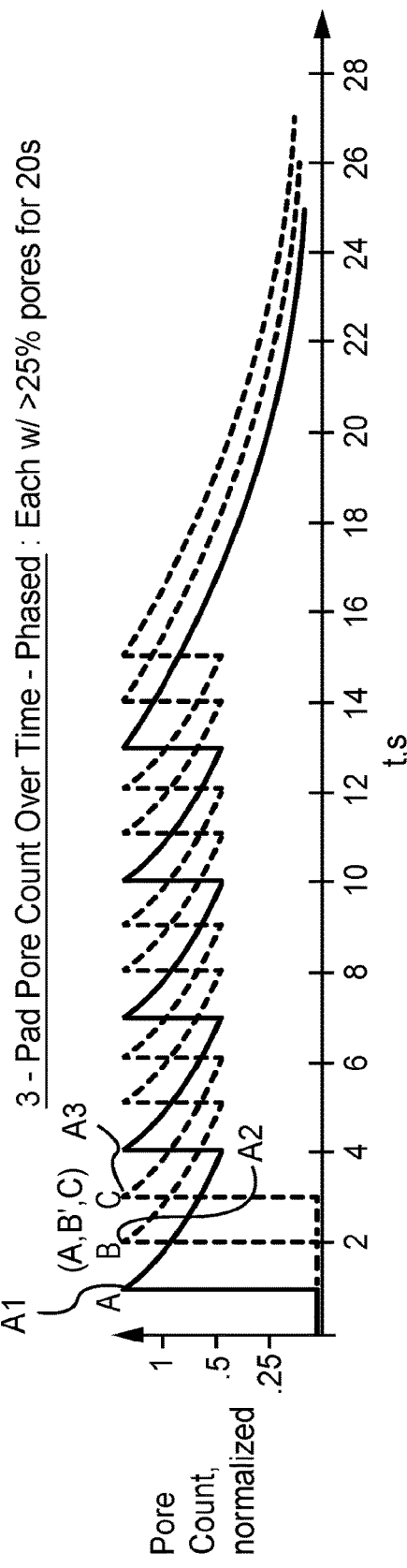

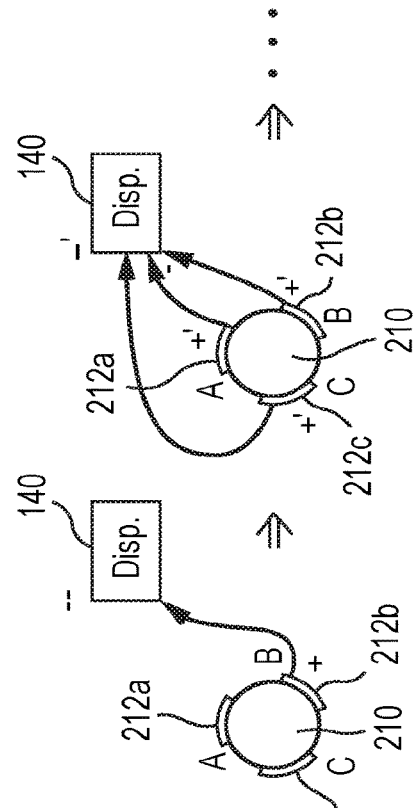
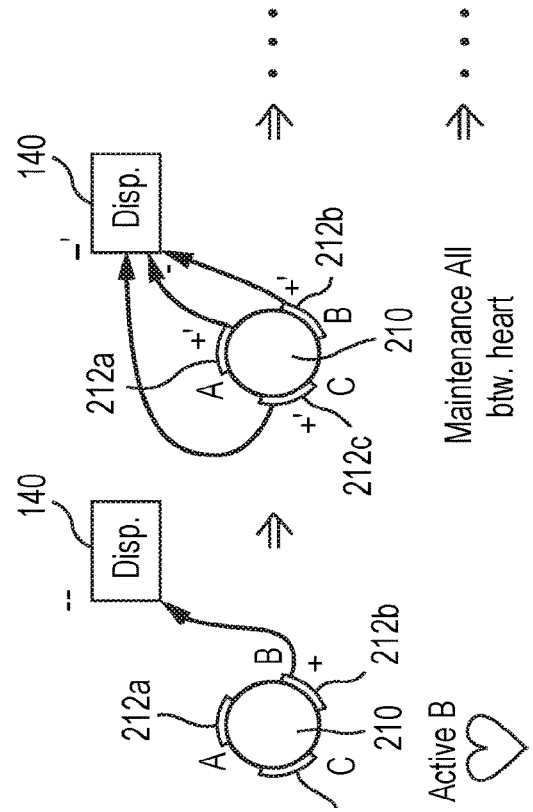
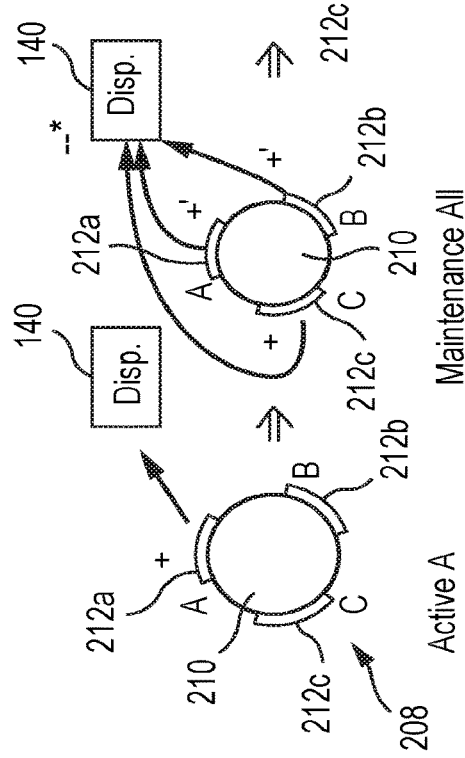
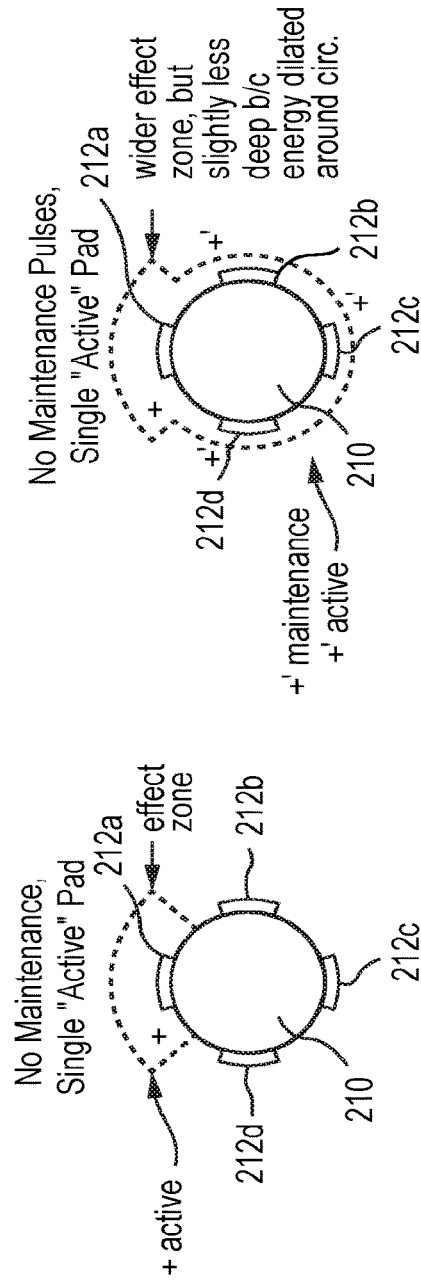

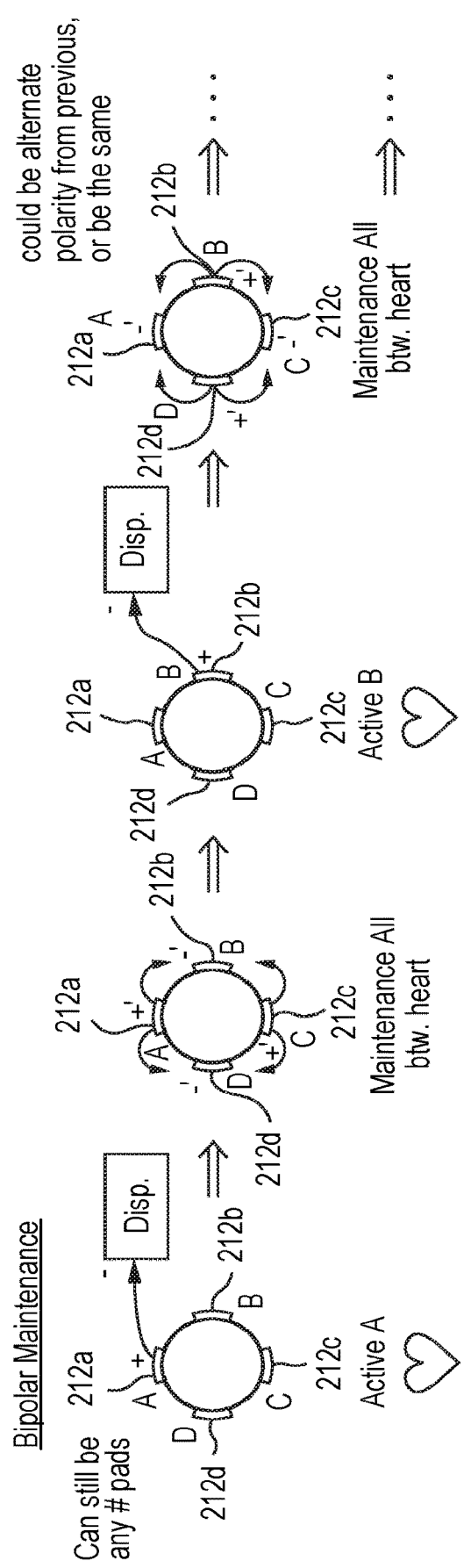

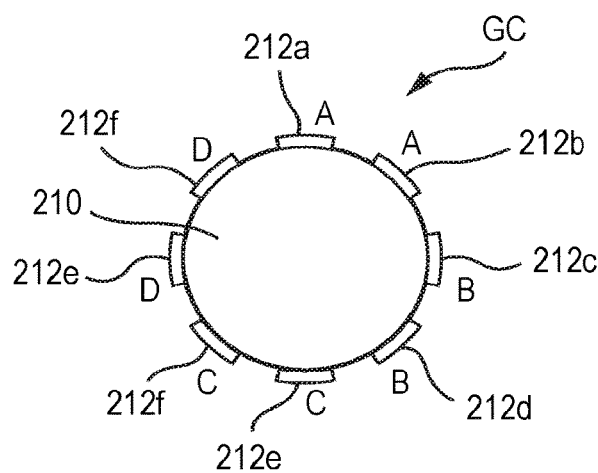
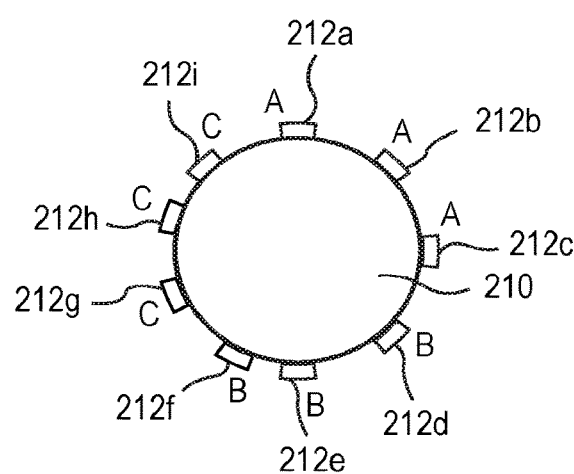
FIG. 21A   FIG. 21B
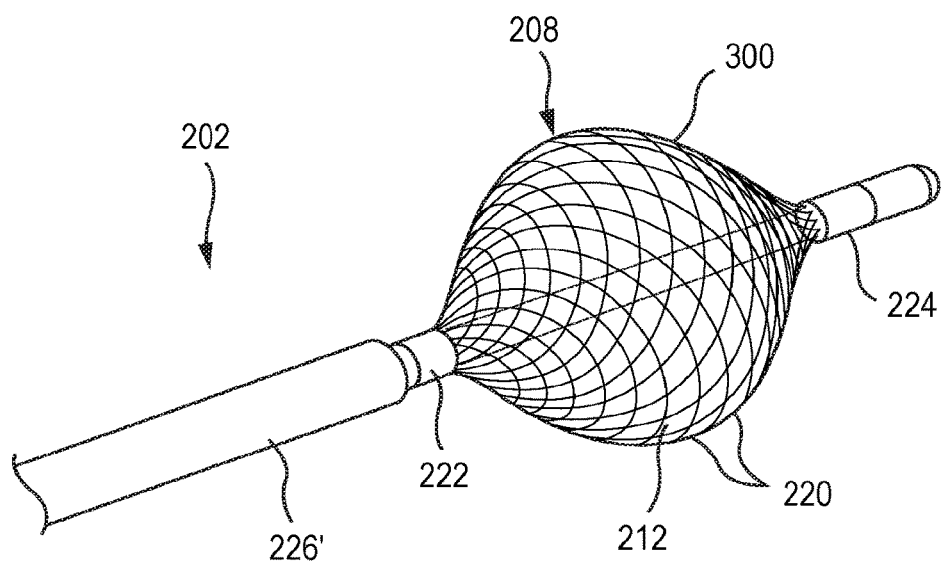
FIG. 22

OPTIMIZATION OF ENERGY DELIVERY FOR VARIOUS APPLICATIONS

CROSS-REFERENCE TO RELATED APPLICATIONS

This application is a continuation of U.S. patent application Ser. No. 16/914,200 issued as U.S. Pat. No. 11,547,851B2, filed Jun. 26, 2020, which is a continuation of PCT Application No. PCT/US2018/067504, filed Dec. 26, 2018, that claims priority to U.S. provisional application No. 62/610,430, filed on Dec. 26, 2017 and to U.S. provisional application No. 62/693,622, filed on Jul. 3, 2018, the entire contents of each of which are hereby incorporated by reference in their entirety.

BACKGROUND

Various devices and methods have been developed to deliver therapeutic energy to the body for the treatment of diseases and afflictions. In some instances, such delivery is to tissues within a body lumen, passageway or similar anatomy, so as to treat diseased tissue along or within the walls of the passageway, or so as to affect diseases which are associated with a passageway or reachable through a passageway. Such devices typically include a flexible elongate shaft, so as to traverse tortuous luminal anatomy, and an energy delivery element mounted thereon to deliver such energy to remote or enclosed locations such as body lumens. Such devices have been developed to treat, for example, passageways of the lungs or blood vessels of the vasculature. Different environments, such as airways versus blood filled environments, and differing diseases, such as those affecting the surface tissues versus those affecting deeper layers or tissues, lead to varying objectives for these devices. At least some of these objectives will be met by embodiments of the present disclosure.

SUMMARY

In a first aspect, a method is provided of treating a passageway within a body wherein the passageway has an inner circumference, the method comprising: positioning a plurality of electrodes within the passageway so that the plurality of electrodes spans the inner circumference of the passageway; creating a first treatment area along a first portion of the inner circumference of the passageway by providing pulsed electric field energy to at least one of the plurality of electrodes so as to prioritize energy delivery through the at least one of the plurality of electrodes to the first treatment area; and creating at least one additional treatment area along at least one additional portion of the inner circumference of the passageway by providing pulsed electric field energy to at least one of the plurality of electrodes so as to prioritize energy delivery through the at least one of the plurality of electrodes to the at least one additional treatment area, wherein the first portion and the at least one additional portion extends along the inner circumference so as to create a functionally continuous treatment area spanning the inner circumference.

In some embodiments, the passageway is disposed within a heart and the functionally continuous treatment area comprises an electrical disconnection between a pulmonary vein and a left atrium so as to treat arrhythmia. Optionally, the passageway comprises the pulmonary vein. In some embodiments, the functionally continuous treatment area comprises a transmural lesion. In other embodiments, the passageway comprises an airway within a lung and the functionally continuous treatment area creates a vacancy of cell types while maintaining a cartilage layer of the airway. In some embodiments, the cell types include epithelial cells, goblet cells and/or submucosal gland cells. In some embodiments, the functionally continuous treatment area has a depth of up to and not beyond 2.5 cm.

In some embodiments, the pulsed electric field energy is biphasic.

In some embodiments, creating the first treatment area along the first portion of the inner circumference of the passageway is achieved by providing pulsed electric field energy to the at least one of the plurality of electrodes for less than or equal to 10,000 us. Optionally, creating the first treatment area along the first portion of the inner circumference of the passageway is achieved by providing pulsed electric field energy to the at least one of the plurality of electrodes for less than or equal to 500 us. Still further, in some embodiments, creating the first treatment area along the first portion of the inner circumference of the passageway is achieved by providing pulsed electric field energy to the at least one of the plurality of electrodes for 5 us-50 us.

In some embodiments, the pulsed electric field energy is comprised of less than or equal to 1000 packets, 40-500 packets, or up to 10 packets. In some embodiments, the pulsed electric field energy is delivered in a monopolar arrangement.

In some embodiments, the at least one additional portion comprises two to seven additional portions.

In some embodiments, the pulsed electric field energy is provided to the plurality of electrodes in a manner so that the first treatment area and the at least one additional treatment areas are created in series. In some embodiments, the first treatment area and the at least one additional treatment areas overlap.

In some embodiments, creating the first treatment area comprises providing the pulsed electric field energy to the first treatment area in a plurality of phases. Optionally, creating the at least one additional treatment areas comprise providing the pulsed electric field energy to the at least one additional treatment areas in a plurality of differing phases, wherein the plurality of phases and the plurality of differing phases do not coincide. In some embodiments, creating the at least one additional treatment areas comprise providing the pulsed electric field energy to the at least one additional treatment areas in a plurality of differing phases, wherein the plurality of phases and the plurality of differing phases form a repetitive pattern. In some embodiments, the method further comprises providing maintenance pulsed electric field energy to the first treatment area and/or the at least one additional treatment areas in between phases, wherein the maintenance pulsed electric field energy has a lower voltage than the pulsed electric field energy. Optionally, the maintenance pulsed electric field energy has a voltage of less than half that of the pulsed electric field energy.

In some embodiments, the plurality of electrodes comprise a plurality of electrodes mounted on or imbedded in an expandable member, wherein positioning the plurality of electrodes comprises expanding the expandable member. In some embodiments, the plurality of electrodes comprises a plurality of wires or ribbons forming an electrode delivery body having an expandable basket shape, wherein a portion of the basket shape is insulated, wherein positioning the plurality of electrodes comprises expanding the electrode delivery body.

In a second aspect, a method is provided for treating a passageway within a body wherein the passageway has an inner circumference, the method comprising: positioning an electrode within the passageway so that the electrode spans a portion of the inner circumference of the passageway; creating a first treatment area along a first portion of the inner circumference of the passageway by providing pulsed electric field energy to the electrode; repositioning the electrode one or more times within the passageway within the passageway so that the electrode spans an addition portion of the inner circumference each time the electrode is repositioned; and creating an additional treatment area along each additional portion of the inner circumference of the passageway by providing a pulsed electric field energy to the repositioned electrode each time the electrode is repositioned, wherein the first portion and each additional portion extend along the inner circumference so as to create a functionally continuous treatment area spanning the inner circumference.

In a third aspect, a system is provided for treating a passageway within a body comprising: a catheter comprising a first electrode and at least one additional electrode disposed near its distal end, wherein the distal end of the catheter is configured to be positioned within the passageway so that the first electrode and the at least one additional electrode are able to transmit pulsed electric field energy to an inner circumference of the passageway; and a generator in electrical communication with the first electrode and the at least one additional electrode, wherein the generator includes at least one energy delivery algorithm that a) provides an electric signal of the pulsed electric field energy to the first electrode so as to prioritize energy delivery through the first electrode to create a first treatment area and b) switches to individually provide an electric signal of the pulsed electric field energy to each of the at least one additional electrodes so as to prioritize energy delivery through each of the at least one additional electrode when provided the electric signal so as to create an additional treatment area corresponding to each of the at least one additional electrodes, wherein the first treatment area and the additional treatment areas extend along the inner circumference of the passageway so as to create a functionally continuous treatment area spanning the inner circumference.

In some embodiments, the passageway is disposed within a heart and the distal end of the catheter is configured to be positioned within the heart, and wherein the at least one energy delivery algorithm includes signal parameters causing the functionally continuous treatment area to comprise an electrical disconnection between a pulmonary vein and a left atrium so as to treat arrhythmia. Optionally, the passageway comprises the pulmonary vein and the distal end of the catheter is configured to be positioned within the pulmonary vein. In some embodiments, the signal parameters cause the functionally continuous treatment area to comprise a transmural lesion.

In some embodiments, the passageway comprises an airway within a lung and the distal end of the catheter is configured to be positioned within the airway, and wherein the at least one energy delivery algorithm includes signal parameters causing the functionally continuous treatment area to comprise a vacancy of cell types while maintaining a cartilage layer of the airway. In some embodiments, the cell types include epithelial cells, goblet cells and/or submucosal gland cells. In some embodiments, the functionally continuous treatment area has a depth of up to and not beyond 2.5 cm.

In some embodiments, the pulsed electric field energy is biphasic. In some embodiments, the at least one energy delivery algorithm provides pulsed electric field energy to the at least one of the plurality of electrodes for less than or equal to 10,000 us to create the first treatment area and/or each of the at least one additional treatment areas. In some embodiments, the at least one energy delivery algorithm provides pulsed electric field energy to the at least one of the plurality of electrodes for less than or equal to 500 us to create the first treatment area and/or each of the at least one additional treatment areas. In some embodiments, the at least one energy delivery algorithm provides pulsed electric field energy to the at least one of the plurality of electrodes for 5 us-50 us to create the first treatment area and/or each of the at least one additional treatment areas.

In some embodiments, the pulsed electric field energy is comprised of less than or equal to 1000 packets, 40-500 packets, or less than or equal to 10 packets.

In some embodiments, the pulsed electric field energy is delivered in a monopolar arrangement. In some embodiments, the at least one additional electrode comprises two to seven additional electrodes. In some embodiments, the at least one energy delivery algorithm provides the electric signal of the pulsed electric field energy to each of the first electrode and at least one additional electrode in series. In some embodiments, the first treatment area and the at least one additional treatment areas overlap.

In some embodiments, the at least one energy delivery algorithm is configured to provide the electric signal of the pulsed electric field energy to the first electrode in a plurality of phases. In some embodiments, the at least one energy delivery algorithm is configured to provide the electric signal of the pulsed electric field energy to the at least one additional electrode in a plurality of differing phases, wherein the plurality of phases and the plurality of differing phases do not coincide. In some embodiments, the plurality of phases and the plurality of differing phases form a repetitive pattern. In some embodiments, the at least one energy delivery algorithm provides maintenance pulsed electric field energy to the first electrode and/or the at least one additional electrode in between phases, wherein the maintenance pulsed electric field energy has a lower voltage than the pulsed electric field energy. In some embodiments, the maintenance pulsed electric field energy has a voltage of less than half that of the pulsed electric field energy.

In some embodiments, the at least a first electrode and the at least one additional electrode are mounted on or imbedded in an expandable member. In some embodiments, the at least a first electrode and the at least one additional electrode comprises a plurality of wires or ribbons forming an electrode delivery body having an expandable basket shape, wherein a portion of the basket shape is insulated.

In a fourth aspect, system is provided for treating a passageway within a body comprising: a catheter comprising at least one electrode disposed near its distal end, wherein the distal end of the catheter is configured to be positioned within the passageway so that the at least one electrode is able to transmit pulsed electric field energy to an inner surface of the passageway; and a generator in electrical communication with the at least one electrode, wherein the generator includes at least one energy delivery algorithm that provides an electric signal to the at least one electrode so that pulsed electric field energy is delivered to cells on the inner surface of the passageway, wherein the electric signal comprises a plurality of packets and wherein each packet comprises a plurality of biphasic cycles and wherein each packet is separated in time by 0.0001 to 10 seconds.

In some embodiments, the plurality of packets generates the pulsed electric field energy for less than or equal to 10,000 us, less than or equal to 500 us, or less than or equal to 5 us-50 us. In some embodiments, the pulsed electric field energy is comprised of less than or equal to 1000 packets, 40-500 packets, or less than or equal to 10 packets. In some embodiments, the pulsed electric field energy is delivered in a monopolar arrangement.

In some embodiments, the at least one electrode comprises at least a first electrode and at least one additional electrode arranged to deliver the pulsed electric field energy to a circumference of the inner surface of the passageway. In some embodiments, the at least one energy delivery algorithm provides the plurality of packets to the first electrode prior to providing another plurality of packets to each of the at least one additional electrode. In some embodiments, the at least one energy delivery algorithm provides the another plurality of packets to each of the at least one additional electrode before the plurality of packets is finished being delivered to the first electrode. In some embodiments, the at least one energy delivery algorithm provides maintenance pulsed electric field energy to the first electrode and/or the at least one additional electrodes in between packets, wherein the maintenance pulsed electric field energy has a lower voltage than the pulsed electric field energy. In some embodiments, the maintenance pulsed electric field energy has a voltage of less than half that of the pulsed electric field energy.

In some embodiments, the system further comprises a cardiac monitor configured to acquire a cardiac signal of the patient, and wherein the generator provides the maintenance pulsed electric field energy in synchronization with the cardiac signal.

In some embodiments, the at least a first electrode and the at least one additional electrode are mounted on or imbedded in an expandable member. In some embodiments, the at least a first electrode and the at least one additional electrode comprises a plurality of wires or ribbons forming an electrode delivery body having an expandable basket shape, wherein a portion of the basket shape is insulated. In some embodiments, the pulsed electric field energy is delivered to cells on the inner surface of the passageway in the manner that disrupts homeostasis of the cells at a depth of up to and not beyond 2.5 cm. In some embodiments, the system further comprises a cardiac monitor configured to acquire a cardiac signal of the patient, and wherein the generator provides the electrical signal in synchronization with the cardiac signal.

In a fifth aspect, a method is provided of treating a passageway within a body wherein the passageway has an inner circumference, the method comprising: positioning a plurality of electrodes within the passageway so that the plurality of electrodes spans at least a portion of the inner circumference of the passageway; creating a first treatment area along a first portion of the inner circumference of the passageway by providing pulsed electric field energy to at least one of the plurality of electrodes so as to prioritize energy delivery through the at least one of the plurality of electrodes to the first treatment area; and creating at least one additional treatment area along at least one additional portion of the inner circumference of the passageway by providing pulsed electric field energy to at least one of the plurality of electrodes so as to prioritize energy delivery through the at least one of the plurality of electrodes to the at least one additional treatment area, wherein the first portion and the at least one additional portion extends along the inner circumference so as to create a balanced treatment area.

In a sixth aspect, a system is provided for treating a passageway within a body comprising: a catheter comprising a first electrode and at least one additional electrode disposed near its distal end, wherein the distal end of the catheter is configured to be positioned within the passageway so that the first electrode and the at least one additional electrode are able to transmit pulsed electric field energy to an inner circumference of the passageway; and a generator in electrical communication with the first electrode and the at least one additional electrode, wherein the generator includes at least one energy delivery algorithm that a) provides an electric signal of the pulsed electric field energy to the first electrode so as to prioritize energy delivery through the first electrode to create a first treatment area and b) switches to individually provide an electric signal of the pulsed electric field energy to each of the at least one additional electrodes so as to prioritize energy delivery through each of the at least one additional electrode when provided the electric signal so as to create an additional treatment area corresponding to each of the at least one additional electrodes, wherein the first treatment area and the additional treatment areas extend along the inner circumference of the passageway so as to create a balanced treatment area.

These and other embodiments are described in further detail in the following description related to the appended drawing figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Example features and advantages of the present disclosure are set forth with reference to the below detailed description, which sets forth illustrative embodiments, in which the principles of the present disclosure are utilized, and the accompanying drawings, of which:

FIGS. 4A-4D illustrate a method of delivering energy to a circumferential ring along a body lumen in a series of steps with the use of an embodiment of a therapeutic energy delivery catheter.

FIGS. 5A-5D illustrate treatment outcomes corresponding to the method of FIGS. 4A-4D.

FIG. 11 is an example plot showing pore or defect formation when PEF energy is delivered in typical intervals that are not optimized for lethality.

FIG. 12 is an example plot showing pore or defect formation when PEF energy packets are delivered in intervals wherein rest periods between each packet are such that subsequent PEFs are delivered close enough to maintain disrupted membranes but far enough apart to increase the cumulative amount of cell contents leakage.

FIG. 14 is an example plot showing the effects of delivering multiple PEF packets (five packets) to each electrode in a serial manner.

FIG. 15 is an example plot showing the effects of delivering a plurality of PEF packets in a sequence that involves delivering the spaced-apart packets in an overlapping pattern to the electrodes, rather than in a serial pattern.

FIGS. 18A-18D illustrate an embodiment of a monopolar energy delivery sequence using maintenance PEFs during various portions of the cardiac cycle.

FIGS. 19A-19B illustrate potential effects of delivering maintenance PEFs to various electrodes simultaneously with a primary PEF to another electrode.

FIGS. 20A-20D illustrate an example delivery of maintenance PEFs in a bipolar fashion, with primary PEFs being delivered in a monopolar fashion.

FIGS. 21A-21B illustrate embodiments by which focal delivery effects can be achieved by delivering energy to more than one electrode.

FIG. 22 illustrates an example insulation material covering a portion of an energy delivery body and leaving another portion exposed, with the exposed portion considered the electrode.

DETAILED DESCRIPTION

Figure 1:
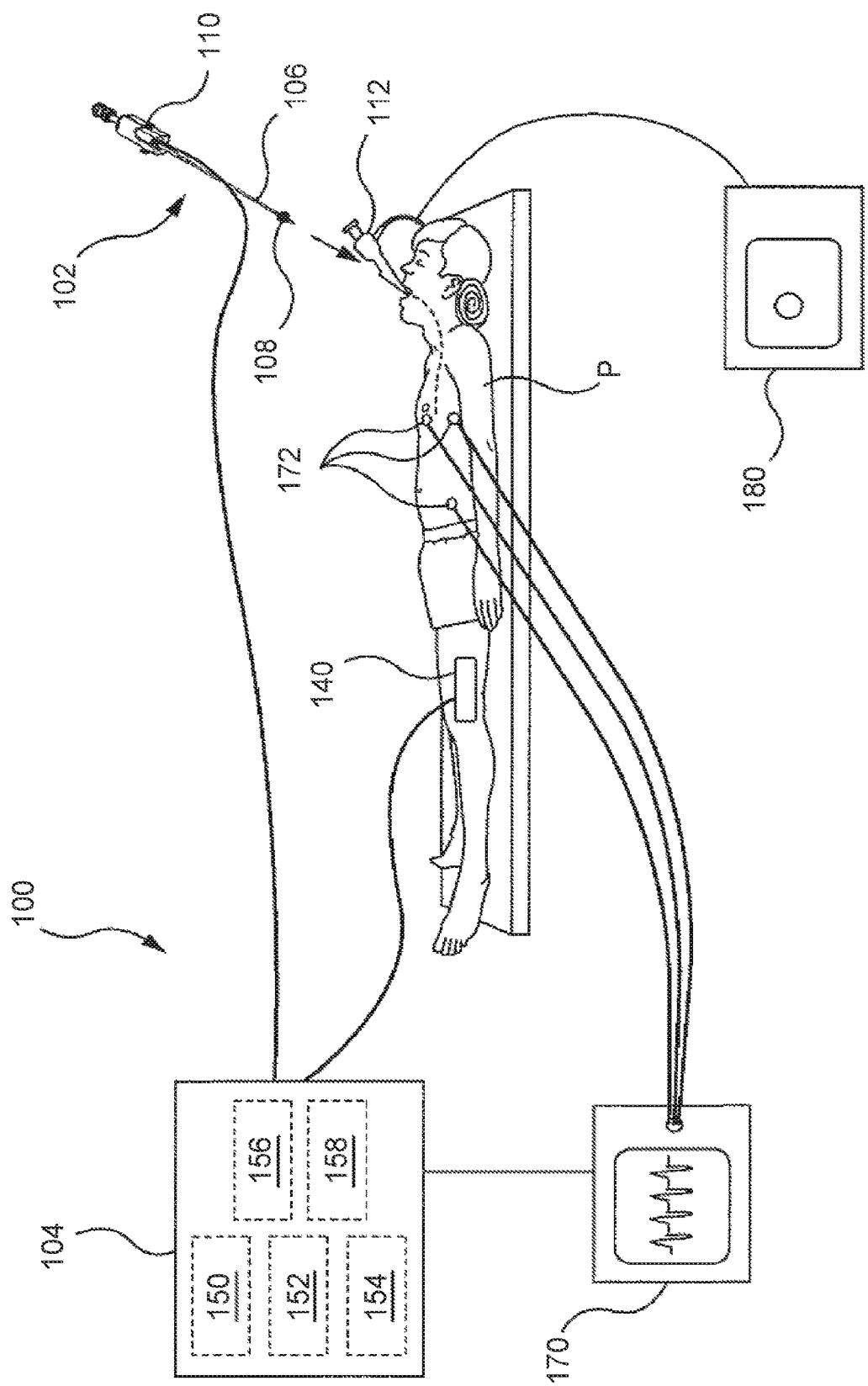
FIG. 1 illustrates an embodiment of an existing known pulmonary tissue modification system suitable for use in the treatment of a patient.

Therapeutic energy can be applied to lung passageways in the treatment of various pulmonary diseases and disorders, such as or associated with chronic obstructive pulmonary disease (COPD) (e.g., chronic bronchitis, emphysema), asthma, interstitial pulmonary fibrosis, cystic fibrosis, bronchiectasis, primary ciliary dyskinesia (PCD), acute bronchitis and/or other pulmonary diseases or disorders. Example pulmonary tissues reachable through the lung passageway include, but are not limited to, the epithelium (the goblet cells, ciliated pseudostratified columnar epithelial cells, and basal cells), lamina propria, submucosa, submucosal glands, basement membrane, smooth muscle, cartilage, nerves, pathogens resident near or within the tissue, or a combination of any or all of the foregoing.

In some instances, the therapeutic energy is generally characterized by high voltage pulses which allow for removal of target tissue with little or no destruction of the tissue-level architectural proteins among the extracellular matrix. This prevents dangerous collateral effects, such as vascular stenosis or esophageal fistula, and also allows for regeneration of healthy new target tissue within days of the procedure. Examples of systems which provide this type of treatment include the pulmonary tissue modification systems (e.g., energy delivery catheter systems) described in commonly assigned patent applications including international patent application number PCT/US2017/039527, titled "GENERATOR AND A CATHETER WITH AN ELECTRODE AND A METHOD FOR TREATING A LUNG PASSAGEWAY," which claims priority to U.S. provisional application Nos. 62/355,164 and 62/489,753, each of which is incorporated herein by reference for all purposes. Although such therapies have been successful, improvements may be desired. For instance, an increased regularity of treatment effect throughout the circumference of an airway lumen may be desired.

Therapeutic energy can also be applied to blood vessels for the treatment of a variety of conditions, including atherosclerosis (particularly in the prevention of restenosis following angioplasty) and atrial fibrillation. Atrial fibrillation is the most common sustained cardiac arrhythmia, and severely increases the risk of mortality in affected patients, particularly by causing stroke. In this phenomenon, the heart is taken out of normal sinus rhythm due to the production of erroneous electrical impulses. Atrial fibrillation is thought to be initiated in the myocardial sleeves of the pulmonary veins (PVs) due to the presence of automaticity in cells within the myocardial tissue of the PVs. Pacemaker activity from these cells is thought to result in the formation of ectopic beats that initiate atrial fibrillation. PVs are also thought to be important in the maintenance of atrial fibrillation because the chaotic architecture and electrophysiological properties of these vessels provides an environment where atrial fibrillation can be perpetuated. Thus, destruction or removal of these aberrant pacemaker cells within the myocardial sleeves of the PVs has been a goal and atrial fibrillation is often treated by delivering therapeutic energy to the pulmonary veins. However, due to reports of PV stenosis, the approach has been conventionally modified to one that targets PV antra to achieve conduction block between the PVs and the left atrium. The PV antra encompass, in addition to the pulmonary veins, the left atrial roof and posterior wall and, in the case of the right pulmonary vein antra, a portion of the interatrial septum. In some instances, this technique offers a higher success rate and a lower complication rate compared with pulmonary vein ostial isolation.

Thermal ablation therapies, especially radiofrequency (RF) ablation, are currently the "gold standard" to treat symptomatic atrial fibrillation by localized tissue necrosis. Despite the improvements in reestablishing sinus rhythm using available methods, both success rate and safety are limited by the thermal nature of these procedures. Thus, while keeping the technique in clinical practice, safer and more versatile methods of removing abnormal tissue have been used, including irreversible electroporation (IRE), a therapy based on the unrecoverable permeabilization of cell membranes caused by short pulses of high voltage energy. IRE has been found to be tissue-specific, triggering apoptosis rather than necrosis, and safer for the structures adjacent the myocardium. However, thus far, the success of these IRE methodologies has been heterogeneous.

In some instances, the delivery of IRE energy has resulted in incomplete block of the aberrant electrical rhythms. This may be due to irregularity of treatment circumferentially around the pulmonary veins and/or lack of transmural delivery of energy. In either case, atrial fibrillation is not sufficiently treated or atrial fibrillation recurs at a later time. Therefore, improvements in atrial fibrillation treatment are desired.

It will be appreciated that therapeutic energy may be applied to a variety of body lumens to treat a number of particular diseases and conditions. In some instances, the environment or the characteristics of a disease are such that improvement in the delivery of energy from current devices and/or improved devices and methods is desired. As mentioned, in some instances improved depth of energy delivery is desired, and, in other instances, improved circumferential delivery to the luminal walls is desired, or some combination of the two. Likewise, in other instances, improved control of delivery, such as a reduction in spatial or cumulative distortions of energy delivery or unanticipated shifts in delivery direction due to various heterogeneities or other environmental factors, is desired. Such improvements are typically desired while maintaining or reducing the total energy delivered and maintaining or reducing the procedure time. This can assist, for example, in managing costs and side effects. At least some of the foregoing objectives are achievable by embodiments of the present disclosure.

Specific embodiments of the disclosed device, delivery system, and method will now be described with reference to the drawings. Nothing in this detailed description is intended to imply that any particular component, feature, or step is essential to any embodiment.

I. Overview

Methods, devices and systems are provided for optimized delivery of therapeutic energy to portions of the body, particularly body lumens, in a manner that improves outcomes under various conditions. In particular, specialized catheter designs and/or distinct energy delivery algorithms are provided for use with tissue modification systems. Examples of such tissue modification systems include the pulmonary tissue modification systems described in commonly assigned international patent application PCT/US2017/039527, titled "GENERATOR AND A CATHETER WITH AN ELECTRODE AND A METHOD FOR TREATING A LUNG PASSAGEWAY," which claims priority to U.S. provisional application Nos. 62/355,164 and 62/489,753, and commonly assigned international patent application PCT/US2018/067501, titled "METHODS, APPARATUSES, AND SYSTEMS FOR THE TREATMENT OF DISEASE STATES AND DISORDERS," which claims priority to U.S. provisional application No. 62/610,430, all of which are incorporated herein by reference for all purposes. These catheter designs and energy delivery algorithms provide energy delivery to lung passageways with improved outcomes for certain conditions. Likewise, these catheter designs and energy delivery algorithms allow aspects of the pulmonary tissue modification system to be utilized in the treatment of other body lumens, such as blood vessels, in particular for the treatment of atrial fibrillation.

Figure 2:
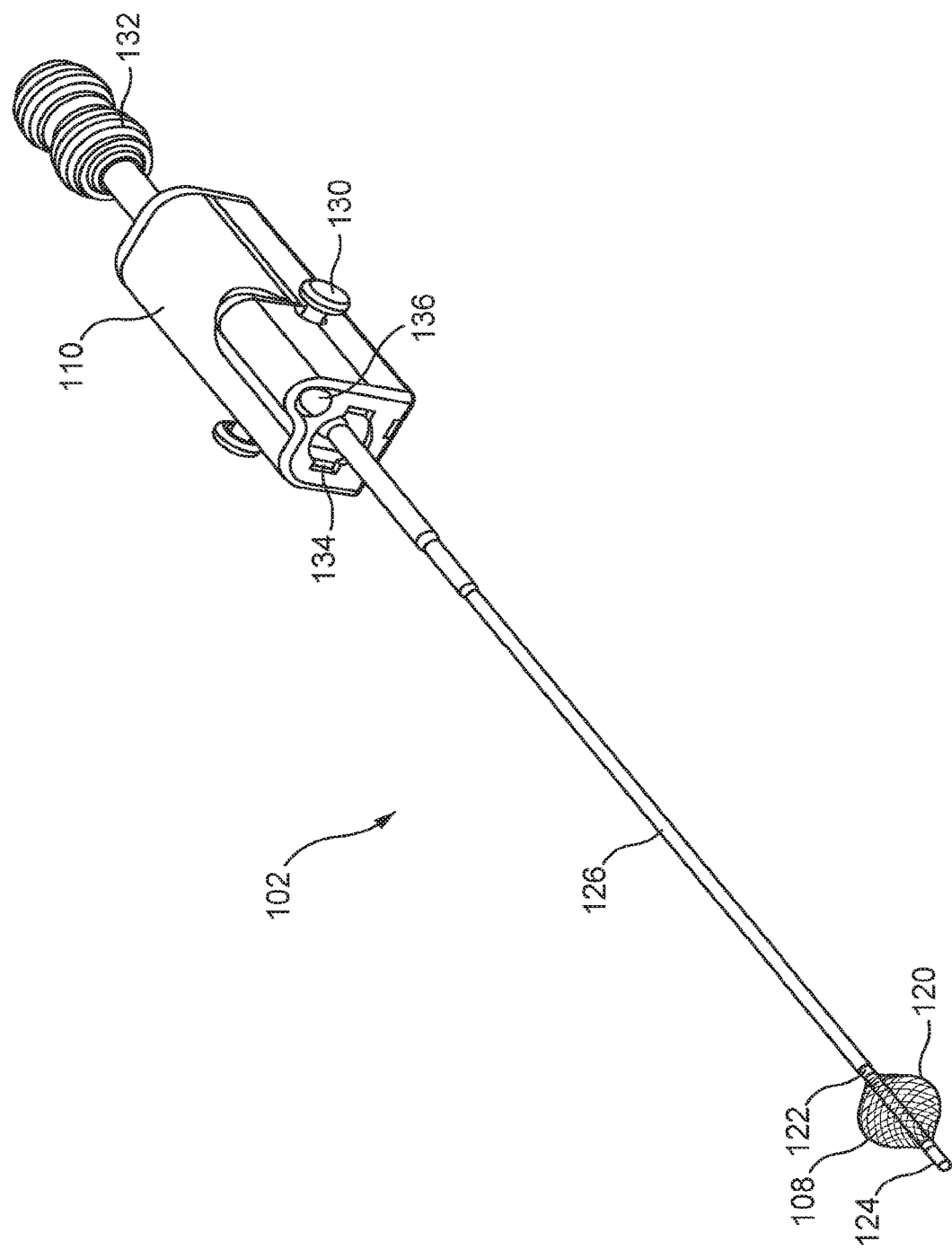
FIG. 2 provides a closer view of the therapeutic energy delivery catheter of FIG. 1.

FIGS. 1-2 illustrate an embodiment of a pulmonary tissue modification system 100 used in treatment of a body lumen or passageway in a patient P. In this embodiment, the system 100 includes a therapeutic energy delivery catheter 102 connectable to a generator 104. In this embodiment, the catheter 102 has an elongate shaft 106 with at least one energy delivery body 108 near its distal end and a handle 110 at its proximal end. Connection of the catheter 102 to the generator 104 provides electrical energy to the energy delivery body 108, among other features. The catheter 102 is insertable into bronchial passageways of a patient P by a variety of methods, such as through a lumen in a bronchoscope 112, as illustrated in FIG. 1.

FIG. 2 provides a closer view of the embodiment of the therapeutic energy delivery catheter 102 of FIG. 1. In this embodiment, the energy delivery body 108 includes a single monopolar delivery electrode. The energy delivery body 108 includes a plurality of wires or ribbons 120, constrained by a proximal end constraint 122 and a distal end constraint 124, and forms a spiral-shaped basket serving as an electrode. In an alternative embodiment, the wires or ribbons are straight instead of formed into a spiral-shape (i.e., configured to form a straight-shaped basket). In still another embodiment, the energy delivery body 108 is laser cut from a tube. In some embodiments, the energy delivery body 108 is self-expandable and delivered to a targeted area in a collapsed configuration. This collapsed configuration can be achieved, for example, by placing a sheath 126 over the energy delivery body 108. In FIG. 2, the catheter shaft 106 (within the sheath 126) terminates at the proximal end constraint 122, leaving the distal end constraint 124 essentially unconstrained and free to move relative to the shaft 106 of the catheter 102. Advancing the sheath 126 over the energy delivery body 108 allows the distal end constraint 124 to move forward, thereby lengthening/collapsing and constraining the energy delivery body 108.

As shown in this example, the catheter 102 includes a handle 110 at its proximal end. In some embodiments, the handle 110 is removable, such as by pressing a handle removal button 130. In this embodiment, the handle 110 includes an energy delivery body manipulation knob 132 wherein movement of the knob 132 causes expansion or retraction/collapse of the basket-shaped electrode. In this example, the handle 110 also includes a bronchoscope working port snap 134 for connection with the bronchoscope 112 and a cable plug-in port 136 for connection with the generator 104.

Referring back to FIG. 1, in this embodiment, the therapeutic energy delivery catheter 102 is connectable with the generator 104 along with a dispersive (return) electrode 140 applied externally to the skin of the patient P. Thus, in this embodiment, monopolar energy delivery is achieved by supplying energy between the energy delivery body 108 disposed near the distal end of the catheter 102 and the return electrode 140. It will be appreciated, however, that bipolar energy delivery and other arrangements may alternatively be used. When using bipolar energy delivery, the therapeutic energy delivery catheter 102 may differ in overall design, such as to include a plurality of energy delivery bodies 108, or may appear similar in overall design, such as to include a single energy delivery body 108 which is configured to function in a bipolar manner. In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can spread the treatment effect over a larger surface area thus requiring a lower voltage to achieve the treatment effect, compare to monopolar. Likewise, this lower voltage may be used to reduce the depth of penetration. In addition, lower voltage requirements may obviate the use of cardiac synchronization if the delivered voltage is low enough to avoid stimulation of the cardiac muscle cells.

The generator 104 of FIG. 1 includes a user interface 150, one or more energy delivery algorithms 152, a processor 154, a data storage/retrieval unit 156 (such as a memory and/or database), and an energy-storage sub-system 158 which generates and stores the energy to be delivered. In some embodiments, one or more capacitors are used for energy storage/delivery, however any other suitable energy storage element may be used. In addition, one or more communication ports are included.

In some embodiments, the generator 104 includes three sub-systems: 1) a high-energy storage system, 2) a high-voltage, medium-frequency switching amplifier, and 3) the system controller, firmware, and user interface. The system controller includes a cardiac synchronization trigger monitor that allows for synchronizing the pulsed energy output to the patient's cardiac rhythm. The generator takes in alternating current (AC) mains to power multiple direct current (DC) power supplies. The generator's controller can cause the DC power supplies to charge a high-energy capacitor storage bank before energy delivery is initiated. At the initiation of therapeutic energy delivery, the generator's controller, high-energy storage banks and a bi-phasic pulse amplifier can operate simultaneously to create a high-voltage, medium frequency output.

It will be appreciated that a multitude of generator electrical architectures may be employed to execute the energy delivery algorithms. In particular, in some embodiments, advanced switching systems are used which are capable of directing the pulsed electric field circuit to the energy delivering electrodes separately from the same energy storage and high voltage delivery system. Further, generators employed in advanced energy delivery algorithms employing rapidly varying pulse parameters (e.g., voltage, frequency, etc.) or multiple energy delivery electrodes may utilize modular energy storage and/or high voltage systems, facilitating highly customizable waveform and geographical pulse delivery paradigms. It should further be appreciated that the electrical architecture described herein above is for example only, and systems delivering pulsed electric fields may or may not include additional switching amplifier components.

The user interface 150 can include a touch screen and/or more traditional buttons to allow for the operator to enter patient data, select a treatment algorithm (e.g., energy delivery algorithm 152), initiate energy delivery, view records stored on the storage/retrieval unit 156, and/or otherwise communicate with the generator 104.

In some embodiments, the user interface 150 is configured to receive operator-defined inputs. The operator-defined inputs can include a duration of energy delivery, one or more other timing aspects of the energy delivery pulse, power, and/or mode of operation, or a combination thereof. Example modes of operation can include (but are not limited to): system initiation and self-test, operator input, algorithm selection, pre-treatment system status and feedback, energy delivery, post energy delivery display or feedback, treatment data review and/or download, software update, or any combination or subcombination thereof.

In some embodiments, the system 100 also includes a mechanism for acquiring an electrocardiogram (ECG), such as an external cardiac monitor 170. Example cardiac monitors are available from AccuSync Medical Research Corporation. In some embodiments, the external cardiac monitor 170 is operatively connected to the generator 104. The cardiac monitor 170 can be used to continuously acquire an ECG signal. External electrodes 172 may be applied to the patient P to acquire the ECG. The generator 104 analyzes one or more cardiac cycles and identifies the beginning of a time period during which it is safe to apply energy to the patient P, thus providing the ability to synchronize energy delivery with the cardiac cycle. In some embodiments, this time period is within milliseconds of the R wave (of the ECG QRS complex) to avoid induction of an arrhythmia, which could occur if the energy pulse is delivered on a T wave. It will be appreciated that such cardiac synchronization is typically utilized when using monopolar energy delivery, however it may be utilized as part of other energy delivery methods.

In some embodiments, the processor 154, among other activities, modifies and/or switches between the energy-delivery algorithms, monitors the energy delivery and any sensor data, and reacts to monitored data via a feedback loop. In some embodiments, the processor 154 is configured to execute one or more algorithms for running a feedback control loop based on one or more measured system parameters (e.g., current), one or more measured tissue parameters (e.g., impedance), and/or a combination thereof.

The data storage/retrieval unit 156 stores data related to the treatments delivered and can optionally be downloaded by connecting a device (e.g., a laptop or thumb drive) to a communication port. In some embodiments, the device has local software used to direct the download of information, such as, for example, instructions stored on the data storage/retrieval unit 156 and executable by the processor 154. In some embodiments, the user interface 150 allows for the operator to select to download data to a device and/or system such as, but not limited to, a computer device, a tablet, a mobile device, a server, a workstation, a cloud computing apparatus/system, and/or the like. The communication ports, which can permit wired and/or wireless connectivity, can allow for data download, as just described but also for data upload such as uploading a custom algorithm or providing a software update.

As described herein, a variety of energy delivery algorithms 152 are programmable, or can be pre-programmed, into the generator 104, such as stored in memory or data storage/retrieval unit 156. Alternatively, energy delivery algorithms can be added into the data storage/retrieval unit to be executed by processor 154. Each of these algorithms 152 may be executed by the processor 154. In some embodiments, the catheter 102 includes one or more sensors 160 that can be used to determine temperature, impedance, resistance, capacitance, conductivity, permittivity, and/or conductance, to name a few. Sensor data can be used to plan the therapy, monitor the therapy and/or provide direct feedback via the processor 154, which can then alter the energy-delivery algorithm 152. For example, impedance measurements can be used to determine not only the initial dose to be applied but can also be used to determine the need for further treatment, or not.

It will be appreciated that the system 100 can include an automated treatment delivery algorithm that could dynamically respond and adjust and/or terminate treatment in response to inputs such as temperature, impedance at various voltages or AC frequencies, treatment duration or other timing aspects of the energy delivery pulse, treatment power and/or system status.

In some embodiments, imaging is achieved with the use of a commercially-available system, such as a bronchoscope 112 connected with a separate imaging screen 180, as illustrated in FIG. 1. It will be appreciated that imaging modalities can be incorporated into the catheter 102 or used alongside or in conjunction with the catheter 102. The imaging modality can be mechanically, operatively, and/or communicatively coupled to the catheter 102 using any suitable mechanism.

II. Energy Delivery Algorithms

As mentioned previously, one or more energy delivery algorithms 152 are programmable, or can be pre-programmed, into the generator 104 for delivery to the patient P. The one or more energy delivery algorithms 152 specify electric signals which provide energy delivered to the airway walls W which are non-thermal (e.g. below a threshold for thermal ablation; below a threshold for inducing coagulative thermal damage), reducing or avoiding inflammation, and preventing denaturation of stromal proteins. In general, the algorithm 152 is tailored to affect tissue to a pre-determined depth and/or to target specific types of cellular responses to the energy delivered. It may be appreciated that depth and/or targeting may be affected by parameters of the energy signal prescribed by the one or more energy delivery algorithms 152, the design of the catheter 102 (particularly the one or more energy delivery bodies 108), and/or the choice of monopolar or bipolar energy delivery. Typically, depths of up to 0.01 mm, up to 0.02 mm, 0.01-0.02 mm, up to 0.03 mm, 0.03-0.05 mm, up to 0.05 mm, up to 0.08 mm, up to 0.09 mm, up to 0.1 mm, up to 0.2 mm, up to 0.5 mm, up to 0.7 mm, up to 1.0 mm, up to 1.5 mm, up to 2.0 mm, or up to 2.3 mm or less than 2.3 mm can be targeted, particularly when treating a lining of an airway or lung passageway. In some instances, the targeted pre-determined depth is 0.5 mm, such as when targeting airway epithelium and submucosal glands, with significant margin of safety to prevent any morbidity-associated cartilage effects at depths of 2.3 mm. In other instances, the targeted effect depth is more assertive to treat all of the airway epithelial cells and submucosal glands to a depth of up to 1.36 mm, while still preventing safety-associated effects to cartilage at depths of 2.3 mm. In other embodiments, such as when applying such treatment to another clinical application, such as a cardiac application, the algorithm 152 is tailored to affect tissue to deeper pre-determined depths such as up to 0.1 cm, up to 0.2 cm, up to 0.3 cm, up to 0.5 cm, up to 0.8 cm, up to 0.9 cm, up to 1 cm or 0.5 cm to 1 cm. In yet other embodiments, such as when applying such treatment to clinical applications involving even deeper targets, the algorithm 152 is tailored to affect tissue to even deeper pre-determined depths such as of up to 2 cm or up to 2.5 cm In some instances, bipolar energy delivery allows for the use of a lower voltage to achieve the treatment effect, as compared to monopolar energy delivery. In a bipolar configuration, the positive and negative poles are close enough together to provide a treatment effect both at the electrode poles and in-between the electrode poles. This can concentrate the treatment effect over a specific tissue area thus involving a lower voltage to achieve the treatment effect compared to monopolar. Likewise, this focal capability using lower voltages, may be used to reduce the depth of penetration, such as to affect the epithelial cells rather than the submucosal cells. In other instances, this reduced effect penetration depth may be used to focus the energy such as to target epithelial and submucosal layers, while sparing the deeper cartilage tissue. In addition, lower voltage requirements may obviate the use of cardiac synchronization if the delivered voltage is low enough to avoid stimulation of the cardiac muscle cells.

It may be appreciated that a variety of energy delivery algorithms 152 may be used. In some embodiments, the algorithm 152 prescribes a signal having a waveform comprising a series of energy packets wherein each energy packet comprises a series of high voltage pulses. In such embodiments, the algorithm 152 specifies parameters of the signal such as energy amplitude (e.g., voltage) and duration of applied energy, which is comprised of the number of packets, number of pulses within a packet, and the fundamental frequency of the pulse sequence, to name a few. Additional parameters may include switch time between polarities in biphasic pulses, dead time between biphasic cycles, and rest time between packets, which will be described in more detail in later sections. There may be a fixed rest period between packets, or packets may be gated to the cardiac cycle and are thus variable with the patient's heart rate. There may be a deliberate, varying rest period algorithm or no rest period may also be applied between packets. A feedback loop based on sensor information and an auto-shutoff specification, and/or the like, may be included.

Figure 3A:
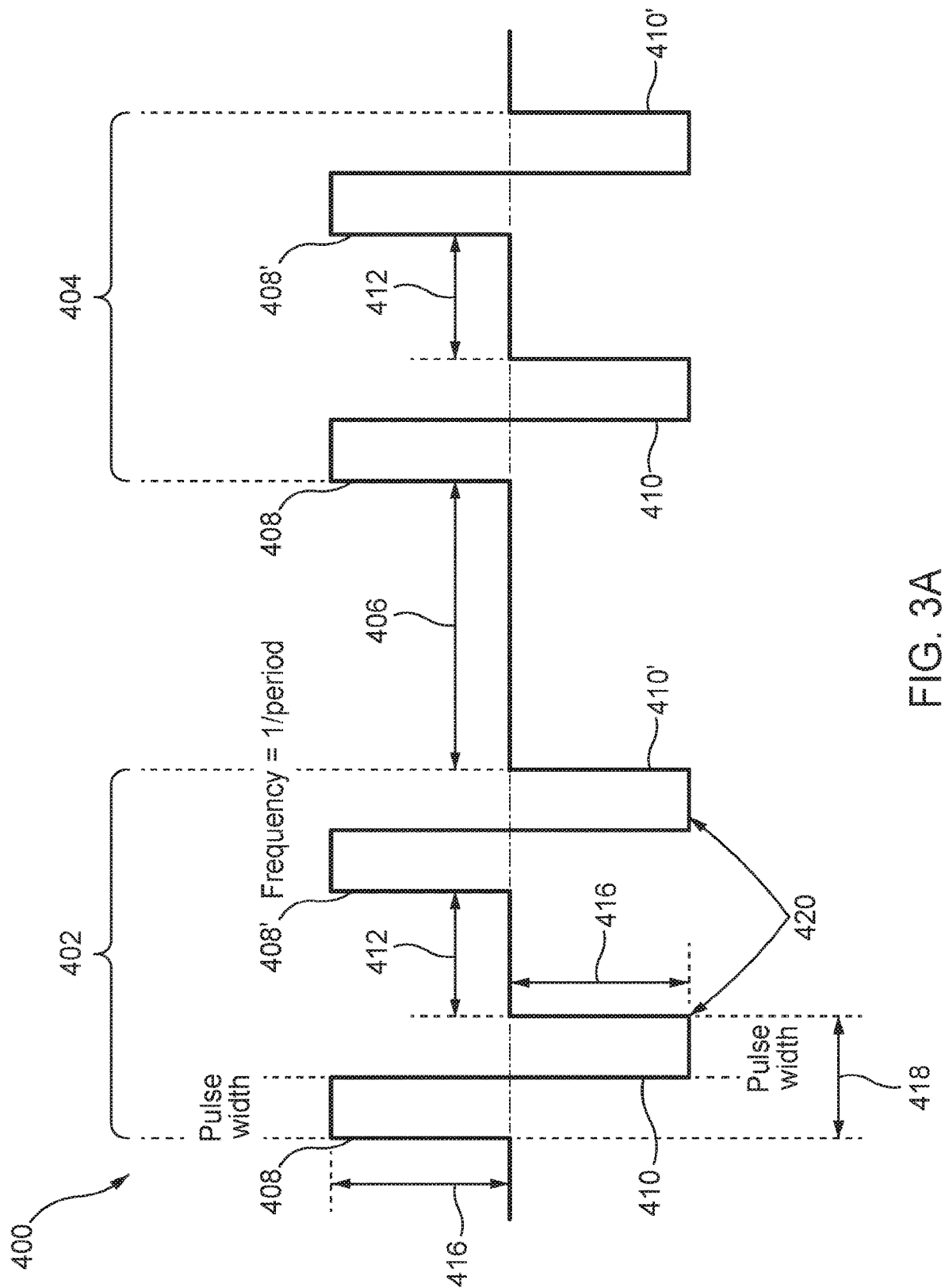
FIG. 3A illustrates an embodiment of a waveform of a signal provided by an energy delivery algorithm.

FIG. 3A illustrates an embodiment of a waveform 400 of a signal prescribed by an energy delivery algorithm 152. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 and a first negative pulse peak 410) and a second biphasic cycle (comprising a second positive pulse peak 408' and a second negative pulse peak 410'). The first and second biphasic pulses are separated by dead time 412 (i.e., a pause) between each pulse. In this embodiment, the biphasic pulses are symmetric so that the set voltage 416 is the same for the positive and negative peaks. Here, the biphasic, symmetric waves are also square waves such that the magnitude and time of the positive voltage wave is approximately equal to the magnitude and time of the negative voltage wave. When using a bipolar configuration, portions of the airway wall W cells facing the negative voltage wave undergo cellular depolarization in these regions, where a normally negatively charged cell membrane region briefly turns positive. Conversely, portions of the airway wall W cells facing the positive voltage wave undergo hyperpolarization in which the cell membrane region's electric potential becomes extremely negative. It may be appreciated that in each positive or negative phase of the biphasic pulse, portions of the airway wall W cells will experience the opposite effects. For example, portions of cell membranes facing the negative voltage will experience depolarization, while the portions 180° to this portion will experience hyperpolarization. In some embodiments, the hyperpolarized portion faces the dispersive or return electrode 140.

A. Voltage

The voltages used and considered may be the tops of square-waveforms, may be the peaks in sinusoidal or sawtooth waveforms, or may be the RMS voltage of sinusoidal or sawtooth waveforms. In some embodiments, the energy is delivered in a monopolar fashion and each high voltage pulse or the set voltage 416 is between about 500 V to 10,000 V, particularly about 500 V to 5000 V, about 500 V to 4000 V, about 1000 V to 4000 V, about 2500 V to 4000V, about 2000 to 3500, about 2000 V to 2500V, about 2500 V to 3500 V, including all values and subranges in between including about 500 V, 1000 V, 1500 V, 2000 V, 2500 V, 3000 V, 3500 V, 4000 V. In some embodiments, each high voltage pulse is in range of approximately 1000 V to 2500 V which can penetrate the airway wall W in particular parameter combinations so as to treat or affect particular cells somewhat shallowly, such as epithelial cells. In some embodiments, each high voltage pulse is in the range of approximately 2500 V to 4000 V which can penetrate the airway W in particular parameter combinations so as to treat or affect particular cells somewhat deeply positioned, such as submucosal cells or smooth muscle cells.

It may be appreciated that the set voltage 416 may vary depending on whether the energy is delivered in a monopolar or bipolar fashion. In bipolar delivery, a lower voltage may be used due to the smaller, more directed electric field. In some embodiments, the energy is delivered in a bipolar fashion and each pulse is in the range of approximately 100 V to 1900 V, particularly 100 V to 999 V, more particularly approximately 500 V to 800 V, such as 500 V, 550 V, 600 V, 650 V, 700 V, 750 V, 800 V. In other embodiments, the energy is delivered in a bipolar fashion and each pulse is between approximately 50 and 5000 volts, including 250 to 1500 volts.

The bipolar voltage selected for use in therapy is dependent on the separation distance of the electrodes, whereas the monopolar electrode configurations that use a distant dispersive pad electrode may be delivered with less consideration for exact placement of the catheter electrode and dispersive electrode placed on the body. In monopolar electrode embodiments, larger voltages are typically used due to the dispersive behavior of the delivered energy through the body to reach the dispersive electrode, on the order of 10 cm to 100 cm effective separation distance. Conversely, in bipolar electrode configurations, the relatively close active regions of the electrodes, on the order of 0.5 mm to 10 cm, including 1 mm to 1 cm, results in a greater influence on electrical energy concentration and effective dose delivered to the tissue from the separation distance. For instance, if the targeted voltage-to-distance ratio is 3000 V/cm to evoke the desired clinical effect at the appropriate tissue depth (1.3 mm), if the separation distance is changed from 1 mm to 1.2 mm, this would result in a necessary increase in treatment voltage from 300 to about 360 V, a change of 20%.

B. Frequency

The number of biphasic cycles per second of time is the frequency. In some embodiments, biphasic pulses are utilized to reduce undesired muscle stimulation, particularly cardiac muscle stimulation. In other embodiments, the pulse waveform is monophasic, and there is no clear inherent frequency, and instead a fundamental frequency may be considered by doubling the monophasic pulse length to derive the frequency. In some embodiments, the signal has a frequency in the range 100 kHz-1 MHz, more particularly 100 kHz-1000 kHz. In some embodiments, the signal has a frequency in the range of approximately 100-600 kHz which typically penetrates the airway W so as to treat or affect particular cells somewhat deeply positioned, such as submucosal cells or smooth muscle cells. In some embodiments, the signal has a frequency in range of approximately 600 kHz-1000 kHz or 600 kHz-1 MHz which typically penetrates the airway wall W so as to treat or affect particular cells somewhat shallowly, such as epithelial cells. It may be appreciated that at some voltages, frequencies at or below 300 kHz may cause undesired muscle stimulation. Therefore, in some embodiments, the signal has a frequency in the range of 400-800 kHz or 500-800 kHz, such as 500 kHz, 550 kHz, 600 kHz, 650 kHz, 700 kHz, 750 kHz, 800 kHz. In particular, in some embodiments, the signal has a frequency of 600 kHz. In addition, cardiac synchronization is typically utilized to reduce or avoid undesired cardiac muscle stimulation during sensitive rhythm periods. It may be appreciated that even higher frequencies may be used with components which minimize signal artifacts.

C. Voltage-Frequency Balancing

The frequency of the waveform delivered may vary relative to the treatment voltage in synchrony to retain adequate treatment effect. Such synergistic changes would include the decrease in frequency, which evokes a stronger effect, combined with a decrease in voltage, which evokes a weaker effect. For instance, in some cases the treatment may be delivered using 3000 V in a monopolar fashion with a waveform frequency of 800 kHz, while in other cases the treatment may be delivered using 2000 V with a waveform frequency of 400 kHz.

When used in opposing directions, the treatment parameters may be manipulated in a way that makes it too effective, which may increase muscle contraction likelihood or risk effects to undesirable tissues, such as cartilage for airway treatments. For instance, if the frequency is increased and the voltage is decreased, such as the use of 2000 V at 800 kHz, the treatment may not have sufficient clinical therapeutic benefit. Opposingly, if the voltage was increased to 3000 V and frequency decreased to 400 kHz, there may be undesirable treatment effect extent to cartilage tissues or other collateral sensitive tissues. In some cases, the overtreatment of these undesired tissues could result in morbidity or safety concerns for the patient.

D. Packets

As mentioned, the algorithm 152 prescribes a signal having a waveform comprising a series of energy packets wherein each energy packet comprises a series of high voltage pulses. The cycle count 420 is half the number of pulses within each biphasic packet. Referring to FIG. 3A, the first packet 402 has a cycle count 420 of two (i.e. four biphasic pulses). In some embodiments, the cycle count 420 is set between 1 and 100 per packet, including all values and subranges in between. In some embodiments, the cycle count 420 is up to 5 pulses, up to 10 pulses, up to 25 pulses, up to 40 pulses, up to 60 pulses, up to 80 pulses, up to 100 pulses, up to 1,000 pulses or up to 2,000 pulses, including all values and subranges in between.

The packet duration is determined by the cycle count. The higher the cycle count, the longer the packet duration and the larger the quantity of energy delivered. In some embodiments, packet durations are in the range of approximately 50 to 100 microseconds, such as 50 µs, 60 µs, 70 µs, 80 µs, 90 µs or 100 µs. In other embodiments, the packet durations are in the range of approximately 100 to 1000 microseconds, such as 150 µs, 200 µs, 250 µs, 500 µs, or 1000 µs.

The number of packets delivered during treatment, or packet count, may include 1 packet, 2 packets, 3 packets, 4 packets, 5 packets, 10 packets, 15 packets, 20 packets, 50 packets, 100 packets, 1,000 packets, up to 5 packets, up to 10 packets, up to 15 packets, up to 20 packets, up to 100 packets, or up to 1000 packets, including all values and subranges in between. In some embodiments, 5 packets are delivered, wherein each packet has a packet duration of 100 microseconds and a set voltage of 2500 V. In some embodiments, 5 to 10 packets are delivered, wherein each packet has a packet duration of 100 microseconds and a set voltage of 2500 V, which results in a treatment effect that has increased intensity and uniformity. In some embodiments, less than 20 packets, wherein each packet has a packet duration of 100 microseconds and a set voltage of 2500 V, are delivered to avoid affecting the cartilage layer CL. In some embodiments, a total energy-delivery duration between 0.5 to 100 milliseconds at a set voltage of 2500 V can be optimal for the treatment effect.

E. Rest Period

In some embodiments, the time between packets, referred to as the rest period 406, is set between about 0.1 seconds and about 5 seconds, including all values and subranges in between. In other embodiments, the rest period 406 ranges from about 0.001 seconds to about 10 seconds, including all values and subranges in between. In some embodiments, the rest period 406 is approximately 1 second. In particular, in some embodiments the signal is synced with the cardiac rhythm so that each packet is delivered synchronously within a designated period relative to the heartbeats, thus the rest periods coincide with the heartbeats. In other embodiments wherein cardiac synchronization is utilized, the rest period 406 may vary, as the rest period between the packets can be influenced by cardiac synchronization, as will be described in later sections.

F. Switch Time and Dead Time

Figure 3B:
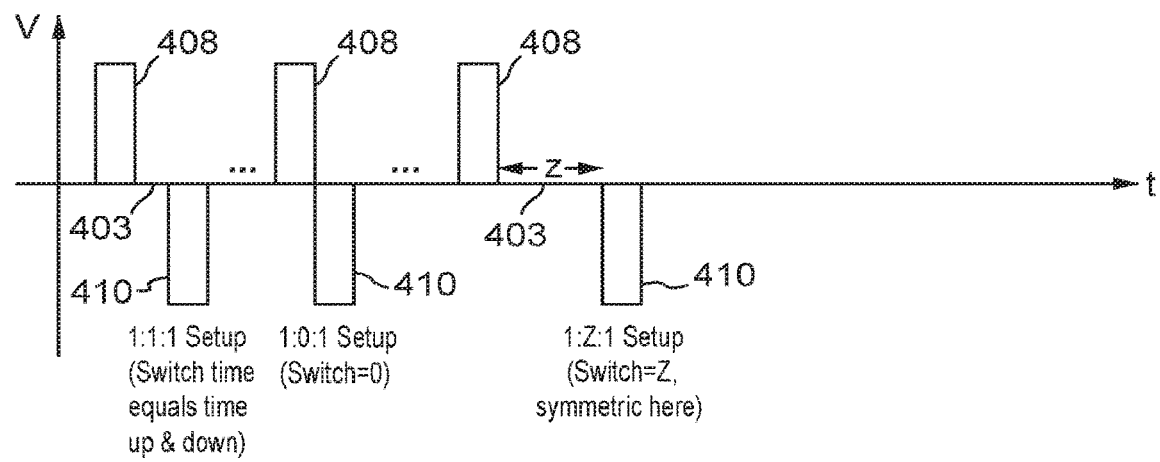
FIG. 3B illustrates various examples of biphasic pulses (comprising a positive peak and a negative peak) having a switch time therebetween.
Figure 3C:
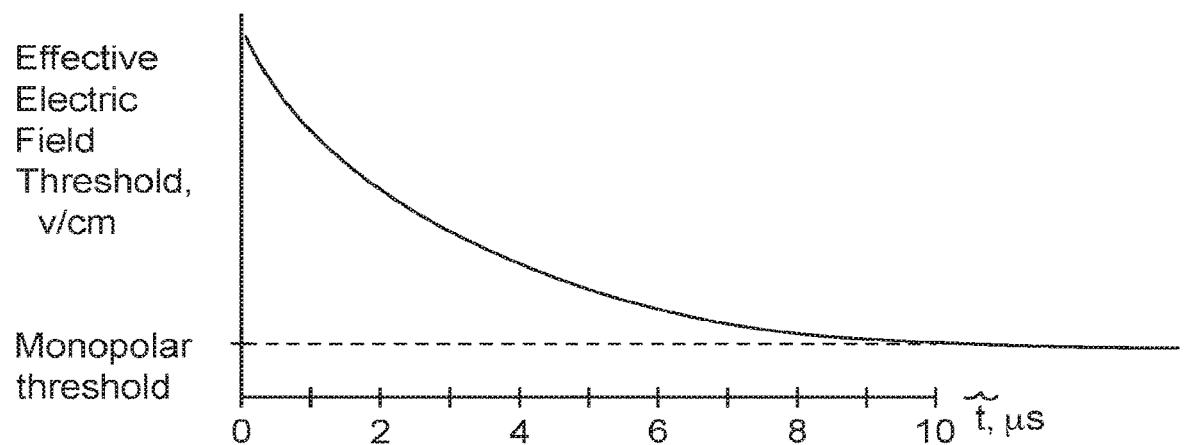
FIG. 3C illustrates the relationship between effective electric field threshold and switch time.

A switch time is a delay or period of no energy that is delivered between the positive and negative peaks of a biphasic pulse, as illustrated in FIGS. 3B-3C. FIG. 3B illustrates various examples of biphasic pulses (comprising a positive peak 408 and a negative peak 410) having a switch time 403 therebetween (however when the switch time 403 is zero, it does not appear). In some embodiments, the switch time ranges between about 0 to about 1 microsecond, including all values and subranges in between. In other embodiments, the switch time ranges between 1 and 20 microseconds, including all values and subranges in between. FIG. 3C illustrates the relationship between effective electric field threshold and switch time.

Delays may also be interjected between each cycle of the biphasic pulses, referred as "dead-time". Dead time occurs within a packet, but between biphasic pulses. This is in contrast to rest periods which occur between packets. In some embodiments, the dead time 412 is set between about 0 and about 500 nanoseconds, including 0 to 20 microseconds, including all values and subranges in between. In other embodiments, the dead time 412 is in a range of approximately 0 to 10 microseconds, or about 0 to about 100 microseconds, or about 0 to about 100 milliseconds, including all values and subranges in between. In some embodiments, the dead time 412 is in the range of 0.2 to 0.3 microseconds. Dead time may also be used to define a period between separate, monophasic, pulses within a packet.

Delays, such as switch times and dead times, are introduced to a packet to reduce the effects of biphasic cancellation within the waveform. Biphasic cancellation or bipolar cancellation is a term used to refer to the reduced induction of cellular modulation in response to biphasic waveforms versus monophasic waveforms, particularly when switch times and dead times are small, such as below 10 µs. One explanation for this phenomenon is provided here, though it may be appreciated that there are likely other biological, physical, or electrical characteristics or alterations that result in the reduced modulation from biphasic waveforms. When cells are exposed to the electromotive force induced by the electric field presence, there is electrokinetic movement of ions and solutes within the intracellular and extracellular fluids. These charges accumulate at dielectric boundaries such as cell and organelle membranes, altering the resting transmembrane potentials (TMPs). When the electric field is removed, the driving force that generated the manipulated TMPs is also eliminated, and the normal biotransport and ionic kinetics operating with concentration gradients begin to restore normative distributions of the solutes. This induces a logarithmic decay of the manipulated TMP on the membranes. However, if rather than eliminating the electric field, the electric field polarity is retained but with a reversed polarity, then there is a new electromotive force actively eliminating the existing TMP that was induced, followed by the accumulation of a TMP in the opposite polarity. This active depletion of the initially manipulated TMP considerably restricts the downstream effects cascade that may occur to the cell, weakening the treatment effect from the initial electric field exposure. Further, where the subsequent electric field with reversed polarity must first "undo" the original TMP manipulation generated, and then begin accumulating its own TMP in the opposite polarity; the final TMP reached by the second phase of the electric field is not as strong as the original TMP, assuming identical durations of each phase of the cycle. This reduces the treatment effects generated from each phase of the waveform resulting in a lower treatment effect than that generated by either pulse in the cycle would achieve alone. This phenomenon is referred as biphasic cancellation. For packets with many cycles, this pattern is repeated over the entire set of cycles and phase changes within the cycles for the packet. This dramatically limits the effect from the treatment. When cell behavior is modulated as a result of the pulsed electric fields by mechanisms other than purely transmembrane potential manipulation, it may be appreciated that the effects of biphasic cancellation are less pronounced, and thus the influence of switch times and dead times on treatment outcome are reduced.

Thus, in some embodiments, the influence of biphasic cancellation is reduced by introducing switch time delays and dead time. In some instances, the switch time and dead time are both increased together to strengthen the effect. In other instances, only switch time or only dead time are increased to induce this effect.

It may be appreciated that typically appropriate timing is for the relaxation of the TMP to complete after 5× the charging time-constant, τ. For most cells, the time constant may be approximated as 1 μs. Thus, in some embodiments the switch time and the dead time are both set to at least 5 μs to eliminate biphasic cancellation. In other embodiments, the reduction in biphasic cancellation may not require complete cell relaxation prior to reversing the polarity, and thus the switch time and the dead time are both set at 0.5 μs to 2 μs In other embodiments, the switch time and the dead time are set to be the same length as the individual pulse lengths, since further increases in these delays may only offer diminishing returns in terms of increased treatment effect and the collateral increase in muscle contraction. In this way, the combination of longer-scale pulse durations (>500 ns) and stacked pulse cycles with substantial switch time and dead time delays, it is possible to use biphasic waveforms without the considerably reduced treatment effect that occurs due to biphasic cancellation. In some cases, the tuning of these parameters may be performed to evoke stronger treatment effects without a comparably proportional increase in muscle contraction. For example, using 600 kHz waveform with switch time=dead time=1.66 us (2× the duration as the pulses), may be used to retain the reduction in muscle contraction versus monophasic pulse waveforms, but with the retention of stronger treatment effects.

In some embodiments, the switch time duration is adjusted such that the degree of therapy effect relative to distant cell effects is optimized for the target of the therapy. In some embodiments, the switch time duration is minimized to decrease distant muscle cell contractions, with lesser local therapy effect. In other embodiments, the switch time duration is extended to increase the local therapy effect, with potential additional distant muscle cell contractions. In some embodiments, the switch time or dead time duration are extended to increase the local therapy effect, and the use of neuromuscular paralytics are employed to control the resulting increase in muscle contraction. In some embodiments, switch time duration is 10 ns to 2 μs while in other embodiments, the switch time duration is 2 μs to 20 μs. In some instances, when cell modulation is targeted in a way where transmembrane potential manipulation is not the primary mechanism needed to evoke the targeted treatment effects, the switch time and dead time delays are minimized to less than 0.1 μs or to 0 μs. This elimination of delays minimizes the peripheral, non-targeted treatment effects such as skeletal muscle contraction or cardiac muscle action potential and contraction but will not alter the treatment effect intensity at the targeted site.

Another benefit of utilizing switch time and the dead time delays to increase treatment effects for biphasic waveforms is a reduction in generator demands, whereby the introduction of pauses will enable stronger treatment effects without requiring asymmetric/unbalanced pulse waveforms. In this case, unbalanced waveforms are described as those that are monophasic, or have an unbalanced duration or voltage or combination in one polarity relative to the other. In some cases, unbalanced means that the integral of the positive portions of the waveform are not equal to the integral of the negative portions of the waveform. Generators capable of delivering unbalanced waveforms have a separate set of design considerations that are accounted for thereby increasing potential generator complexity.

G. Waveforms

Figure 3D:
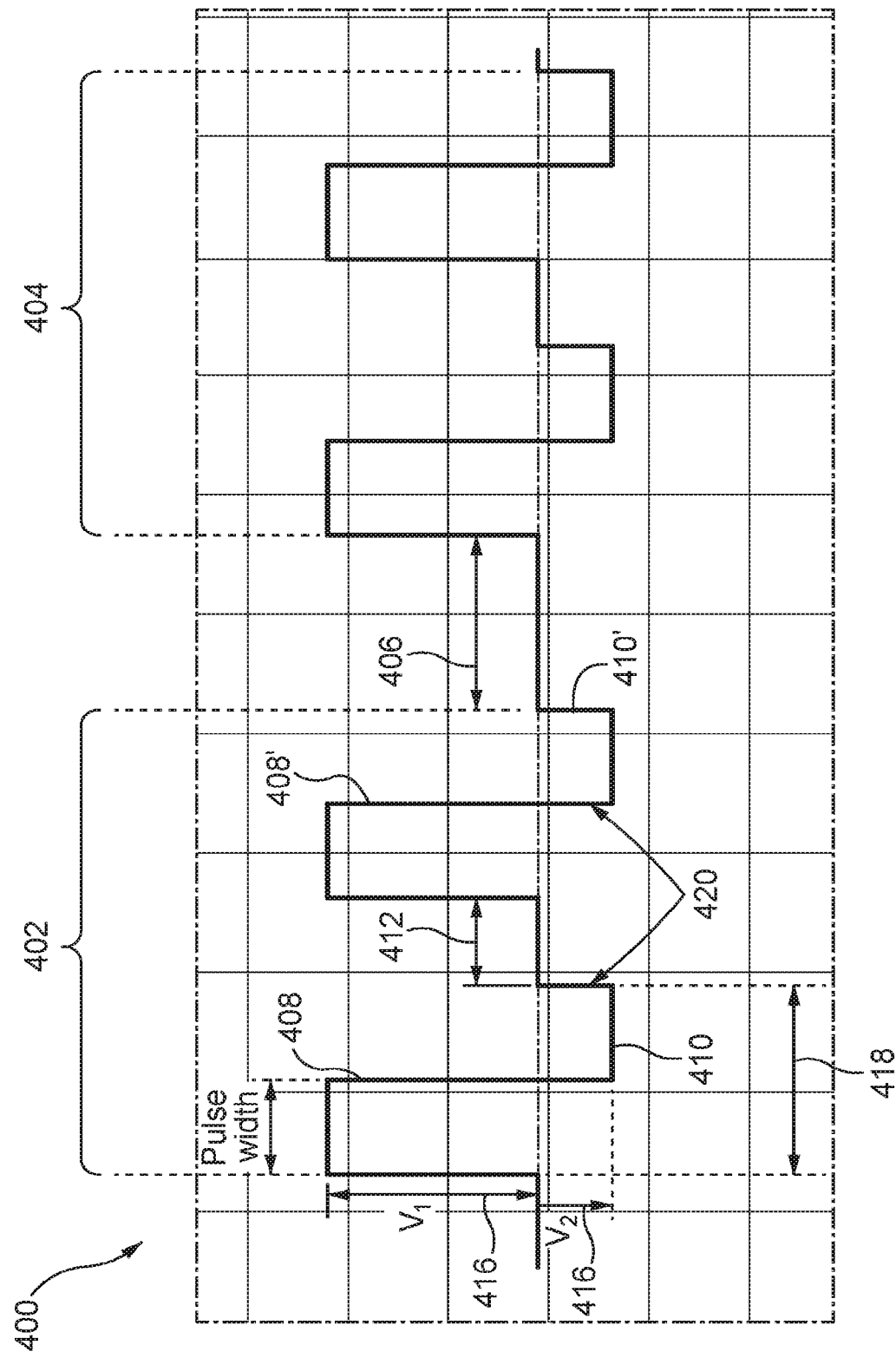
FIG. 3D illustrates an example waveform of another energy delivery algorithm.
Figure 3E:
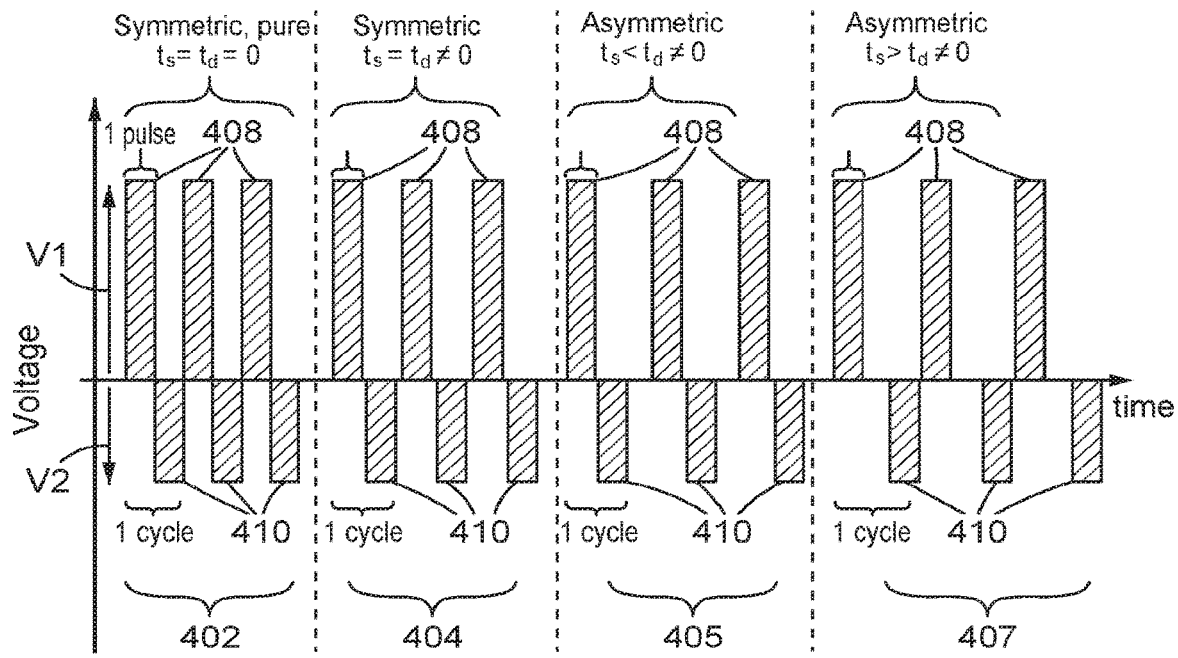
FIGS. 3E-3F illustrates further examples of waveforms having unequal voltages.

FIG. 3A illustrates an embodiment of a waveform 400 having symmetric pulses such that the voltage and duration of pulse in one direction (i.e., positive or negative) is equal to the voltage and duration of pulse in the other direction. FIG. 3D illustrates an example waveform 400 prescribed by another energy delivery algorithm 152 wherein the waveform 400 has voltage imbalance. Here, two packets are shown, a first packet 402 and a second packet 404, wherein the packets 402, 404 are separated by a rest period 406. In this embodiment, each packet 402, 404 is comprised of a first biphasic cycle (comprising a first positive pulse peak 408 having a first voltage V1 and a first negative pulse peak 410 having a second voltage V2) and a second biphasic cycle (comprising a second positive pulse peak 408' having first voltage V1 and a second negative pulse peak 410' having a second voltage V2). Here the first voltage V1 is greater than the second voltage V2. The first and second biphasic cycles are separated by dead time 412 between each pulse. Thus, the voltage in one direction (i.e., positive or negative) is greater than the voltage in the other direction so that the area under the positive portion of the curve does not equal the area under the negative portion of the curve. This unbalanced waveform may result in a more pronounced treatment effect as the dominant positive or negative amplitude leads to a longer duration of same charge cell membrane charge potential. In this embodiment, the first positive peak 408 has a set voltage 416 (V1) that is larger than the set voltage 416' (V2) of the first negative peak 410. FIG. 3E illustrates further examples of waveforms having unequal voltages. Here, four different types of packets are shown in a single diagram for condensed illustration. The first packet 402 is comprised of pulses having unequal voltages but equal pulse widths, along with no switch times and dead times. Thus, the first packet 402 is comprised of four biphasic pulses, each comprising a positive peak 408 having a first voltage V1 and a negative peak 410 having a second voltage V2). Here the first voltage V1 is greater than the second voltage V2. The second packet 404 is comprised of pulses having unequal voltages but symmetric pulse widths (as in the first pulse 402), with switch times equal to dead times. The third packet 405 is comprised of pulses having unequal voltages but symmetric pulse widths (as in the first pulse 402), with switch times that are shorter than dead times. The fourth packet 407 is comprised of pulses having unequal voltages but symmetric pulse widths (as in the first pulse 402), with switch times that are greater than dead times. It may be appreciated that in some embodiments, the positive and negative phases of biphasic waveform are not identical, but are balanced, where the voltage in one direction (i.e., positive or negative), is greater than the voltage in the other direction but the length of the pulse is calculated such that the area under the curve of the positive phase equals the area under the curve of the negative phase.

In some embodiments, imbalance includes pulses having pulse widths of unequal duration. In some embodiments, the biphasic waveform is unbalanced, such that the voltage in one direction is equal to the voltage in the other direction, but the duration of one direction (i.e., positive or negative)

is greater than the duration of the other direction, so that the area under the curve of the positive portion of the waveform does not equal the area under the negative portion of the waveform.

Figure 3F:
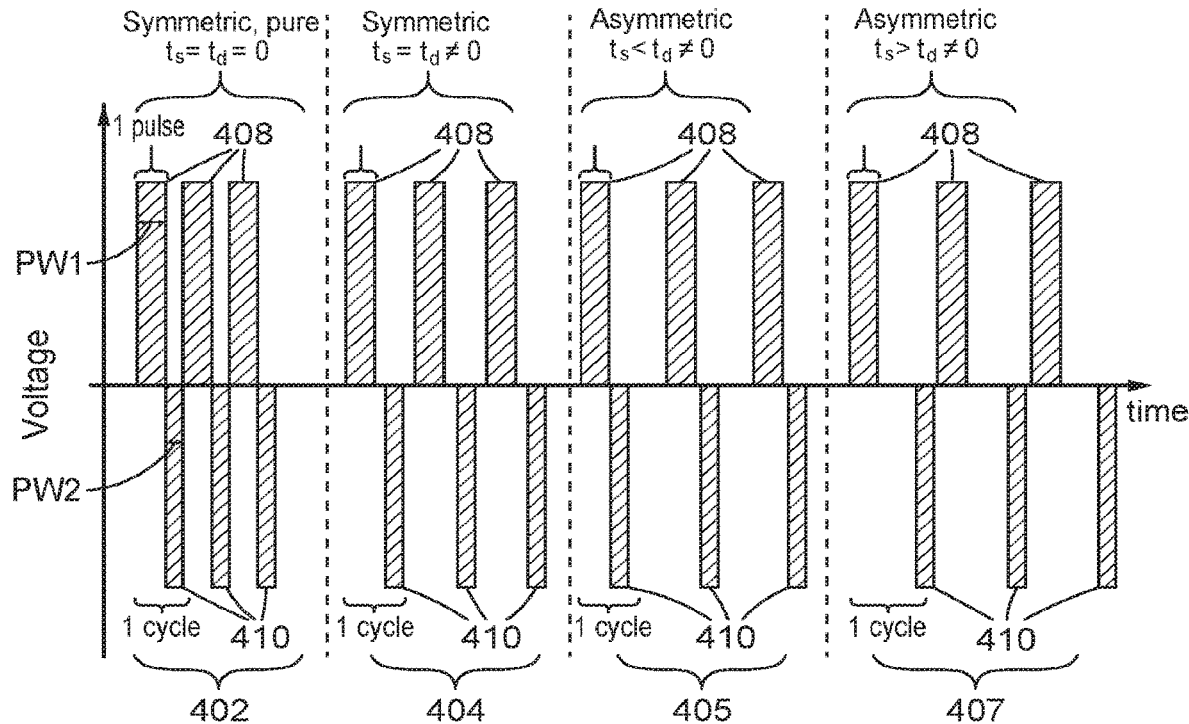

FIG. 3F illustrates further examples of waveforms having unequal pulse widths. Here, four different types of packets are shown in a single diagram for condensed illustration. The first packet 402 is comprised of pulses having equal voltages but unequal pulse widths, along with no switch times and dead times. Thus, the first packet 402 is comprised of four biphasic pulses, each comprising a positive peak 408 having a first pulse width PW1 and a negative peak 410 having a second pulse width PW2). Here the first pulse width PW1 is greater than the second pulse width PW2. The second packet 404 is comprised of pulses having equal voltages but unequal pulse widths (as in the first pulse 402), with switch times equal to dead times. The third packet 405 is comprised of pulses having equal voltages but unequal pulse widths (as in the first pulse 402), with switch times that are shorter than dead times. The fourth packet 407 is comprised of pulses having equal voltages but unequal pulse widths (as in the first pulse 402), with switch times that are greater than dead times.

Figure 3G:
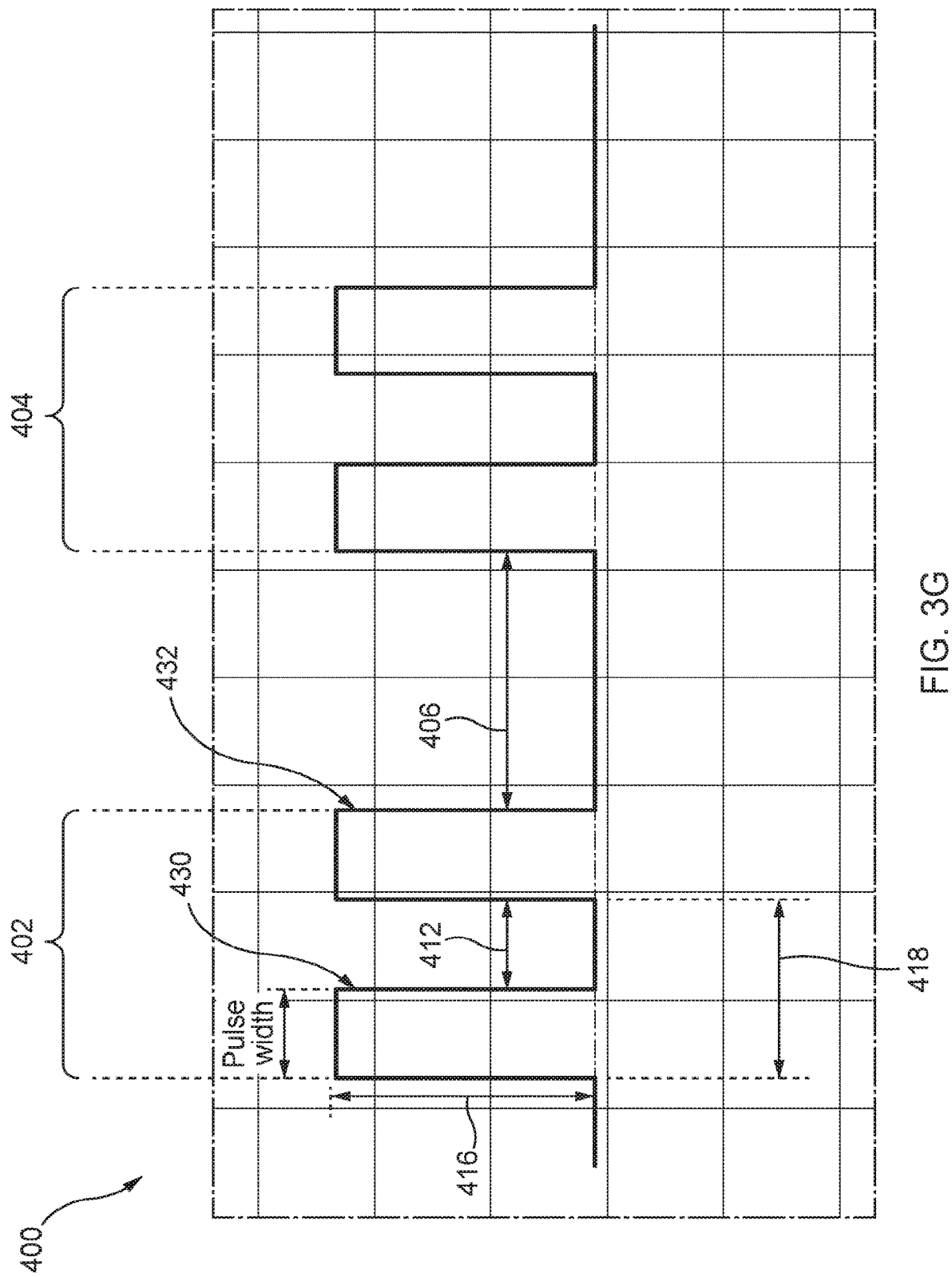
FIG. 3G illustrates an example waveform of another energy delivery algorithm.

FIG. 3G illustrates an example waveform 400 prescribed by another energy delivery algorithm 152 wherein the waveform is monophasic, a special case of imbalance whereby there is only a positive or only a negative portion of the waveform. Here, two packets are shown, a first packet 402 and a second packet 404, wherein the packets 402, 404 are separated by a rest period 406. In this embodiment, each packet 402, 404 is comprised of a first monophasic pulse 430 and a second monophasic pulse 432. The first and second monophasic pulses 430, 432 are separated by dead time 412 between each pulse. This monophasic waveform could lead to a more desirable treatment effect as the same charge cell membrane potential is maintain for longer durations. However, adjacent muscle groups will be more stimulated by the monophasic waveform, compared to a biphasic waveform.

Figure 3H:
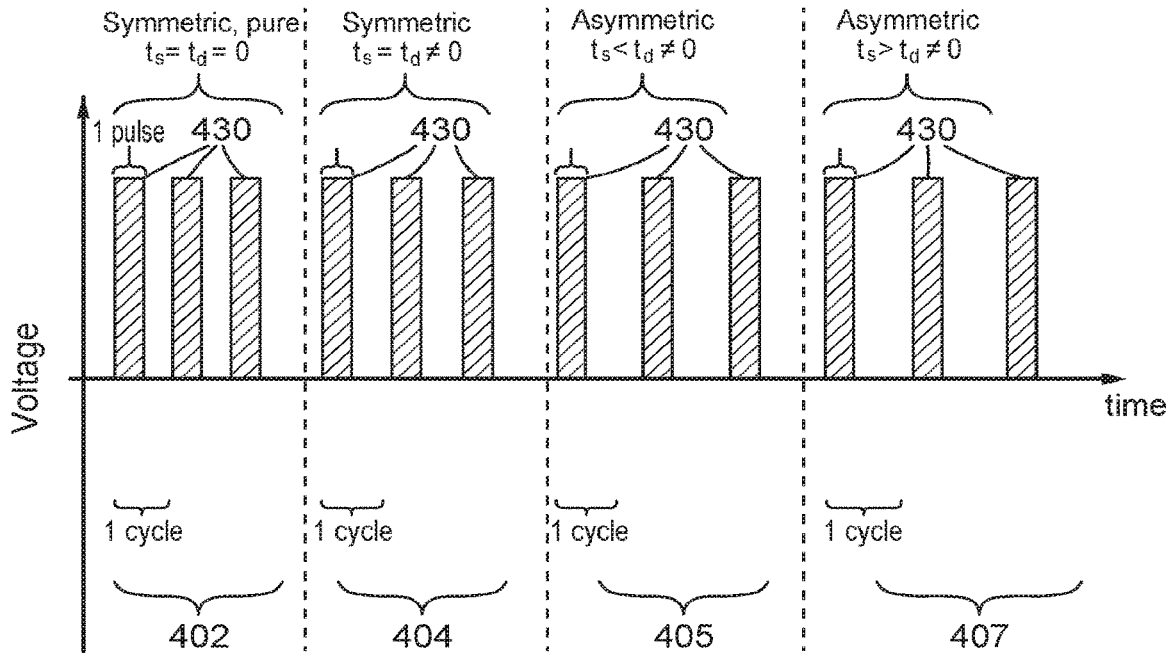
FIG. 3H illustrates further examples of waveforms having monophasic pulses.

FIG. 3H illustrates further examples of waveforms having monophasic pulses. Here, four different types of packets are shown in a single diagram for condensed illustration. The first packet 402 is comprised of pulses having identical voltages and pulse widths, with no switch times (because the pulses are monophasic) and a dead time equal to the active time. In some cases, there may be less dead time duration than the active time of a given pulse. Thus, the first packet 402 is comprised of three monophasic pulses 430, each comprising a positive peak. In instances where the dead time is equal to the active time, the waveform may be considered unbalanced with a fundamental frequency representing a cycle period of 2× the active time and no dead time. The second packet 404 is comprised of monophasic pulses 430 having equal voltages and pulse widths (as in the first packet 402), with larger dead times. The third packet 405 is comprised of monophasic pulses 430 having equal voltages and pulse widths (as in the first packet 402), and even larger dead times. The fourth packet 407 is comprised of monophasic pulses 430 having equal voltages and pulse widths (as in the first packet 402), with yet larger dead times.

Figure 3I:
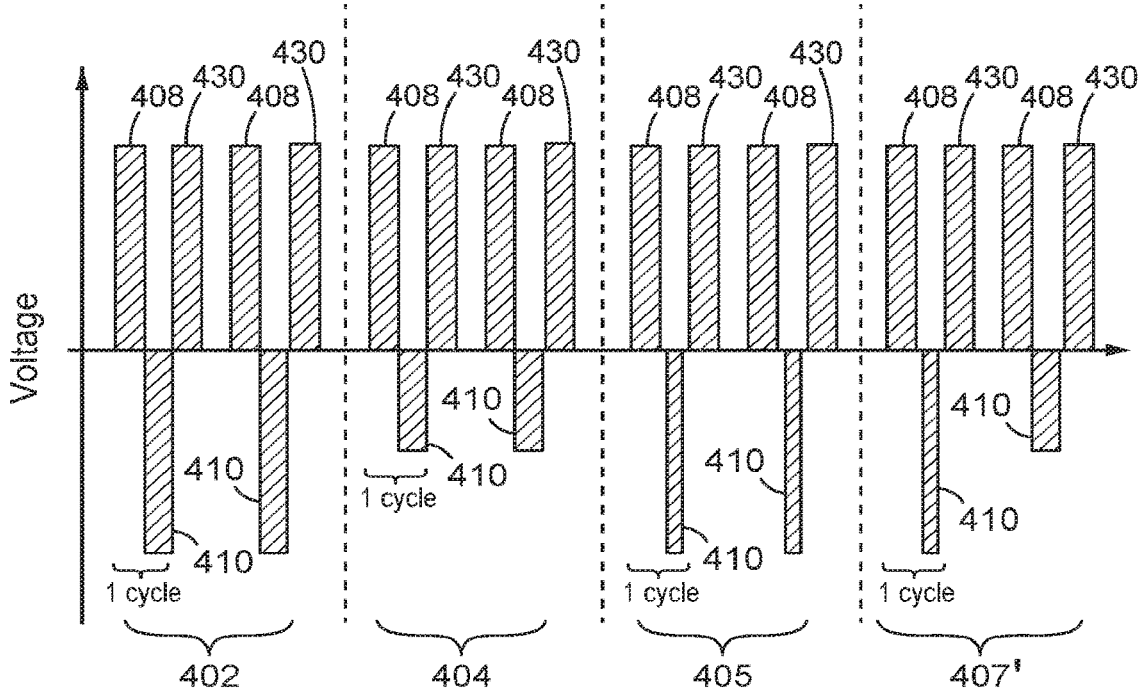
FIG. 3I illustrates examples of waveforms having phase imbalances achieved by delivering more than one pulse in one polarity before reversing to an unequal number of pulses in the opposite polarity.

In some embodiments, an unbalanced waveform is achieved by delivering more than one pulse in one polarity before reversing to an unequal number of pulses in the opposite polarity. FIG. 3I illustrates further examples of waveforms having such phase imbalances. Here, four different types of packets are shown in a single diagram for condensed illustration. The first packet 402 is comprised of four cycles having equal voltages and pulse widths, however, opposite polarity pulses are intermixed with monophasic pulses. Thus, the first cycle comprises a positive peak 408 and a negative peak 410. The second cycle is monophasic, comprising a single positive pulse with no subsequent negative pulse 430. This then repeats. The second packet 404 is comprised of intermixed biphasic and monophasic cycles (as in the first packet 402), however the pulses have unequal voltages. The third packet 405 is comprised of intermixed biphasic and monophasic cycles (as in the first packet 402), however the pulses have unequal pulse widths. The fourth packet 407 is comprised of intermixed biphasic and monophasic pulses (as in the first packet 402), however the pulses have unequal voltages and unequal pulse widths. Thus, multiple combinations and permutations are possible.

It should be noted that in each positive or negative phase of the biphasic cycle, portions of the airway wall W cells facing opposite sides of the energy will experience the opposite effects. In some embodiments, the hyperpolarized portion faces the dispersive or return electrode 140. It may further be appreciated that cells have a native negative resting electric transmembrane potential (TMP). Thus, changes to the native TMP on the side of the cell that promote a negative TMP will have an exaggerated absolute TMP. Conversely, the side of the cells that induce a positive TMP will have a lower reached absolute TMP induced. In either case, invocation of the desired therapeutic result may be reached by disturbing the native cell TMP, altering the cell behavior regardless of the final absolute TMP. Further, this difference may vary when considering the TMPs induced on the intracellular organelles.

Regarding the utility of unequal waveforms, the unbalanced TMP manipulation achieved reduces the implications of biphasic cancellation. There is a correlative relationship between the degree of imbalance, approaching a monopolar waveform as fully unbalanced, and the intensity of TMP manipulation. This will result in proportional relationship between the extent of treatment effect as well as the degree of muscle contraction. Thus, approaching more unbalanced waveforms will enable stronger treatment effects at the same voltage and frequency (if applicable) for biphasic waveforms than those produced from purely balanced biphasic waveforms. For example, the treatment effect evoked by a 830 ns-415 ns-830 ns-etc pulse length sequence within a packet will have the pulse constituting the second half of the cycle being half the duration of the original phase. This will restrict the induction of TMP manipulation by the second phase of the cycle, but will also generate less reversed TMP, enabling a stronger effect from the original polarity in the subsequent cycle at the original length. In another example, the "positive" portion of the waveform may be 2500V, with the "negative" portion being 1500V (2500-1250-2500-etc V), which will induce comparable effects on TMP polarization as that which was described for the pulse duration imbalance. In both of these cases, the manipulation of the opposing polarity intensity will result in cumulative stronger TMP manipulation for the positive pulse in the cycle. This will thus reduce the effects of biphasic cancellation and will generate stronger treatment effects than a protocol of 830-830-830 ns or 2500-2500-2500V, despite the deposition of less total energy delivered to the tissue. In this way, it is possible to deliver less total energy to the tissue but evoke the desired treatment effect when TMP manipulations are integral to the treatment mechanism of action.

Extended further, the fully unbalanced waveforms would not include any opposite polarity component but may still include brief portions of pulses delivered in just the positive phase. An example of this is a packet that contains 830 ns of positive polarity, an 830 ns pause with no energy delivered, followed by another 830 ns of positive polarity, and so forth. The same approach is true whether considering the pulse length imbalance or the voltage imbalance, as the absence of a negative pulse is equivalent to setting either of these parameters to zero for the "negative" portion.

However, appropriate treatment delivery considers that the advantages offered by biphasic waveforms, namely the reduction of muscle contraction, resulting from biphasic cancellation will likewise be reduced. Therefore, the appropriate treatment effect extent is balanced against the degree of acceptable muscle contraction. For example, an ideal voltage imbalance may be 2500-1000-2500- . . . V, or 2500-2000-2500- . . . V; or 830-100-830- . . . ns, or 830-500-830- . . . ns.

H. Waveform Shapes

Figure 3J:
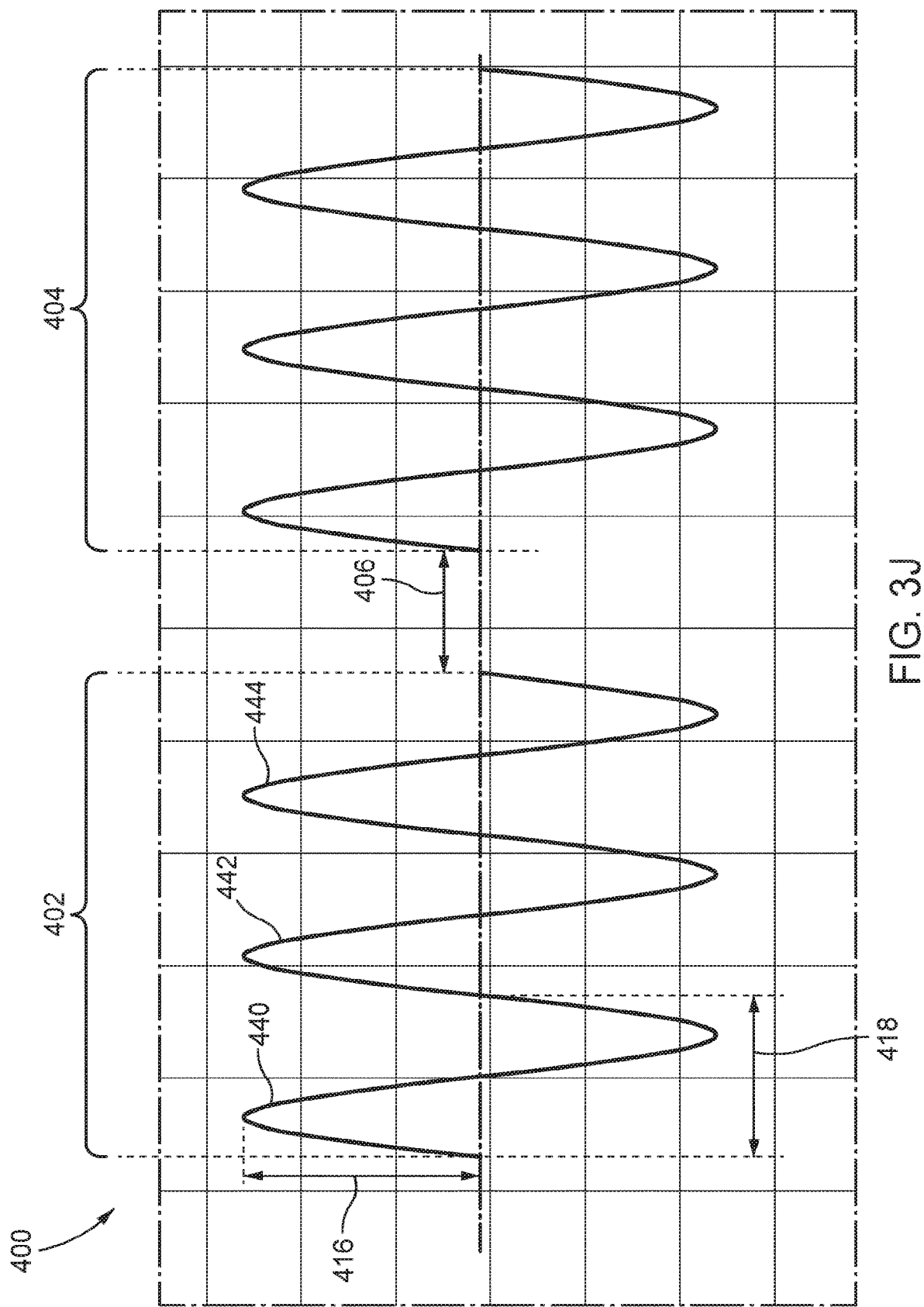
FIG. 3J illustrates an example waveform of another energy delivery algorithm.

FIG. 3J illustrates an example waveform 400 prescribed by another energy delivery algorithm 152 wherein the pulses are sinusoidal in shape rather than square. Again, two packets are shown, a first packet 402 and a second packet 404, wherein the packets 402, 404 are separated by a rest period 406. In this embodiment, each packet 402, 404 is comprised three biphasic pulses 440, 442, 444. And, rather than square waves, these pulses 440, 442, 444 are sinusoidal in shape. One benefit of a sinusoidal shape is that it is balanced or symmetrical, whereby each phase is equal in shape. Balancing may assist in reducing undesired muscle stimulation.

Energy delivery may be actuated by a variety of mechanisms, such as with the use of a button 164 on the catheter 102 or a foot switch 168 operatively connected to the generator 104. Such actuation typically provides a single energy dose. The energy dose is defined by the number of packets delivered and the voltage of the packets. Each energy dose delivered to the airway wall W maintains the temperature at or in the wall W below a threshold for thermal ablation, particularly thermal ablation of the basement membrane BM which comprises denaturing stromal proteins in the basement membrane or deeper submucosal extracellular protein matrices. In addition, the doses may be titrated or moderated over time so as to further reduce or eliminate thermal build up during the treatment procedure. Instead of inducing thermal damage, defined as protein coagulation, the energy dose provide energy at a level which induces biological mechanisms and cellular effects which ultimately lead to the regeneration of healthy tissue.

III. Vascular Applications

In some embodiments, the tissue modification systems of FIGS. 1-2 are adapted for use in the treatment of blood vessels and other cardiac tissue, particularly for the treatment of atrial fibrillation. In some embodiments, the tissue modification system utilizes energy delivery algorithms configured specifically for cardiac applications, more particularly for affecting tissue in a manner to successfully treat atrial fibrillation. Potential cardiac targets for treatment include the regions implicated in generating or conducting aberrant electrical signals. These signals may induce the uncoordinated activation of cardiac myocytes, especially in the atrial regions upstream of the atrioventricular node. Poor operation of the atria reduces their functionality and may result in increased risk for patient angina, stroke, or other cardiac events. In some embodiments, regions within the pulmonary veins (PVs), particularly the myocardial sleeves of the PVs, are targeted due to the presence of automaticity in cells within the myocardial tissue of the PVs. In some embodiments, the therapeutic energy delivery catheter 102 of FIG. 2 is utilized for treating the PVs. In other embodiments, a modified version of the therapeutic energy delivery catheter 102 of FIG. 2 is utilized for treating the PVs. For example, in some embodiments, the catheter 102 is modified such that its distal end is curved to approximate an angle of an introducer sheath angle utilized to access PVs. In some embodiments, the catheter 102 is modified to have a shorter contact length, such as by reducing the length of the electrode body 108. Likewise, in some embodiments, the catheter 102 is modified for femoral access. Typically, femoral access to the PVs involves accessing a femoral vein and advancing the energy body 108 of the catheter 102 into the right atrium via the inferior vena cava and then into the left atrium via a trans-septal puncture. This longer pathway is accommodated by modifications to the catheter 102 of FIG. 2 including an increased length of the elongate shaft 206, such as 100 cm or 150 cm, to ensure fit through the trans-septal introducer sheath. Additional modifications include assisted deployment of the energy delivery body 108, such as with the use of an internal expansion member (e.g. balloon) to improve the expansion characteristics and likelihood of attaining circumferential treatment contact within the PV. Such delivery is typically achieved with the use of ultrasound and angiography to guide physical placement of the energy delivery body 108.

Furthermore, in some embodiments, the catheter 102 and energy delivery algorithms are customized to particularly treat cardiac tissues, as opposed to other luminal targets. For example, in some embodiments such customization is particularly aimed at treating atrial fibrillation and includes killing superficial cardiomyocytes that cause aberrant rhythms, or generating a transmural fibrotic tissue restructuring to provide an adequate electrical conduction block. When generating transmural effects, the electrodes of the energy delivery body 108 has sufficiently low and focused contact area so as to appropriately concentrate the energy to attain a very concentrated treatment effect that sufficiently penetrates the full thickness of the targeted site, either in the pulmonary veins, their ostia, or the atria. Alternately, the electric voltage delivered is increased relative to other, more superficial, luminal targets, thus increasing the strength of the delivered energy generally while retaining the original electrode contact area. In addition, in some embodiments, secondary pulse parameters are further modified to decrease the lethal electric field threshold of the targeted cell layers (such as by decreasing the biphasic pulsed field frequency, thus increasing the individual pulse length), increasing the number of pulse cycles within a given packet (which increases the total packet duration), or increasing the number of delivered packets. In addition, in some embodiments, the use of asymmetrical (length or voltage) waveforms or monophasic waveforms are employed to significantly strengthen the treatment effect, though the degree of asymmetry or monophasic pulses are balanced to ensure the extent of muscle contraction for the patient remains within acceptable ranges. If necessary, it is also possible to employ the use of a muscle paralytic to further reduce muscle contractions, enabling stronger pulse protocols or asymmetric biphasic or monophasic waveforms.

As mentioned, in some embodiments, the energy delivery body 108 comprises a single monopolar delivery electrode wherein the energy delivery body 108 is comprised of a plurality of wires or ribbons 120 forming a spiral-shaped basket serving as the electrode. The energy delivery body 108 is positioned within a PV and pulsed electric fields are delivered via the energy delivery body 108 to the PV so as to induce cell death of the cardiomyocyte and other nominal cell types in the region, which become replaced with fibrous tissue deposition as part of the tissue healing process. This fibrous tissue is a poor conduit for electrical conduction, and thus a circumferential, transmural induction of this tissue typically serves as an adequate electrical conduction block, preventing aberrant currents generated in the PV antra from propagating through the atrium. By stopping the aberrant currents, the atrial cardiac muscle cells are able to better coordinate their activation, eliminating fibrillation.

It will be appreciated that cardiac applications involve blood-filled fields. Numerical simulations in the vasculature indicate that the blood is a conductive medium and somewhat acts as a virtual electrode, dissipating the electrical energy longitudinally along the vessel, and decreasing the focal electric field intensity at the point of electrode contact. This can reduce the treatment effect depth for cardiac targets in comparison to lung passageways, which are filled with non-conductive air. In some embodiments, the catheter 102 is adapted to electrically insulate the portions of the electrode body 108 so as to reduce electric current leakage to the blood. In some embodiments, this involves insulating the proximal and distal portions of the electrode body 108 which have the most contact with blood flowing through the blood vessel. In some embodiments, this significantly reduces electric current leakage to the blood. Likewise, in some embodiments, the energy delivery algorithms of the present disclosure are configured to provide improved energy delivery under such conditions (i.e. in the presence of conductive medium). In some embodiments, such algorithms employ even greater pulse intensities, which are achieved similarly achieving deeper transmural thickness effects, such as increasing the voltage, decreasing the frequency, increasing the number of cycles per packet, or increasing the total number of packets delivered per activation site. However, another approach to overcome the electric current leakage effects is to electrically isolate the contact region of the circumferential electrode body 108 to prevent conduction into the blood which will significantly increase the concentration of energy delivery into the targeted tissue itself, inducing stronger treatment effects.

During ideal conditions, energy delivered to the body lumen walls by the energy delivery body 108 is perfectly balanced throughout the circumference of the lumen. However, in some situations the electrical characteristics of the tissue and/or environment induce preferential current flow through particular areas during monopolar delivery. Thus, there is often a natural distortion of the electric field toward these particular areas. This causes an increase in treatment affect in these areas and a reduction in treatment affect in the non-preferred areas. Such irregularity may be inconsequential in some situations, however in other situations such irregularity may impact treatment outcome. Thus, increased regularity would provide a more predictable treatment and may improve patient outcomes while reducing procedure time and energy expenditure. Embodiments of specialized catheter designs, distinct energy delivery algorithms and methods of use of the present disclosure provide such increased regularity. Such improvement may be useful in treating a variety of body lumens, including but not limited to vascular applications. Such improvements may be particularly useful when treating body lumens such as blood vessels and gastrointestinal lumens and may be useful in treating lung passageways.

When treating blood vessels, environmental conditions, the natural tissue structure of the blood vessel wall, and the particulars of the treatment protocol can create different circumstances under which adequate energy delivery is achieved. In addition to a regularity of the treatment effect throughout the circumference of the lumen, an increased depth of penetration may also be desired. For example, when treating airways, a relatively shallow depth penetration may be sufficient for adequate energy delivery in the treatment of a disease state. However, when treating blood vessels, a deeper depth penetration may be desired for adequate energy delivery and tissue effect, particularly when treating a condition such as atrial fibrillation.

Some known catheter and surgical ablation approaches in the treatment of atrial fibrillation isolate the PVs electrically from the left atrial (LA) wall. Complete electrical disconnection of the PVs from the left atrium is an electrophysiological end point responsible for achieving reliable control of the arrhythmia. Although electrical disconnection is often achieved by the end of conventional procedures, long-term efficacy of catheter ablation remains modest. Most patients will require 1-2 procedures to achieve reasonable efficacy. The chief reason for repeated procedures is recovered PV-to-LA conduction.

Some known studies have shown the time-dependent inevitability of PV conduction recovery and its relationship to future atrial fibrillation recurrence. Up to 50%-64% of PVs reconnect during an intraprocedural waiting period of up to 60 minutes after initially isolating the PVs. Studies in which patients with AF recurrence were studied on second or subsequent procedures have shown that AF recurrence post-catheter ablation is usually associated with resumption of PV-LA conduction.

Putative reasons for resumption of PV-LA conduction are gaps within the ablation line and/or failure to produce transmural lesions. Gaps in lines allow resumption of PV-to-LA electrical activity allowing PV triggers to reinitiate atrial fibrillation and may also serve as triggers for other macroreentrant atrial arrhythmias. Likewise, reversible atrial injury may stem from incomplete lesion formation that results in temporary electrical uncoupling but not cell death. Permanent conduction block across linear lesions requires and/or uses transmural lesions involving cell death. As mentioned previously, the specialized catheter designs, distinct energy delivery algorithms, and methods of use of the present disclosure provide increased circumferential regularity of ablation. This reduces conduction gaps within the ablation line. Additionally, specialized catheter designs, distinct energy delivery algorithms, and methods of use of the present disclosure can increase the capability of forming transmural lesions. Such improvements can be beneficial in treating atrial fibrillation and may be useful in treating a variety of other conditions and/or other body lumens, include lung passageways, gastrointestinal passageways and other natural and artificial passageways in the body.

IV. Focal Therapy

The above described algorithms provide energy to the body lumen or passageway in the form of pulsed electric fields (PEFs). Particular catheter designs and methods have been developed to deliver the PEFs in a manner which provides focal therapy. In some embodiments, PEFs are delivered through independent electrically active electrodes of an energy delivery body, typically in a monopolar fashion. Such delivery concentrates the electrical energy over a smaller surface area, resulting in stronger effects than delivery through an electrode extending circumferentially around the lumen or passageway. It also forces the electrical energy to be delivered in a staged regional approach, mitigating the effect of preferential current pathways through the surrounding tissue. These preferential current pathways are regions with electrical characteristics that induce locally increased electric current flow therethrough rather than through adjacent regions. Such pathways typically result in an irregular electric current distribution around the circumference of a targeted lumen, which thus distorts the electric field and causes an irregular increase in treatment effect for some regions and a lower treatment effect in other regions. This may be mitigated or avoided with the use of focal therapy which stabilizes the treatment effect around the circumference of the targeted region. Thus, by "breaking-up" the PEFs to certain regions at a time, the electrically energy is "forced" across different regions of the circumference, ensuring an improved degree of treatment circumferential regularity.

Figure 4:
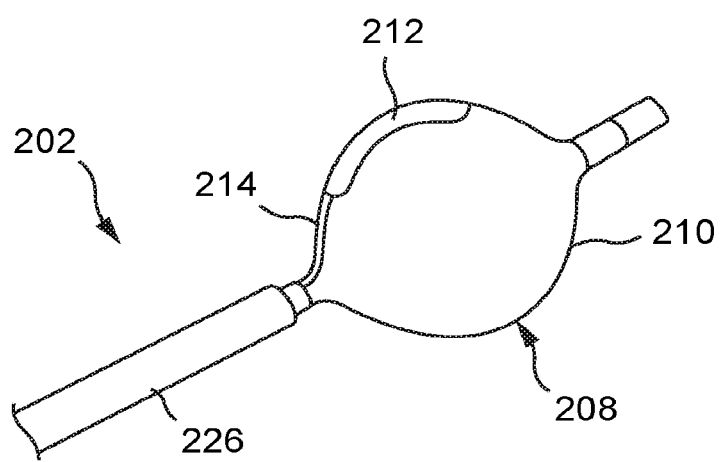
FIG. 4 illustrates an embodiment of a therapeutic energy delivery catheter comprising an elongate shaft having at least one energy delivery body near its distal end.

FIG. 4 illustrates an embodiment of a therapeutic energy delivery catheter 202 of the present disclosure configured to provide focal therapy. In this embodiment, the catheter 202 has an elongate shaft 206 with at least one energy delivery body 208 near its distal end. The catheter 202 includes a handle 211 (not shown) at its proximal end, such as a handle similar to handle 110 in FIG. 2. The catheter 202 is connectable to a generator, such as generator 104 of FIG. 1, which provides electrical energy to the energy delivery body 208, among other features. In this embodiment, the energy delivery body 208 comprises an expandable member 210, such as an inflatable balloon, having an electrode 212 mounted thereon or incorporated therein. The energy delivery body 208 is delivered to a targeted area in a collapsed configuration. This collapsed configuration can be achieved, for example, by placing a sheath 226 over the energy delivery body 208, which maintains the collapsed configuration allowing smooth delivery. When deployment is desired, the sheath 226 is retracted or the catheter 202 advanced to allow the energy delivery body 208 to expand.

In this embodiment, the electrode 212 has the form of a pad having a relatively broad surface area and thin cross-section. The pad shape provides a broader surface area than other shapes, such as a wire shape. The electrode 212 is connected with a conduction wire 214 which electrically connects the electrode 212 with the generator. In this embodiment, the electrode body 208 has a single electrode 212, however it will be appreciated that the energy delivery body 208 can instead include multiple electrodes 212, such as two, three, four, five, six, seven, eight, nine, ten or more, as will be described in more detail in later sections. The electrodes 212 may be comprised of flexible circuit pads or other materials attached to the expandable member 210 or formed into the expandable member 210. The electrodes 212 may be distributed radially around the circumference of the expandable member 210 and/or they may be distributed longitudinally along the length of the expandable member 210. Such designs may facilitate improved deployment and retraction qualities, easing user operation and compatibility with standard introducer lumens.

In use, the catheter 202 is advanced into a body passageway or lumen L, such as over a guidewire, to a target segment along the length of the lumen L. The target segment has a length and typically extends circumferentially around the inner surfaces of the walls W of the body lumen L, thus forming a ring. In some embodiments, it is desired to deliver energy to the circumferential ring in a series of steps, such as illustrated in FIGS. 4A-4D with corresponding treatment area outcomes illustrated in FIGS. 5A-5D. FIG. 4A illustrates a first step wherein the energy delivery body 208 is expanded within the target segment of the body lumen L so that the electrode 212 is positioned adjacent to, against or pressed against a first portion of the wall W of the lumen L. Energy is then delivered to the first portion of the wall W from the electrically connected generator creating a first treatment area A1. FIG. 5A provides a cross-sectional illustration of the body lumen L at the target segment showing the first treatment area A1 along the top quarter of the circumferential lumen wall. The energy delivery body 208 is then at least partially deflated or retracted and the catheter 202 is rotated, for example 90 degrees in a clockwise direction, as illustrated in FIG. 4B. The energy delivery body 208 is then expanded and electrode 212 is positioned adjacent to, against, or pressed against a second portion of the wall W of the lumen L. Energy is delivered to the second portion of the wall from the electrically connected generator, creating a second treatment area A2. FIG. 5B provides a cross-sectional illustration of the body lumen L at the target segment, showing the second treatment area A2 along the right side quarter of the circumferential lumen wall W. The catheter 202 is then rotated again, for example an additional 90 degrees in the clockwise direction, as illustrated in FIG. 4C. The electrode 212 is positioned adjacent to, against or pressed against a third portion of the wall of the lumen L. Energy is delivered to the third portion of the wall from the electrically connected generator, creating a third treatment area A3. FIG. 5C provides a cross-sectional illustration of the body lumen L at the target segment showing the third treatment area A3 along the bottom quarter of the circumferential lumen wall W. The catheter 202 is then rotated again, for example an additional 90 degrees in the clockwise direction, as illustrated in FIG. 4D. The electrode 212 is positioned adjacent to, against, or pressed against a fourth portion of the wall of the lumen L. Energy is delivered to the fourth portion of the wall from the electrically connected generator, creating a fourth treatment area A4. FIG. 5D provides a cross-sectional illustration of the body lumen L at the target segment, showing the fourth treatment area A4 along the left side quarter of the circumferential lumen wall W. In this manner, the treatment areas A1, A2, A3, A4 collectively cover the circumferential ring around the inner surfaces of the walls W of the body lumen L, thus forming a continuous treatment area without gaps.

It will be appreciated that, in some embodiments, the catheter 202 includes one or more markings along its shaft 206, such as one or more markings around the circumference of the shaft 206, to assist the user in orienting the catheter 202 throughout rotations. In some embodiments, the one or more markings comprise a plurality of markings spaced apart by a uniform distance, with each marking indicating a number of degrees of rotation. For example, each marking can indicate a rotational distance of 15 degrees. In some embodiments, particular markings indicate known rotational distances, such as larger markings indicating 90-degree rotations and smaller markings indicating 45-degree rotations. In some embodiments, particular markings indicate known orientations, such as "top," and/or particular markings indicate alignment with electrodes 212. It will be appreciated that, in some embodiments, the markers are disposed along the handle 211 and/or sheath 226. Thus, the user is able to either rotate both the delivery device (such as a bronchoscope or catheter) and catheter 202, or just rotate the catheter 202 independently.

Figure 6:
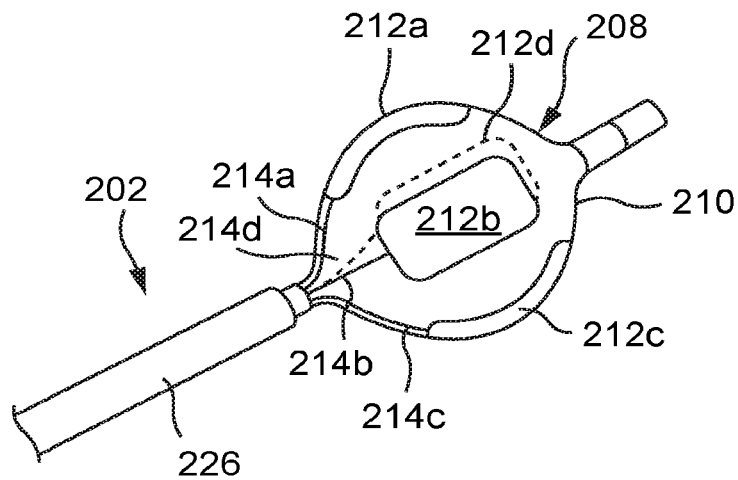
FIG. 6 illustrates an embodiment of an electrode body having four electrodes configured to facilitate circumferential energy delivery to a body lumen without rotation of the catheter.

Alternative electrode body 208 designs allow circumferential energy delivery to a body lumen L without rotation of the catheter 202. An embodiment of such an electrode body 208 is illustrated in FIG. 6.

Figure 7:
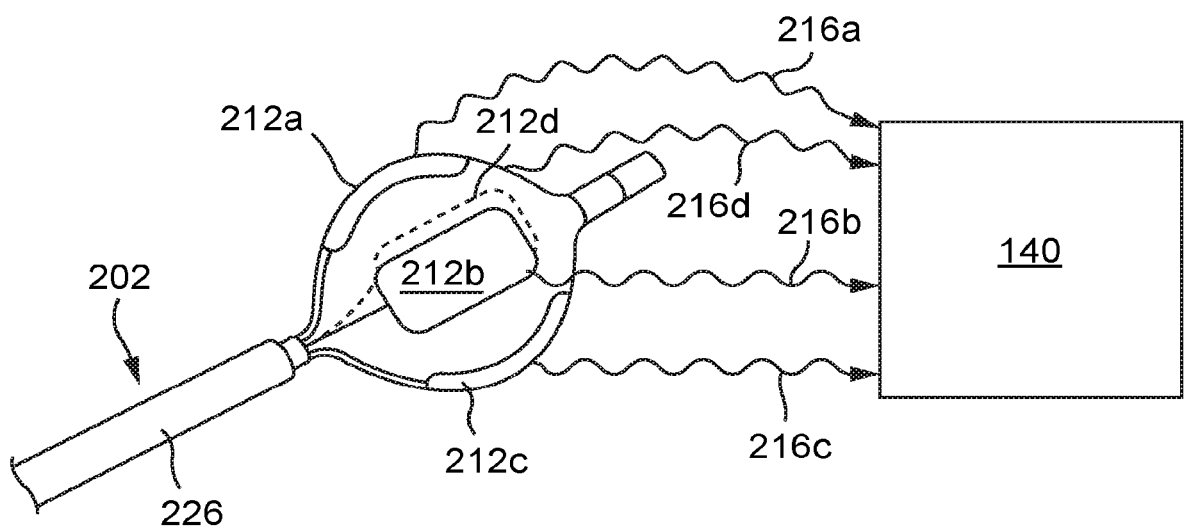
FIG. 7 is an example illustration of the electrode body of FIG. 6, when used in a monopolar configuration.

Here, the electrode body 208 includes four electrodes: a first electrode 212a, a second electrode 212b, a third electrode 212c and a fourth electrode 212d. Here, the electrodes 212a, 212b, 212c, 212d are disposed around the expandable member 210, equally spaced from each other. Each of the electrodes 212a, 212b, 212c, 212d has a corresponding conduction wire 214a 214b, 214c, 214d which provides energy from the generator 104. In this embodiment, the electrodes 212a, 212b, 212c, 212d are independently energized via their conduction wires 214a 214b, 214c, 214d. When used in a monopolar configuration, as illustrated in FIG. 7, each electrode 212a, 212b, 212c, 212d forms an electrical pathway to the dispersive (return) electrode 140. As shown in FIG. 7, the first electrode 212a forms a first electrical pathway 216a, the second electrode 212b forms a second electrical pathway 216b, the third electrode 212c forms a third electrical pathway 216c, and the fourth electrode 212d forms a fourth electrical pathway 216d. When, for example, the first electrode 212a is energized and the other electrodes 212b, 212c, 212d are not energized, all of the energy flows along the first electrical pathway 216a to the dispersive electrode 140. This provides a predictable pathway in which any naturally occurring preference in current flow is overcome by the induced current flow through electrical pathway 216a. This increases treatment effect in the tissue area of the lumen wall through which the first electrical pathway 216a flows.

Figure 8A:
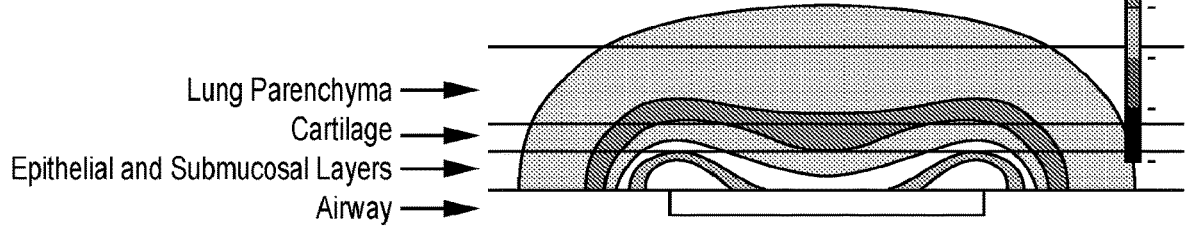
FIG. 8A illustrates an example electric field distribution through various tissue layers of an airway wall when energy is delivered circumferentially, such as with the energy delivery body of FIG. 2.
Figure 8B:
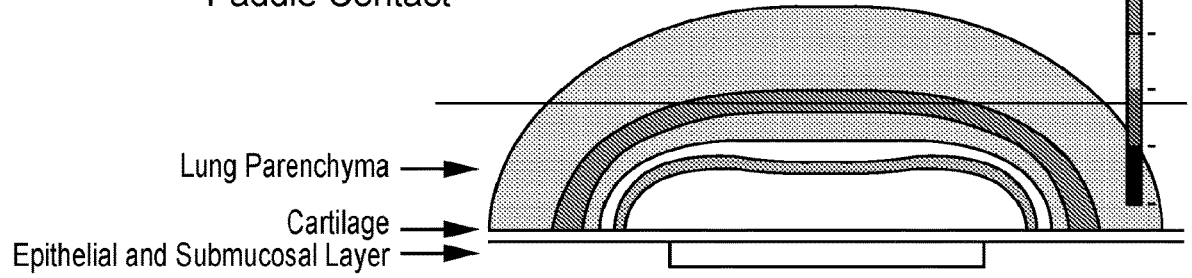
FIG. 8B illustrates an example electric field distribution through various tissue layers of an airway wall under focal delivery, wherein an electrode such as the first electrode of FIG. 6 is energized by itself.

Such an increase in treatment effect includes increased regularity and depth of penetration. FIGS. 8A-8B illustrate such an increased depth of penetration. FIG. 8A illustrates an example electric field distribution through the various tissue layers of an airway wall when energy is delivered circumferentially, such as with an energy delivery body 108 (see, e.g., FIG. 2) having a basket-type electrode in a monopolar configuration. As shown in FIG. 8A, the tissue layers receive varying levels of electric field along the electrode. In contrast, FIG. 8B illustrates an example electric field distribution through the various tissue layers of an airway wall under focal delivery, wherein an electrode pad such as the first electrode 212a is energized by itself. As can be observed in FIG. 8B, the tissue layers receive a much more consistent level of energy along the length of the electrode and the drop off in intensity of the electric field occurs at deeper levels. This allows for better transmural effect without increasing the overall voltage or current delivered. In addition, this reduces the likelihood of collateral effects, such as muscle contraction, pain or thermal damage to the area.

Figure 9:
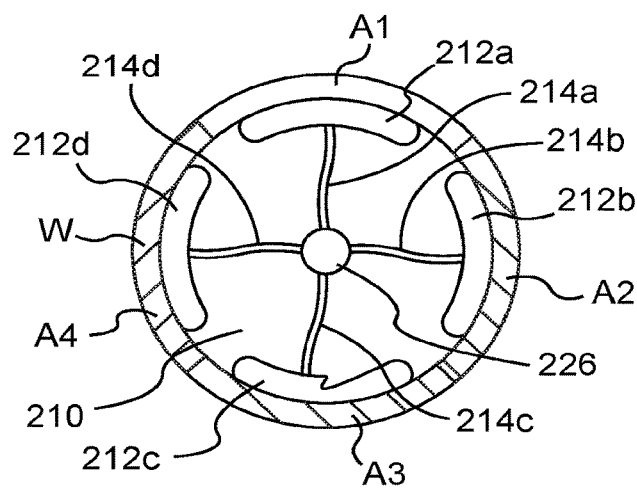
FIG. 9 illustrates a cross-sectional view of an example body lumen with an embodiment of an energy delivery body positioned therein.

It will be appreciated that when, for example, the second electrode 212b is energized and the other electrodes 212a, 212c, 212d are not energized, all of the energy flows along the second electrical pathway 216b to the dispersive electrode 140. Similarly, this can be repeated for the third electrode 212c wherein all of the energy flows along the third electrical pathway 216c, and the fourth electrode 212d wherein all of the energy flows along the fourth electrical pathway 216d. This can be easily achieved without rotation of the catheter 202 as illustrated in FIG. 9. FIG. 9 illustrates a cross-sectional view of a body lumen having walls W, wherein an energy delivery body 208 is positioned therein. The expandable member 210 of the energy delivery body 208 is expanded so that the first electrode 212a, second electrode 212b, third electrode 212c and fourth electrode 212d reside against the walls W of the body lumen. The electrodes 212a, 212b, 212c, 212d are then energized individually, in a sequence. Energizing first electrode 212a creates first treatment area A1, energizing second electrode 212b creates second treatment area A2, energizing third electrode 212c creates third treatment area A3, and energizing fourth electrode 212d creates fourth treatment area A4. Using such an electrode configuration, the entire ring of wall tissue can be ablated without leaving gaps, and in a more precise and less time-consuming manner than when rotating the catheter 212.

Focal delivery of energy, such as shown in FIG. 8, can be utilized in a variety of ways to improve and/or maximize the effect on the tissue. In particular, precise timing and sequencing of energy delivery to the electrodes (e.g. 212a, 212b, 212c, 212d) can be utilized to ensure cell death within the tissue receiving the energy, as will be described further below. This can be particularly useful in the treatment of atrial fibrillation. As mentioned previously, permanent conduction block across linear lesions uses and/or requires transmural lesions involving cell death rather than temporary reversible effects. In some embodiments, the PEF waveform is one that employs bipolar cancellation with a frequency that reflects a nanosecond to microsecond pulse duration to mitigate the extent of systemic muscle contraction to acceptably low levels, with or without a paralytic, while retaining its capacity to destabilize both the cell and organelle membranes. This induces a multi-modal effect on the cell that uniquely predisposes it to enhanced treatment outcomes beyond those attained with either nanosecond pulsed electric fields (nsPEFs) or traditional millisecond irreversible electroporation (IRE) methods. Thus, the delivered energy can induce sufficiently large and effective treatment zones in the targeted tissues, which is a challenge for nsPEFs, while maintaining an advantageous safety and muscle contraction profile, which is a challenge for traditional millisecond IRE, particularly for monopolar pulse delivery arrangements using an external dispersive pad.

When selecting the type of electrode for a given treatment indication, it is important to consider the advantages and disadvantages of electrode configurations that employ monopolar electric pulse delivery (e.g., the electrode circuit has an active portion of the electrode which completes an electrical circuit with a distant secondary electrode) versus bipolar or multipolar electric pulse delivery (e.g., both the delivery and return of the electric pulse energy is confined within the electrode device itself). When delivering electric pulses in monopolar circuit configurations, the total system impedance is relatively consistent, and there is a low to minimal chance of electrical arcing. This permits a very stable and controlled environment for delivering pulsed electric fields, as well as the use of considerably simpler electrode designs. However, when employing a distant return electrode in the circuit, the electrical energy is more dispersed throughout the body of the patient, which may limit the control of the affected area to some degree when very large lesions are desired. Further, it may result in additional muscle activation, which can be appropriately compensated for by careful pulsed electric field parameter selection to retain a treatment effect without muscle contraction, or by employing the use of a paralytic, which will thus also require general anesthesia for the procedure.

Conversely, bipolar and multipolar electrode designs face their own set of advantages and challenges in practical employment of therapeutic pulsed electric field delivery. The containment of all active portions of the electrical circuit enable very focused electrical energy delivery, allowing additional aspects of control of electric field distribution, and reducing the likelihood of muscle contraction.

However, because the electric current is so confined, system impedance can often be very low, and there can be a very high risk of electrical arcing for a given pulse protocol, which reduces the maximum usable pulsed electric field delivered voltage. These factors combine to severely limit the penetration depth of treatment effects, particularly in luminal applications. Further, because the treatment effect is highly sensitive to the separation distance of the electrodes in bipolar and multipolar electrode configurations, subtle fluctuations or variances in the contact region separation distances will reduce the predictability of treatment outcome at different target sites, particularly in luminal applications as the electrode is applied in targeted sites of varied geometry, requiring a varied deployment extent of the electrode, which can alter the electrode contact separation distances. Overcoming such aspects can result in further complexity to treatment device designs. Thus, while embodiments described herein can be adapted to both monopolar and bipolar/multipolar electrode circuit systems, it should be appreciated that appropriately-tuned monopolar treatment systems can offer a greater penetration depth of effect, improved treatment circumferential regularity, improved treatment zone predictability, and/or considerably simpler treatment delivery procedures for the operator, depending upon the application.

PEFs, when delivered at appropriate amplitude, waveform, frequency, repetition, and repetition rate, facilitate the destabilization of cell and organelle membranes. This results in a reduced capacity for the cell to maintain its desired intracellular and extracellular environment and to maintain proper function, which can ultimately result in destruction and/or removal of the cell from its location in tissue. In vivo, this initiates a complex cascade of tissue restructuring which is tissue-specific and can involve regeneration of the affected region with new cells and/or the generation of fibrotic scar formation. Cell and tissue-scale response to the pulsed electric fields may in part relate to the nature in which the cells are killed, as well as the regenerative capacity of the cells themselves. For instance, where liver is known to regenerate after partial surgical excision, it has likewise been shown to regenerate following death from pulsed electric fields. Cardiomyocytes and tissue in the antral region and atria, however, do not exhibit the same propensity for regeneration, and thus, following their cell death, there is a greater likelihood of fibroblast infiltration for depositing fibrin and other connective tissue components, replacing the affected region with a non-conductive patch of scar tissue as a natural part of the tissue healing process. By initiating this process using pulsed electric fields, it should be noted that the connective tissue deposition occurs as part of the natural healing process, whereas thermally-dependent ablation technologies will induce coagulative necrosis and inherently alter the structure of the proteins, resulting in a different healing process and scar type formation, which may result in increased patient risk for incidences of necrosis or unacceptable collateral damage to adjacent tissues, such as the esophagus or phrenic nerve.

When used to treat atrial fibrillation, PEFs offer several opportunities to serve as an effective therapeutic means for treatment. Because PEF effects are not dependent on thermal mechanisms, the blood perfusion heat sink effects can be considered irrelevant or even beneficial, for example in mitigating the risks for thermal damage-based adverse events. In addition, the improved safety for sensitive structures and tissues enables PEF treatments to be delivered in regions that are poorly suited for thermal ablation.

V. Phased Energy Delivery

Focal delivery of PEFs, as described above, can provide increased tissue lethality by employing precise timing and sequencing of energy delivery to the electrodes (e.g. 212a, 212b, 212c, 212d). To this end, embodiments of the present disclosure provides at least one energy delivery algorithm 252 designed according to advanced interval theory. Such algorithms 252 may be utilized by a tissue modification system, such as the pulmonary tissue modification system 100 illustrated in FIG. 1, or a similar system utilized for treatment of other body tissue and/or body lumens. In any case, the at least one algorithm 252 controls delivery of energy from a generator to the catheter 202 and energy delivery body 208.

In some embodiments, the algorithm 252 causes PEF energy to be delivered to each electrode in a singular or limited amount, which is then repeated multiple times to complete the treatment delivery. For example, as shown in FIG. 9, the energy can be provided to electrodes 212a, 212b, 212c, 212d sequentially in a clockwise arrangement. This rotation may be repeated one or more times. However, it will be appreciated that other sequences may be used, including energizing the electrodes individually in any sequence. It will be appreciated that the sequence in its entirety may be repeated or a subset of the sequence may be repeated. Likewise, a different sequence may be utilized for follow-on cycles The advanced delivery algorithms 252 of the present disclosure exploit the nature of membrane dynamics, including the generation and resolution of defects and pores, which is an ability that is unique to PEF delivery, particularly in monopolar treatment systems. Defect generation in a membrane occurs rapidly, on the order of nanoseconds for organelles, and hundreds of nanoseconds to microseconds for cell membranes. However, defect resolution and restoration to normal membrane structure occurs on the order of seconds to tens of seconds. This time differential can be utilized to manipulate collective injury time. Thus, the advanced delivery algorithms 252 deliver energy in a time sequence that increases the rate of collective injury over time and decreases the requisite voltage or number of total packets used to cause cell death circumferentially, around the span of the lumen perimeter. This is in contrast to the approach of merely adjusting the number of PEFs delivered to adjust treatment intensity. Increasing the number of PEFs not only extends treatment time but may involve the use of stronger generators, particularly when delivering energy to all electrodes at the same time throughout the duration of the procedure. Thus, the advanced delivery algorithms 252 decrease the number of PEF exposures to a particular region, concentrating the effects on generating membrane nanoscale defects rather than cumulative injury, wherein cells which are treated are ultimately killed rather than allowed to reverse. When an organelle or cell membrane is physically disrupted, the membrane can lose its ability to serve as an environmental barrier for the organelle or cell. To maintain viability, cells should retain homeostasis, by retaining the basic constituents for function and viability within the cell, while preventing or impeding the influx of undesirable quantities or materials from the external environment into the cell. Thus, when a cell membrane is disrupted, diffusion gradients drive materials out of and into the cell against the needs of the cell. When the injury induced by this loss of homeostasis surpasses the capacity of the cell and its remaining intracellular adenosine triphosphate (ATP) stores to recover from the effects and restore appropriate concentrations, the cell will die. This principle may also be applied to the organelle content leakage that occurs from PEFs, particularly the leakage of calcium and caspase 3 from certain organelles, both of which promote apoptosis of the cell. When the organelle is in a disrupted state for longer periods of time, the leakage of these contents can continue and become more difficult to reverse.

Figure 10:
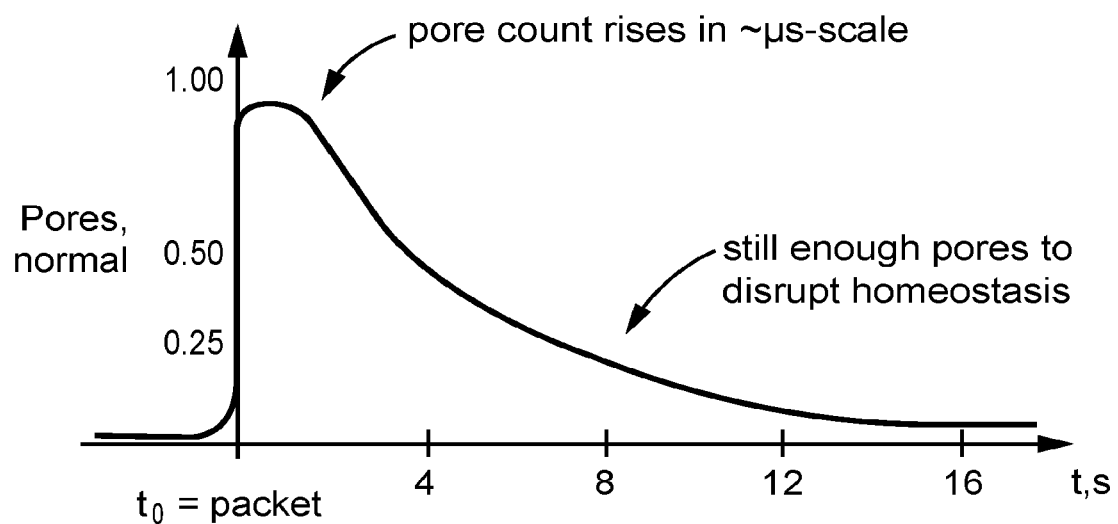
FIG. 10 is an example plot showing pore or defect formation over time in response to pulsed electric field (PEF) energy delivery.

Both organelle and cellular targets for affecting cell homeostasis will increase their lethality the longer that the defects are maintained in the cell. Where these defects are generated rapidly, and they resolve with logarithmic decay on the order of seconds, it can be concluded that PEFs only need to be delivered once every few-to-tens of seconds to maintain their continued injury to the cell. FIG. 10 is a plot showing an example of pore or defect formation over time in response to PEF energy delivery. It may be appreciated that pore, defect and opening are used interchangeably to describe an inconsistency in a cell or organelle wall, such as potentially leading to loss of homeostasis. As illustrated, pore count rises on a microsecond scale. Pore count then diminishes gradually over time. In this example, using a 4-second pore count half-life, approximately 25% of pores are still open, continuing to damage cell homeostasis, even 8 seconds after PEF application.

FIG. 11 illustrates pore or defect formation when PEF energy is delivered in intervals that are not optimized for lethality. In particular, FIG. 11 is a plot showing the effect of delivery of five packets (with rest periods between each packet) on pore count. Each of the five energy packet comprises a series of biphasic high voltage pulses. Thus, five peaks 350a, 350b, 350c, 350d, 350e are illustrated in FIG. 11, each reaching a maximum value of pore count. In this example, after five packets are delivered, the pore count decreases over time so that approximately 25% of pores are still open, damaging cell homeostasis, at 13 seconds (indicated by location 352 along the curve). FIG. 12 is a plot showing another example of the delivery of five packets, wherein each energy packet includes a series of biphasic high voltage pulses. Thus, five peaks 350a, 350b, 350c, 350d, 350e are illustrated, each reaching a maximum value of pore count. However, in this example, the rest periods between each packet are such that subsequent PEFs are delivered close enough to maintain disrupted membranes but far enough apart to increase the cumulative amount of cell contents leakage. Consequently, cell damage occurs over a longer period of time. In this example, pores decrease over time so that approximately 25% of pores are still open, damaging cell homeostasis, at 25 seconds (indicated by location 354 along the curve). Thus, it is not only the number of PEFs but also the cadence of PEF delivery delivered that will affect the lethality of a PEF regimen. Another aspect of this extended disruption, particularly when the defects are provided time to resolve, is that the cell will continually be expending energy (ATP) to restore the appropriate intra- and extra-cellular and organelle material balances to maintain function. As defects are repeatedly generated or continually maintained for longer periods of time, the cell will continue using energy to restore homeostasis, depleting energy stores for other functions vital to its continued viability, thus increasing the likelihood of necrotic or apoptotic cell death for longer affected periods.

According to some embodiments of the present disclosure, such extended disruption is achieved by one or more algorithms which cause delivery of PEFs to one or more electrodes in a sequence. The sequence of PEFs is applied to the electrodes (e.g. 212a, 212b, 212c, 212d) individually while using monopolar delivery (i.e. each electrode is electrically communicating in sequence with the external dispersive electrode 140). As mentioned, one or more algorithms are typically controlled and automated by the generator and eliminate the need for rotation or manipulation of the catheter 202.

Figure 13:
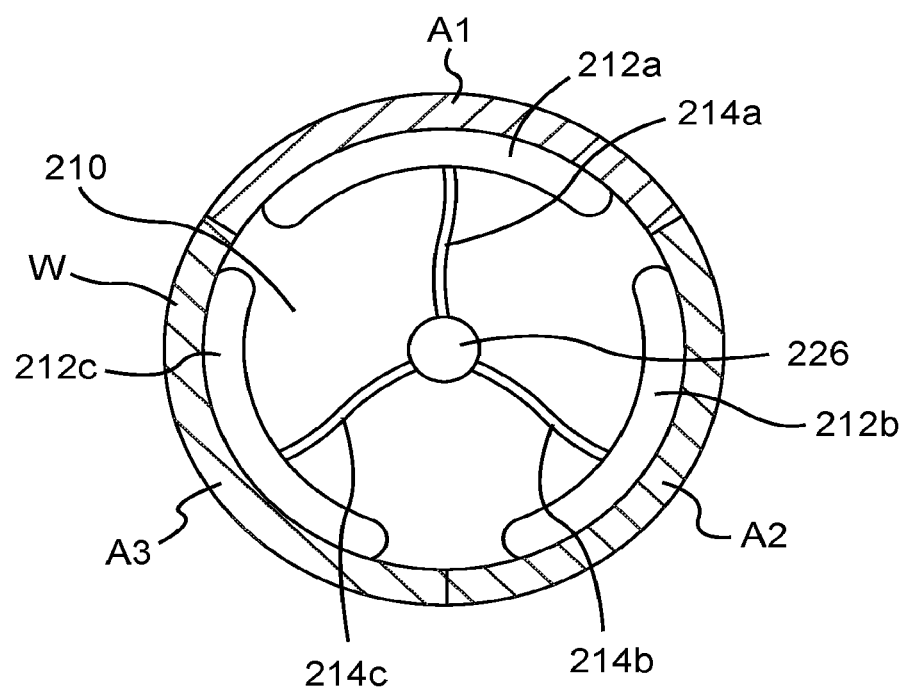
FIG. 13 illustrates a cross-sectional view of an example body lumen having walls, with an energy delivery body positioned therein.

FIG. 13 illustrates a cross-sectional view of a body lumen having walls W wherein an energy delivery body 208 is positioned therein. Here, the energy delivery body 208 includes an expandable member 210 having a first electrode 212a, a second electrode 212b and a third electrode 212c which are sized and oriented along the expandable body 210 so as to be positionable and ablate a continuous ring along the inner surface of the walls W of the body lumen. Thus, each electrode delivers energy to approximately a third of the circumferential lumen wall. The electrodes 212a, 212b, 212c are energized individually, in a sequence. Energizing first electrode 212a creates first treatment area A1, energizing second electrode 212b creates second treatment area A2, energizing third electrode 212c creates third treatment area A3. Not only are each of the treatment areas receiving electrical energy, but the smaller electrode sizes increases the amount of tissue receiving energy due to boundary effects of the electrodes. Electric current is concentrated at sharp edges and boundaries of electrodes. Therefore, electric fields are stronger at the edges of an electrode than at its center. Therefore, with multiple smaller electrodes, more of the tissue is receiving the depth of the boundary effects rather than the dip in electric field depth that would occur at the center of the electrode. This improves luminal coverage wherein the entire ring of wall tissue is ablated without leaving gaps.

FIGS. 14-15 are plots showing the concepts of FIGS. 11-12 as they relate to delivery to multiple electrodes (212a, 212b, 212c) rather than a single electrode. FIG. 14 is a plot showing the effects of delivering a plurality of PEFs (five packets) to each electrode 212a, 212b, 212c in a serial manner. It will be appreciated that each energy packet comprises a series of biphasic high voltage pulses. To begin, five packets are delivered to the first electrode 212a while no energy is supplied to the second electrode 212b and third electrode 212c. Then five packets are delivered to the second electrode 212b while no energy is supplied to the first electrode 212a and third electrode 212c. Then five packets are delivered to the third electrode 212c while no energy is supplied to the first electrode 212a and second electrode 212b. FIG. 14 illustrates pore count over time for each treatment area (A1, A2, A3). As shown, each trace decreases over time so that approximately 25% of pores are still open, damaging cell homeostasis, at 13 seconds from the time the first packet was delivered to the corresponding electrode. Thus, FIG. 14 illustrates the concept of FIG. 11 repeated for each treatment area. Thus, although effective in creating a continuous lesion, the PEF energy delivery is not optimized for lethality to cells.

It will be appreciated that optimization of lethality may be achieved by delivering a plurality of PEFs (e.g. five packets) to each electrode 212a, 212b, 212c in a serial manner wherein each packet is spaced apart by rest periods that increase and/or maximize the cumulative contributors to cell death. However, such a sequence would prolong the treatment period. To curtail this, alternative sequences are provided which decrease and/or minimize treatment time while maintaining a desired amount and/or optimization of lethality. In one embodiment, the sequence involves delivering the spaced apart packets in an overlapping pattern to the electrodes 212a, 212b, 212c rather than a serial pattern; the effects of which are illustrated in FIG. 15. For example, a first packet is delivered to electrode 212a, then a first packet is delivered to electrode 212b and a first packet is delivered to electrode 212c. This completes one round or rotation of the sequence pattern. Then, a second packet is delivered to electrode 212a, a second packet is delivered to electrode 212b and then a second packet is delivered to electrode 212c. This pattern is repeated until five packets are delivered to each electrode 212a, 212b, 212c. The packets are delivered to each electrode with rest periods that cause cell damage to occur over a longer period of time. Recall, pore count decreases over time so that approximately 25% of pores are still open, damaging cell homeostasis at 21 seconds. Thus, shortly after 21 seconds, a continuous lesion around the circumference of the body lumen has been created with increased lethality and transmural penetration. This is in contrast to waiting three times as long (in this example, because there are three electrodes spanning the circumference) to achieve a similar result by delivering energy to the electrodes in a serial manner. Likewise, by overlaying the cycles, instead of delivering all PEFs to each contact region entirely before progressing to the next PEF, the entire circumference of the targeted region experiences the organelle and cell membrane defects for a longer duration of time for the same number of total PEFs delivered.

The benefits of using a multi-electrode energy delivery body 208 operating in monopolar fashion include:
 a. increased lethality,
 b. mitigation of preferential current pathway effects, and thus reduced individual PEF energy requirements which permits lower generator power demands,
 c. less collateral damage risk to regional tissues due to lower voltages,
 d. fewer total PEFs,
 e. decreased, if any, thermal effects,
 f. reduced, if any, muscle contraction, and
 g. reduced risk for induced cardiac arrythmias (particularly for non-cardiac applications of the present disclosure).

Another approach to exploit the benefits of advanced interval theory incorporates the use of maintenance PEFs. Energy requirements may be further reduced by replacing some of the PEFs in a delivery sequence with maintenance PEFs. Maintenance PEFs have a reduced intensity in comparison to regular or primary PEFs. The initial generation of membrane defects involves relatively strong transmembrane potentials to be generated in cells exposed to the electric field from PEFs. However, after the effects have been generated, the local region impedance decreases due to improved electric current pathways through (rather than around) the cells. Further, a balance is generally created between cell defects permitting electrolyte mobility across and through the cell, the electric field intensity, and the size, count, and distribution of defect generation. Thus, after crossing the initial energy barrier threshold to induce the defects, the transmembrane potential decreases significantly, as does its dielectric capacity. This means that maintaining the defects for longer periods of time may be permitted by subsequent exposure to electric fields or PEFs at a lower intensity than those required to generate the defects. Thus, rather than increasing the effectiveness of a PEF treatment with additional PEFs, maintenance PEFs may be delivered to the targeted regions in addition to the primary PEFs, which increases effectiveness without significantly increasing energy requirements.

Figure 16:
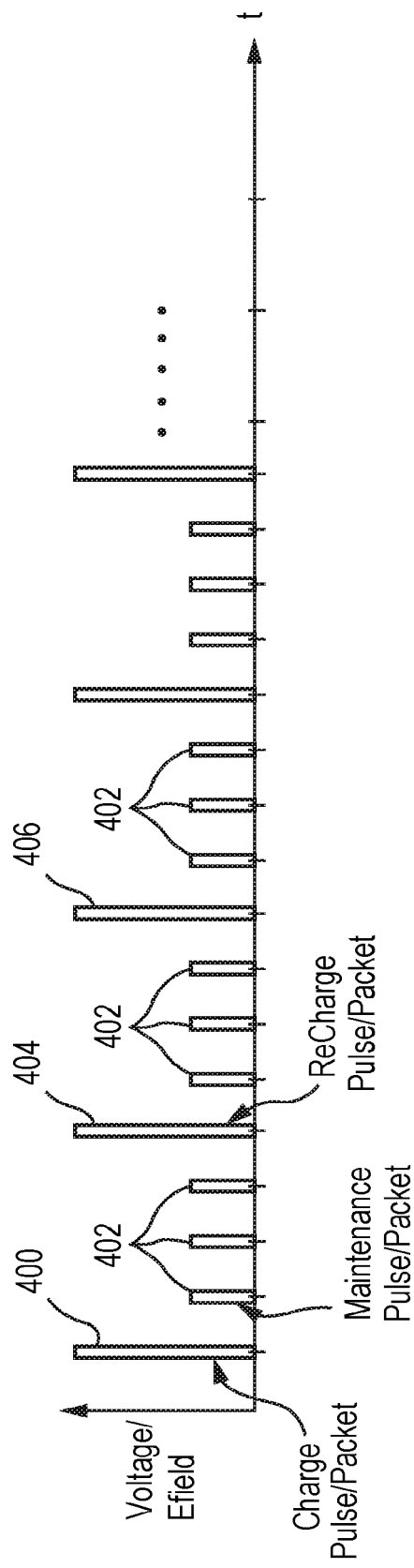
FIG. 16 is a plot showing an example sequence of PEFs, the sequence including primary PEFs and maintenance PEFs therebetween.

FIG. 16 is a plot showing a sequence of PEFs comprising primary PEFs and maintenance PEFs therebetween. It will be appreciated that the PEFs may be considered pulses or packets. Referring to FIG. 16 a first primary PEF 400 is shown followed by three maintenance PEFs 402. A second primary PEF 404 then follows, followed by three maintenance PEFs 402, and a third primary PEF 406 then follows, followed by three maintenance PEFs 402, etc. It will be appreciated that any number of maintenance pulses may be used and may form a regular pattern (as shown in FIG. 16) or an irregular pattern, such as having differing numbers of maintenance pulses between primary pulses. Likewise, it will be appreciated that the maintenance pulses may have the same or differing intensity throughout the delivery sequence.

Figure 17:
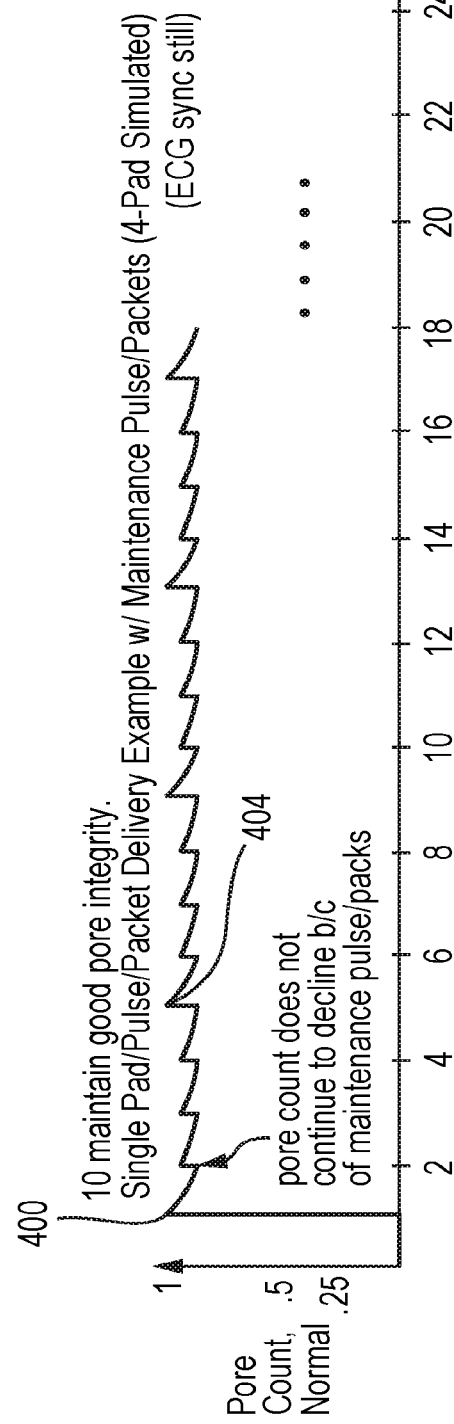
FIG. 17 is a plot showing an example effect of the delivery sequence of FIG. 16 on pore count in a target membrane.

FIG. 17 is a plot showing the effect of a delivery sequence as in FIG. 16 on pore count in a target membrane. As shown, the pore count reaches a maximum level upon receiving the first primary PEF 400. Pore count then declines until receiving a maintenance PEF 402 which then restores the pore count toward the maximum level. This repeats for each maintenance PEF 402 and then for later primary PEFs and follow on maintenance PEFs. It will be appreciated that in some instances the maintenance PEFs are sufficient to restore the pore count (such as "topping off") so that later primary PEFs are not needed as frequently, or not needed altogether.

It will be appreciated that sequences including maintenance PEFs 402 may be delivered to multiple electrodes in the same way as sequences including only primary PEFs. For example, in relation to FIG. 13, a first packet may be delivered to electrode 212a, then a first packet is delivered to electrode 212b and a first packet is delivered to electrode 212c. This completes one round or rotation of the sequence pattern. Then, a first maintenance packet is delivered to electrode 212a, a first maintenance packet is delivered to electrode 212b and then a first maintenance packet is delivered to electrode 212c. This pattern is repeated until four maintenance packets are delivered to each electrode 212a, 212b, 212c. This would involve the delivery of five total packets (one primary followed by four maintenance) to each electrode 212a, 212b, 212c in an overlapping fashion. In some instances, this would have the same effect as the delivery of five primary packets with the additional time saving benefit of overlapping the cycles.

Typically, follow-on PEFs are delivered immediately after primary PEF delivery (e.g., 1-100 ms following completion of the primary PEF) so that all of the PEFs are delivered in a safe period of the cardiac rhythm. As mentioned, in some embodiments, the energy signal is synchronized with the patient's cardiac cycle to prevent induction of cardiac arrhythmias. Thus, the patient's cardiac cycle is typically monitored with the use of an electrocardiogram (ECG). A typical ECG trace includes a repeating cycle of a P wave representing atrial depolarization, a QRS complex representing ventricular depolarization and atrial repolarization, and a T wave representing ventricular repolarization. To safely deliver energy in close proximity to the heart, synchronization between energy delivery and the patient's cardiac cycle is often employed to reduce the risk of cardiac arrhythmia. High voltage energy can trigger a premature action potential within the cardiac muscle as the delivered energy increases the cardiac muscle cell membrane permeability allowing ion transport, which can induce cardiac arrhythmias, especially ventricular fibrillation. To avoid cardiac arrhythmias, the electrical energy is delivered to the airway in a fashion that is outside the "vulnerable period" of the cardiac muscle.

Within one cardiac cycle (heartbeat), the vulnerable period of the ventricular muscle is denoted on an ECG by the entire T wave. Typically, for ventricular myocardium, the vulnerable period coincides with the middle and terminal phases of the T wave. However, when high energy pulses are delivered in close proximity to the ventricle, the vulnerable period can occur several milliseconds earlier in the heartbeat. Therefore, the entire T wave can be considered to be within the vulnerable period of the ventricles.

The remaining parts of a cardiac cycle are the P wave and the QRS complex, which both include periods when atrial or ventricular muscle is refractory to high voltage energy stimuli. If high voltage energy pulses are delivered during the muscle's refractory period, arrhythmogenic potential can be minimized. The ST segment (interval between ventricular depolarization and repolarization) of the first cardiac cycle and the TQ interval (interval including the end of the first cardiac cycle and the mid-point of the second cardiac cycle) are the periods where high voltage energy can be delivered without induction of cardiac arrhythmia due to the cardiac muscle being in a depolarized state (refractory period).

However, because the maintenance PEFs are delivered with lower electrical energy than the primary PEFs (higher frequency, lower voltage, fewer cycles, etc.), in some instances it is possible to deliver the maintenance PEFs periodically between the primary PEFs (such as during the "vulnerable periods") without risk of inducing aberrant cardiac rhythms in the patient. This latter aspect is particularly applicable to non-cardiac applications, such as delivery in the airways, due to their more distant physical proximity from the heart and thus inherently lower procedural risk for inducing arrhythmia. When delivering this way, it may be possible to provide any number of maintenance PEFs between the primary PEFs. FIGS. 18A-18D illustrate an embodiment of a monopolar focal energy delivery sequence using maintenance PEFs during various portions of the cardiac cycle. FIGS. 18A-18D provide cross-sectional illustrations of an embodiment of an energy delivery body 208 having three electrodes 212a, 212b, 212c spaced around the circumference of an inflatable member 210. When energy is delivered to one of the electrodes, an electrical pathway is formed to the external dispersive electrode 140. In particular, FIG. 18A illustrates a first primary PEF 400 delivered to a first electrode 212a. This occurs during a safe period of the cardiac rhythm. FIG. 18B illustrates maintenance PEFs 402 delivered to each of the electrodes 212a, 212b, 212c outside of the safe period. Such delivery may be simultaneous or staggered. FIG. 18C illustrates a second primary PEF 404 delivered to a second electrode 212b during a safe period of the cardiac rhythm. FIG. 18D illustrates maintenance PEFs 402 delivered to each of the electrodes 212a, 212b, 212c outside of the safe period. This pattern may be repeated any number of times.

It will be appreciated that in some embodiments a maintenance PEF 402 is delivered to an electrode at the same time as a PEF (primary or maintenance) is delivered to a different electrode on the energy delivery body 208. When being delivered synchronously with the primary PEF, there may be some dilution of some focal delivery PEF benefits, since the energy is not being distributed in a purely focal fashion. This will also utilize electrical generators capable of maintaining the targeted therapeutic PEF parameter characteristics, as well as to deliver differential voltages to different electrode regions simultaneously. This concept is illustrated in FIGS. 19A-19B. FIG. 19A illustrates a primary PEF delivered to a first electrode 212a of a 4-electrode energy delivery body 208 while no energy is delivered to a second electrode 212b, third electrode 212c, and fourth electrode 212d. An effect zone is illustrated in dashed line indicating the active area of energy delivery. FIG. 19B illustrates the primary PEF delivered to the first electrode 212a while maintenance PEFs are delivered to the second electrode 212b, third electrode 212c, and fourth electrode 212d. As illustrated, the effect zone, as indicated in dashed line, extends more widely and around the broad surface of the electrode 212a and less deeply into the adjacent tissue (away from the electrode) because the energy focus is diluted around the circumference of the expandable member 140 due to the maintenance PEFs. In a further example, wherein the energy delivery body 208 comprises three electrodes distributed circumferentially therearound, a primary PEF may be delivered to a first electrode 212a at 3000 V while but the other two electrodes 212b, 212c each receive a 500 V PEF of the same polarity. Again, this may cause some dilution of the benefits from using the focal delivery due to slightly increased electrical conductivity at the tissue receiving maintenance PEFs. This can enable some preferential current pathway effects, as well as increased generator electrical demands to generate multi-voltage signals for delivery. However, in some embodiments, delivering the maintenance PEFs to some electrodes concurrently with the primary PEFs to other electrodes will allow all PEFs to be delivered in the safe cardiac rhythm window, rather than delaying time periods for delivering maintenance-only sets of PEFs.

It will be appreciated that the above examples are illustrative and not considered limiting in scope. Primary PEFs and maintenance PEFs may be provided to the various electrodes in any combination or pattern. For example, in some embodiments having three electrodes 212a, 212b, 212c, a primary PEF is provided to first electrode 212a followed by maintenance pulses simultaneously applied to all three electrodes 212a, 212b, 212c. Then a primary PEF is applied to the second electrode 212b followed by maintenance pulses simultaneously applied to all three electrodes 212a, 212b, 212c. Then a primary PEF is applied to the third electrode 212c followed by maintenance pulses simultaneously applied to all three electrodes 212a, 212b, 212c. This pattern may be repeated any number of times. Likewise, in some embodiments, a primary PEF is applied to the first electrode 212a, then to the second electrode 212b and then to the third electrode 212c. This is followed by maintenance pulses applied to all three electrodes 212a, 212b, 212c. This pattern may be repeated any number of times. In some embodiments, a primary PEF is applied to the first electrode 212a and maintenance PEFs are applied to the second electrode 212b and third electrode 212c. Then a primary PEF is applied to the second electrode 212b and maintenance PEFs are applied to the first electrode 212a and third electrode 212c. Then a primary PEF is applied to the third electrode 212c and maintenance pulses are applied to the first electrode 212a and second electrode 212b. Such examples illustrate a small sampling of various combinations.

In some embodiments, maintenance PEFs are used to determine treatment characteristics by measuring a particular variable, such as impedance, which is indicative of the treatment characteristic. Since maintenance PEFs have a lower energy than primary PEFs, the effects on the tissue due to the PEF will be less (therefore affecting the treatment environment less) thereby providing more useful data.

Thus, lower strength PEFs, which cause less tissue-level major effects, provide cleaner data to indicate aspects such as treatment effect accumulation/progression, tissue temperature, cellular density and composition, regional cell viability, and other tissue aspects. Due to the local nature of the electrical circuit system with bipolar and multipolar electrode delivery schemes, applications for this concept are particularly well-suited to such electrode device designs.

It will be appreciated that many of the concepts provided herein can be applied to bipolar delivery. For example, maintenance PEFs can be delivered in a bipolar fashion, even when primary PEFs are delivered monopolar. FIGS. 20A-20D illustrate such a delivery sequence. FIGS. 20A-20D provide cross-sectional illustrations of an embodiment of an energy delivery body 208 having four electrodes 212a, 212b, 212c, 212d spaced around the circumference of an inflatable member 210. When a first primary PEF 400 is delivered to the first electrode 212a in a monopolar configuration, an electrical pathway is formed to the external dispersive electrode 140, as illustrated in FIG. 20A. This occurs during a safe period of the cardiac rhythm. FIG. 20B illustrates maintenance PEFs 402 delivered to each of the electrodes 212a, 212b, 212c, 212d in a bipolar fashion outside of the safe period. When another safe period is reached in the cardiac rhythm, a second primary PEF 404 is delivered to a second electrode 212b in a monopolar fashion as illustrated in FIG. 20C. Again, an electrical pathway is formed to the external dispersive electrode 140. FIG. 20D illustrates maintenance PEFs 402 delivered to each of the electrodes 212a, 212b, 212c, 212d in a bipolar fashion outside of the safe period. This pattern may be repeated any number of times.

In addition to maintaining pores open longer, maintenance pulses can also be used to gather system-level (monopolar) or local-level (bipolar) data on the condition of the targeted region. This could include basic pulse metrics (Z', i', etc) with the lower parameter settings or use more advanced sensing and deduction techniques, such as evaluating spectroscopy data or multi-frequency data points which could indicate tissue characteristics such as tissue composition, effect depth/size/efficacy, temperature, macromolecule uptake, etc.

Although it has been described herein that primary PEFs are applied to a single electrode at a time to obtain focal delivery effects, it will be appreciated that focal delivery effects may also be achieved by delivering energy to more than one electrode in particular circumstances. For example, FIG. 21A illustrates an embodiment of an energy delivery body 208 having eight electrodes 212a, 212b, 212c, 212d, 212e, 212f, 212g, 212h disposed around the circumference of an inflatable or expandable member 210. In this embodiment, the electrodes function in pairs. For example, electrodes 212a, 212b are disposed adjacent to each other and therefore can mimic the action of a single electrode when energy is delivered to the electrodes 212a, 212b at the same time. Likewise, electrodes 212c, 212d can pair and act as a single electrode as can 212e/212f and 212g/212h. Having pairs of electrodes rather than single electrodes allows for the use of smaller electrodes which may be beneficial for expansion and contraction of the expandable member 210 and/or other design features. It will be appreciated that any number of electrodes may be used wherein electrodes function in groups rather than pairs. For example, FIG. 21B illustrates an embodiment of an energy delivery body 208 having nine electrodes 212a, 212b, 212c, 212d, 212e, 212f, 212g, 212h, 212i disposed around the circumference of an inflatable member 210. In this embodiment, the electrodes function in threes: 212a/212b/212c, 212d/212e/212f, and 212g/212h/212i. Thus, electrodes 212a, 212b, 212c are disposed adjacent to each other and therefore can mimic the action of a single electrode when energy is delivered to the electrodes 212a, 212b, 212c at the same time. Thus, electrodes may function in groups of any size including two, three, four, five, six or more. Likewise, the groupings may change throughout a sequence to maximize treatment effect. For example, groupings such as 212a/212b/212c, 212d/212e/212f, and 212g/212h/212i during one portion of a sequence may change to 212b/212c/212d, 212e/212f/212g, and 212h/212i/212a during another portion of the sequence.

Likewise, it will be appreciated that differing levels of energy may be delivered to adjacent electrodes. For example, rather than a pair of electrodes receiving energy to act as a single electrode, a first electrode of the pair may receive a primary PEF and second electrode of the pair may receive a maintenance PEF. In this instance, the second electrode receiving the maintenance PEF effectively extends the coverage of the first electrode by adding some "top off energy" to its boundaries. This will improve the radial coverage of the first electrode.

In some embodiments, drugs or therapeutic agents are delivered in combination with PEFs. Such delivery of agents may precede PEF delivery, overlap PEF delivery or follow PEF delivery. In some embodiments, such combinatorial treatments generate a stronger effect for a given PEF delivery algorithm. In some instances, this is preferred to delivering more PEFs to increase effect. It will be appreciated that in some instances the stronger effect with combinatorial treatments may not be as great as adding additional PEFs which may be beneficial depending on the choice of therapeutic agent and the result desired. In some embodiments, adding delays may keep at least the larger pores open long enough to still receive therapeutic agents. In some embodiments, maintenance PEFs are utilized which are monophasic, weaker (very low voltage) and optionally long (1 us to 10 ms) to encourage electrokinetically driven adjuvant drug uptake. In such situations, the cells would still maintain some pore opening, but the PEFs would now be more designed to move therapeutic agents around and "push" them into cells.

A variety of therapeutic agents may be used, such as chemotherapeutic agents, gene therapy targeting particular tissue types, and immunotherapy (such as CAR-T, with the added advantage of reducing the systemic toxicity (cerebral edema)), to name a few. When treating cardiac tissue, therapeutic agents may include anti-arrhythmic drugs, such as amiodarone to "quiet down" the ectopic foci. When treating pulmonary tissue, therapeutic agents may include steroids and other anti-inflammatory drugs. When treating tissue in the gastrointestinal tract, therapeutic agents may include steroids and anti-TNF agents that are used for Inflammatory Bowel Disease. Such examples are illustrative and are not considered limiting.

Thus, it will be appreciated that specialized catheter designs (including varied sized electrodes, multiple electrodes, therapeutic agent delivery mechanisms, etc.) and distinct energy delivery algorithms (including interval delivery, maintenance PEFs, monopolar/bipolar coordination, etc.) in various combinations can have a multitude of desired effects on the effective contact area including focality and depth. This serves as a powerful method to tune the circumferentiality and depth of effect of a therapeutic energy delivery catheter 202 at a given generator capacity and PEF settings. This is also achieved without extending treatment time, increasing the risk of muscle contraction, increasing collateral damage, or increasing the risk of inducing cardiac arrhythmias during the procedure. In many instances, a desired combination of these techniques enables faster treatment times, reduced muscle contraction, reduced collateral damage, and/or reduced risk of cardiac arrhythmia induction.

It will be appreciated that the catheter designs set forth herein are examples and are not intended to limit the scope of the present disclosure. Additional designs are provided to further illustrate example embodiments. For example, in some embodiments, the energy delivery body 208 of the therapeutic energy delivery catheter 202 is designed for monopolar delivery wherein the electrode 212 is comprised of a plurality of wires or ribbons 220 constrained by a proximal end constraint 222 and a distal end constraint 224 forming a spiral-shaped basket as illustrated in FIG. 22. Since the energy delivery body 208 is configured for monopolar energy delivery, the basket acts as a single electrode. Portions of the energy delivery body 208 are insulated so as to reduce the size and contour of the electrode 212 for focal delivery. FIG. 22 illustrates insulation material 300 covering a portion of the energy delivery body 208 (indicated by shading) leaving another portion exposed which is considered the electrode 212. Such insulation may be achieved by a variety of methods. For example, insulation may be achieved by coating the spiral-shaped basket with insulation material 300, such as silicone, and either removing the insulation material 300 in a desired area to expose the wires 220 in the shape of the electrode 212 or masking a desired area of the wires 220 prior to coating with the insulation material 300 and then removing the masking to expose the wires 220 in the shape of the electrode 212. Coating may be achieved by a variety of methods, such as dipping, spraying or vapor deposition, to name a few. Alternatively, the insulation could be attained by masking portions of the energy delivery body 208, such as a spiral-shaped basket, when the body 208 is expanded. This may be achieved by positioning the energy delivery body 208 within a balloon or other compliant masking material wherein the material has one or more portions removed, such as creating one or more windows. Expansion of the energy delivery body 208 presses the body 208 against the material, and optionally expands the material. Portions of the energy delivery body 208 exposed through the one or more windows would be able to deliver energy while covered portions would be insulated. This would avoid coatings on wires or braids that rely on distances between individual braid wires to be mobile.

Figure 23:
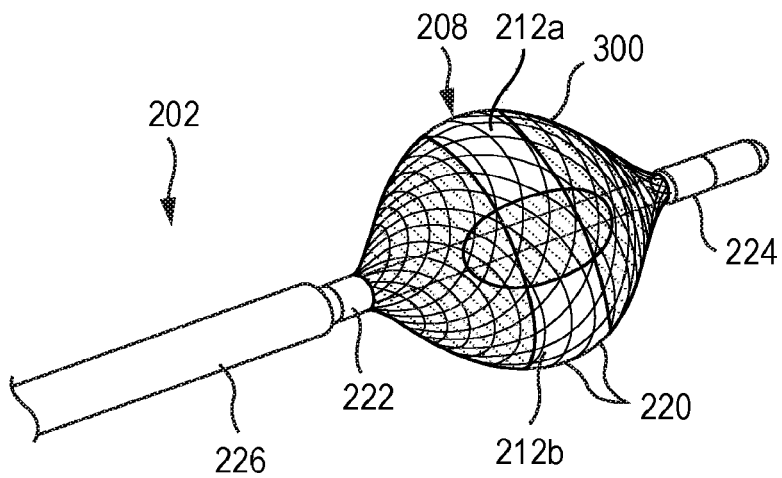
FIG. 23 illustrates an example insulation material covering a portion of an energy delivery body and leaving two portions exposed, thereby creating a first electrode and a second electrode.

In other embodiments, the wires 220 or portions of the wires 220 are insulated prior to braiding into the spiral-shaped basket. Portions of the insulation material 300 can then be removed after braiding to create the electrode 212. In some embodiments, where the energy delivery bodies 208 have some or all of the wires 220 independently activatable, multiple electrodes may be created around or along the energy delivery body 208 by similar methods. This is achieved by strategically removing or masking insulation material 300 so as to reveal wires 220 which are independently activatable. For example, FIG. 23 illustrates insulation material 300 covering a portion of the energy delivery body 208 (indicated by shading) leaving two portions exposed creating a first electrode 212a and a second electrode 212b. These electrodes 212a, 212b are independently activatable due to the structure and orientation of the wires 220.

Figure 24:
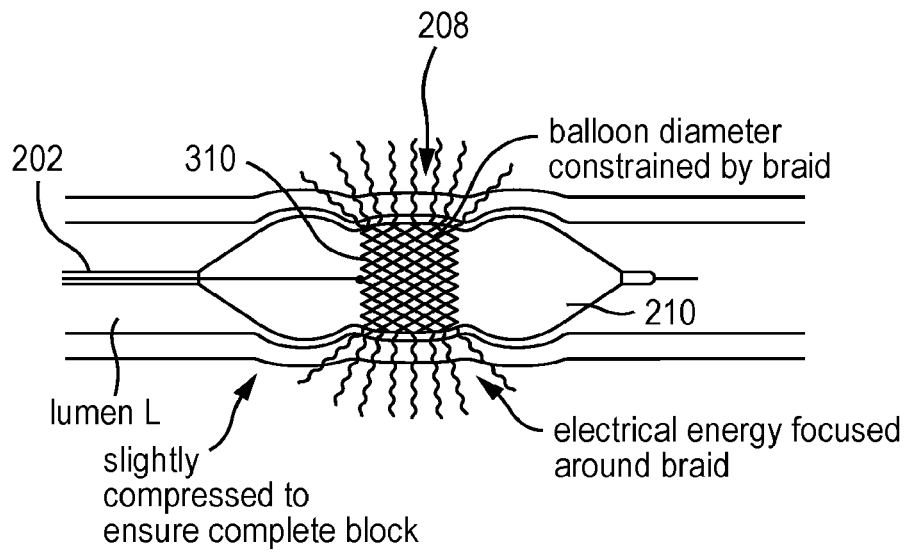
FIG. 24 illustrates an example electrode comprising a ring wherein energy delivered through the ring is focused and restricted to the area of the ring by an expandable member which is inflated through and around the ring.

It will be appreciated that there are implications to delivering pulsed electric fields to target lumens or tissue that contains or is adjacent to an electrically conductive medium, such as blood. If the electrode is not appropriately isolated to force pulse delivery into the tissue wall and the electrically conductive medium is thus exposed to the pulses, some of the electric current will flow through the conductive medium rather than the targeted tissue wall. While this will likely not pose risks for an adverse event due to the low cumulative energy delivered in pulsed electric field treatments, it can dilute or weaken the electric field distribution, thereby reducing the electric field intensity penetration depth into the tissue. This is a similar effect to the aforementioned dependence of electric field intensity on the electrode contact surface area, whereby the blood is serving as a semi-conductive virtual electrode. Thus, some embodiments of the electrode designs and energy delivery protocols are designed to overcome this effect, such as by appropriately tuning the pulse parameters or designing electrode devices able to restrict the amount of pulse exposure to the conductive medium. It will be appreciated that, while a thin layer of conductive mucus lines the airways and other similar potential luminal targets, the volume available for dilution of electric field intensity is often less, and thus there is a reduced need to overcome this effect in these targeted indications. However, this effect is more significant in vascular targets, and serves as one additional challenge for attaining transmural circumferential lesions. It will be appreciated that in some embodiments the energy delivery body 208 is mechanically expandable itself and in other embodiments the energy delivery body 208 is expandable with the use of an expandable member 210. When utilizing an expandable member 210, the expandable member 210 itself can act as an insulator. For example, in FIG. 24 the electrode 212 includes a ring 310. The energy delivered through the ring 310 is focused and restricted to the area of the ring 310 by an expandable member 210 which is inflated through and around the ring 310, as shown. In this embodiment, the diameter of the expandable member 210 is restricted by the ring 310 in the area of the ring 310. However, the portions of the expandable member 210 that extend beyond the edges of the ring 310 are able to expand further, slightly compressing the surrounding tissue of the body lumen L. This creates a complete or substantially complete block of energy, limiting the energy delivery to the area of the ring 310. It will be appreciated that such design may be particularly useful in environments having an electrically conductive medium, such as blood, wherein energy is directed into the tissue without delivery to the blood. It may also be appreciated that inflation of an expandable member within an energy delivery body having a basket shape, such as illustrated in FIGS. 22-23, may also resist delivery of energy to blood in a vascular lumen.

Figure 25:
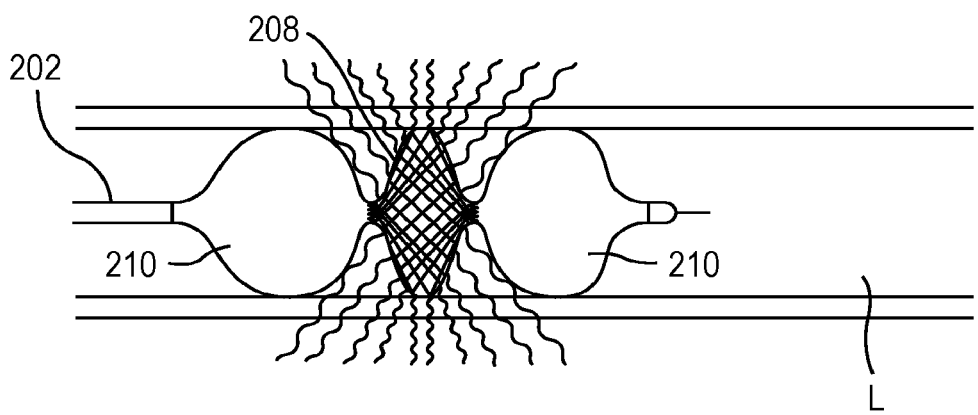
FIG. 25 illustrates an example electrode including a disc, configured such that energy delivered through the disc is focused and restricted by expandable members disposed on both sides of the disc.

FIG. 25 provides a similar embodiment wherein expandable members 210 act as insulators. In this embodiment, the energy delivery body 208 comprises a plurality of wires or ribbons 220 forming a spiral-shaped basket in the form of a disc. In this embodiment, the energy delivery body 208 is self-expanding. Expandable members 210 are disposed on both sides of the energy delivery body 208. Upon expansion against the body lumen L, the expandable members 210 create a complete block of energy, limiting the energy delivery to the area of the energy delivery body 208. It will be appreciated that in some embodiments the energy delivery body 208 is expandable by an internal expansion member, rather than self-expanding. Optionally, this internal expansion member may be expandable in unison with the expandable members 210 on both sides of the energy delivery body 208, such as by an interconnected inflation lumen.

It will be appreciated that a variety of catheter designs having insulated regions may additional provide reduced flow through the body lumen. When utilized in blood vessels, this reduces blood flow, which may be beneficial in some procedures.

It will be appreciated that many of the catheter designs and algorithms described herein may be utilized in the delivery of a variety of types of energy, not limited to biphasic PEF delivery. Such additional varieties of energy and energy-based treatments include, but are not limited to, electrochemotherapy, nanosecond pulsed electric fields, irreversible electroporation, electrochemical treatment, and electrogenetherapy.

While embodiments of the present disclosure have been shown and described herein, it will be apparent to those skilled in the art that such embodiments are provided by way of example only. Numerous variations, changes, and substitutions will now occur to those skilled in the art without departing from the scope of the present disclosure. It should be understood that various alternatives to the embodiments described herein may be employed when implementing systems and methods of the present disclosure.

What is claimed is:

1. A system for treating a passageway within a body comprising:
    a catheter comprising a first electrode and at least one additional electrode disposed near its distal end, wherein the distal end of the catheter is configured to be positioned within the passageway so that the first electrode and the at least one additional electrode are able to transmit pulsed electric field energy to an inner circumference of the passageway which destroys at least a portion of cells within a cellular matrix along the inner circumference without destroying the cellular matrix; and
    a generator in electrical communication with the first electrode and the at least one additional electrode, wherein the generator includes at least one energy delivery algorithm that
        a) provides an electric signal of the pulsed electric field energy to the first electrode so as to prioritize energy delivery through the first electrode to create a first treatment area and
        b) switches to individually provide an electric signal of the pulsed electric field energy to each of the at least one additional electrodes so as to prioritize energy delivery through each of the at least one additional electrodes when provided the electric signal so as to create an additional treatment area corresponding to each of the at least one additional electrodes,
    wherein the first treatment area and the additional treatment areas extend along the inner circumference of the passageway so as to create a functionally continuous treatment area spanning the inner circumference.

2. The system as in claim 1, wherein the passageway is disposed within a heart and the distal end of the catheter is configured to be positioned within the heart, and wherein the at least one energy delivery algorithm includes signal parameters causing the functionally continuous treatment area to comprise an electrical disconnection between a pulmonary vein and a left atrium so as to treat arrhythmia.

3. The system as in claim 2, wherein the passageway comprises the pulmonary vein and the distal end of the catheter is configured to be positioned within the pulmonary vein.

4. The system as in claim 3, wherein the signal parameters cause the functionally continuous treatment area to comprise a transmural lesion.

5. The system as in claim 1, wherein the passageway comprises an airway within a lung and the distal end of the catheter is configured to be positioned within the airway, and wherein the at least one energy delivery algorithm includes signal parameters causing the functionally continuous treatment area to comprise a vacancy of cell types while maintaining a cartilage layer of the airway.

6. The system as in claim 5, wherein the cell types include epithelial cells, goblet cells and/or submucosal gland cells.

7. The system as in claim 5, wherein the functionally continuous treatment area has a depth of up to and not beyond 2.5 cm.

8. The system as in claim 1, wherein the pulsed electric field energy is biphasic.

9. The system as in claim 1, wherein the at least one energy delivery algorithm provides pulsed electric field energy to the at least one of the plurality of electrodes for less than or equal to 10,000 µs to create the first treatment area and/or each of the at least one additional treatment areas.

10. The system as in claim 9, wherein the at least one energy delivery algorithm provides pulsed electric field energy to the at least one of the plurality of electrodes for less than or equal to 500 µs to create the first treatment area and/or each of the at least one additional treatment areas.

11. The system as in claim 10, wherein the at least one energy delivery algorithm provides pulsed electric field energy to the at least one of the plurality of electrodes for 5 µs-50 µs to create the first treatment area and/or each of the at least one additional treatment areas.

12. The system as in claim 1, wherein the pulsed electric field energy is comprised of 40-500 packets.

13. The system as in claim 12, wherein the pulsed electric field energy is comprised of less than or equal to 10 packets.

14. The system as claim 1, wherein the pulsed electric field energy is delivered in a monopolar arrangement.

15. The system as in claim 1, wherein the at least one additional electrode comprises two to seven additional electrodes.

16. The system as in claim 1, wherein the at least one energy delivery algorithm provides the electric signal of the pulsed electric field energy to each of the first electrode and at least one additional electrode in series.

17. The system as in claim 1, wherein the first treatment area and the at least one additional treatment areas overlap.

18. The system as in claim 17, wherein the at least one energy delivery algorithm is configured to provide the electric signal of the pulsed electric field energy to the first electrode in a plurality of phases and to the at least one additional electrodes in a plurality of differing phases, wherein the plurality of phases and the plurality of differing phases do not coincide.

19. The system as in claim 18, wherein the plurality of phases and the plurality of differing phases form a repetitive pattern.

20. The system as in claim 18, wherein the at least one energy delivery algorithm provides maintenance pulsed electric field energy to the first electrode and/or the at least one additional electrodes in between phases, wherein the maintenance pulsed electric field energy has a lower voltage than the pulsed electric field energy.

21. The system as in claim 20, wherein the maintenance pulsed electric field energy has a voltage of less than half that of the pulsed electric field energy.

22. The system as in claim 1, wherein the first electrode and the at least one additional electrode are mounted on or imbedded in an expandable member.

23. The system as in claim 1, wherein the first electrode and the at least one additional electrode comprises a plurality of wires or ribbons forming an electrode delivery body having an expandable basket shape, wherein a portion of the basket shape is insulated.

\* \* \* \* \*